US009247886B2

(12) United States Patent
Finburgh et al.

(10) Patent No.: US 9,247,886 B2
(45) Date of Patent: Feb. 2, 2016

(54) COMPACT APPARATUS AND METHODS FOR NON-INVASIVELY MEASURING HEMODYNAMIC PARAMETERS

(75) Inventors: Simon E. Finburgh, San Diego, CA (US); Mark W. Perona, San Diego, CA (US); Russell D. Hempstead, Lafayette, CO (US)

(73) Assignee: Tensys Medical, Inc., San Diego, CA (US)

( * ) Notice: Subject to any disclaimer, the term of this patent is extended or adjusted under 35 U.S.C. 154(b) by 579 days.

(21) Appl. No.: 13/113,794

(22) Filed: May 23, 2011

(65) Prior Publication Data

US 2011/0288382 A1 Nov. 24, 2011

Related U.S. Application Data

(63) Continuation of application No. 10/961,460, filed on Oct. 7, 2004, now Pat. No. 7,946,994.

(51) Int. Cl.

*A61B 5/00* (2006.01)
*A61B 5/022* (2006.01)
*A61B 5/06* (2006.01)

(52) U.S. Cl.

CPC ................. *A61B 5/022* (2013.01); *A61B 5/061* (2013.01); *A61B 5/681* (2013.01)

(58) Field of Classification Search

USPC ......................................... 600/301, 485, 304
See application file for complete search history.

(56) References Cited

U.S. PATENT DOCUMENTS 2,753,863 A 7/1956 Bailey
3,090,377 A 5/1963 Salisbury et al.

(Continued)

FOREIGN PATENT DOCUMENTS

DE 4218319 6/1992
EP 0 212 278 7/1986

(Continued)

OTHER PUBLICATIONS

Carson, E. R., et al. (1983) "The Mathematical Modeling of Metabolic and Endocrine Systems: Model Formulation, Identification, and Validation," John Wiley & Sons, NY, pp. 185-189.

(Continued)

*Primary Examiner* — Michael Kahelin
*Assistant Examiner* — Mitchell E Alter
(74) *Attorney, Agent, or Firm* — Gazdzinski & Associates, PC

(57) ABSTRACT

Improved apparatus and methods for non-invasively assessing one or more hemodynamic parameters associated with the circulatory system of a living organism. In one aspect, the invention comprises spatially compact "bracelet" embodiment adapted to accurately place and maintain a sensor (e.g., tonometric pressure sensor) with respect to the anatomy of the subject, including an optional alignment apparatus which moveably captures the sensor to, inter alia, facilitate coupling thereof to an actuator used to position the sensor during measurements. The alignment apparatus also advantageously allows the sensor position to be maintained when the fixture is removed from the subject, such as during patient transport. A completely autonomous variant of the bracelet apparatus having internal power supply and wireless interfaces is also disclosed. Methods for positioning the alignment apparatus and sensor and providing treatment to the subject are also described.

16 Claims, 32 Drawing Sheets

(56) References Cited

U.S. PATENT DOCUMENTS

| | | | | |
|---|---|---|---|---|
| 3,095,873 | A | | 7/1963 | Edmunds |
| 3,527,197 | A | | 9/1970 | Ware et al. |
| 3,535,067 | A | | 10/1970 | Lesher et al. |
| 3,601,120 | A | | 8/1971 | Massie et al. |
| 3,617,993 | A | | 11/1971 | Massie et al. |
| 3,640,123 | A | | 2/1972 | Vogt et al. |
| 3,663,932 | A | | 5/1972 | Mount et al. |
| 3,675,640 | A | | 7/1972 | Gatts |
| 3,704,708 | A | | 12/1972 | Iberall |
| 3,724,274 | A | | 4/1973 | Millar |
| 3,727,250 | A | | 4/1973 | Koehn et al. |
| 3,791,378 | A | | 2/1974 | Hochberg et al. |
| 3,885,551 | A | | 5/1975 | Massie |
| 3,935,984 | A | | 2/1976 | Lichowsky et al. |
| 4,109,647 | A | | 8/1978 | Stern et al. |
| 4,122,843 | A | | 10/1978 | Zdrojkowski |
| 4,127,114 | A | | 11/1978 | Bretscher |
| 4,154,231 | A | | 5/1979 | Russell |
| 4,205,386 | A | | 5/1980 | Ruszala et al. |
| 4,206,765 | A | | 6/1980 | Huber |
| 4,239,047 | A | | 12/1980 | Griggs, III et al. |
| 4,249,540 | A | | 2/1981 | Koyama et al. |
| 4,274,424 | A | | 6/1981 | Kimura et al. |
| 4,280,494 | A | | 7/1981 | Cosgrove, Jr. et al. |
| 4,301,512 | A | | 11/1981 | Keith et al. |
| 4,318,413 | A | | 3/1982 | Iinuma et al. |
| 4,349,034 | A | | 9/1982 | Ramsey, III |
| 4,380,240 | A | | 4/1983 | Jobsis et al. |
| 4,406,289 | A | | 9/1983 | Wesseling et al. |
| 4,441,504 | A | | 4/1984 | Peterson et al. |
| 4,476,875 | A | | 10/1984 | Nilsson et al. |
| 4,500,933 | A | | 2/1985 | Chan |
| 4,566,462 | A | | 1/1986 | Janssen |
| 4,584,880 | A | | 4/1986 | Matzuk |
| 4,590,948 | A | | 5/1986 | Nilsson |
| 4,595,023 | A | | 6/1986 | Bonnet |
| 4,596,254 | A | | 6/1986 | Adrian et al. |
| 4,604,616 | A | | 8/1986 | Buchas |
| 4,608,994 | A | | 9/1986 | Ozawa et al. |
| 4,630,612 | A | | 12/1986 | Uchida et al. |
| 4,651,747 | A | | 3/1987 | Link |
| 4,660,564 | A | | 4/1987 | Benthin et al. |
| 4,664,126 | A | | 5/1987 | Link |
| 4,688,579 | A | | 8/1987 | Inahara |
| 4,695,955 | A | | 9/1987 | Faisandier |
| 4,705,047 | A | | 11/1987 | Bailey |
| 4,718,428 | A | | 1/1988 | Russell |
| 4,719,923 | A | | 1/1988 | Hartwell et al. |
| 4,721,113 | A | | 1/1988 | Stewart et al. |
| 4,729,382 | A | | 3/1988 | Schaffer et al. |
| 4,733,668 | A | | 3/1988 | Torrence |
| 4,736,322 | A | | 4/1988 | Clifford |
| 4,754,401 | A | | 6/1988 | Kaczynski et al. |
| 4,754,761 | A | | 7/1988 | Ramsey, III et al. |
| 4,760,730 | A | | 8/1988 | Frank et al. |
| 4,771,792 | A | | 9/1988 | Seale |
| 4,796,184 | A | | 1/1989 | Bahr et al. |
| 4,802,488 | A | * | 2/1989 | Eckerle ......................... 600/485 |
| 4,838,275 | A | | 6/1989 | Lee |
| 4,867,170 | A | | 9/1989 | Takahashi |
| 4,868,476 | A | | 9/1989 | Respaut |
| 4,869,261 | A | | 9/1989 | Penaz |
| 4,880,013 | A | | 11/1989 | Chio |
| 4,889,132 | A | | 12/1989 | Hutcheson et al. |
| 4,901,733 | A | | 2/1990 | Kaida et al. |
| 4,924,871 | A | | 5/1990 | Honeyager |
| 4,953,557 | A | | 9/1990 | Frankenreiter et al. |
| 4,960,128 | A | | 10/1990 | Gordon et al. |
| 4,974,607 | A | | 12/1990 | Miwa |
| 4,993,422 | A | | 2/1991 | Hon et al. |
| 4,995,399 | A | | 2/1991 | Hayashi et al. |
| 4,998,534 | A | | 3/1991 | Claxton, III et al. |
| 5,012,411 | A | | 4/1991 | Policastro et al. |
| 5,016,631 | A | | 5/1991 | Hogrefe |
| 5,029,589 | A | | 7/1991 | Kato |
| 5,030,956 | A | | 7/1991 | Murphy |
| 5,033,471 | A | | 7/1991 | Yokoe et al. |
| 5,042,307 | A | | 8/1991 | Kato |
| 5,050,613 | A | | 9/1991 | Newman et al. |
| 5,072,733 | A | | 12/1991 | Spector et al. |
| 5,094,244 | A | | 3/1992 | Callahan et al. |
| 5,101,828 | A | | 4/1992 | Welkowitz et al. |
| 5,119,822 | A | | 6/1992 | Niwa |
| 5,124,661 | A | | 6/1992 | Zelin et al. |
| 5,135,002 | A | | 8/1992 | Kirchner et al. |
| 5,146,401 | A | | 9/1992 | Bansal et al. |
| 5,152,297 | A | | 10/1992 | Meister et al. |
| 5,158,091 | A | | 10/1992 | Butterfield et al. |
| 5,163,438 | A | | 11/1992 | Gordon et al. |
| 5,165,416 | A | | 11/1992 | Shinoda et al. |
| 5,170,796 | A | | 12/1992 | Kobayashi |
| 5,193,547 | A | | 3/1993 | Evans, II et al. |
| 5,238,000 | A | | 8/1993 | Niwa |
| 5,240,007 | A | | 8/1993 | Pytel et al. |
| 5,241,964 | A | | 9/1993 | McQuilkin |
| 5,251,631 | A | | 10/1993 | Tsuchiko et al. |
| 5,261,412 | A | * | 11/1993 | Butterfield et al. ........... 600/485 |
| 5,261,414 | A | | 11/1993 | Aung et al. |
| 5,264,958 | A | | 11/1993 | Johnson |
| 5,271,405 | A | | 12/1993 | Boyer et al. |
| 5,273,046 | A | | 12/1993 | Butterfield et al. |
| 5,280,787 | A | | 1/1994 | Wilson et al. |
| 5,284,150 | A | | 2/1994 | Butterfield et al. |
| 5,289,823 | A | | 3/1994 | Eckerle |
| 5,309,916 | A | | 5/1994 | Hatschek |
| 5,313,952 | A | | 5/1994 | Hoch |
| 5,322,069 | A | | 6/1994 | Gallant et al. |
| 5,325,865 | A | | 7/1994 | Beckman et al. |
| 5,327,893 | A | | 7/1994 | Savic |
| 5,329,931 | A | | 7/1994 | Clauson et al. |
| 5,351,694 | A | | 10/1994 | Davis et al. |
| 5,363,849 | A | | 11/1994 | Suorsa et al. |
| 5,368,039 | A | | 11/1994 | Moses |
| 5,391,131 | A | | 2/1995 | Gordon |
| 5,406,952 | A | | 4/1995 | Barnes et al. |
| 5,409,010 | A | | 4/1995 | Beach et al. |
| 5,425,375 | A | | 6/1995 | Chin et al. |
| 5,437,284 | A | | 8/1995 | Trimble |
| 5,439,001 | A | | 8/1995 | Butterfield et al. |
| 5,450,850 | A | | 9/1995 | Iinuma |
| 5,450,852 | A | | 9/1995 | Archibald et al. |
| 5,467,771 | A | | 11/1995 | Narimatsu et al. |
| 5,479,096 | A | | 12/1995 | Szczyrbak et al. |
| 5,479,928 | A | | 1/1996 | Cathignol et al. |
| 5,485,848 | A | | 1/1996 | Jackson et al. |
| 5,487,386 | A | | 1/1996 | Wakabayashi et al. |
| 5,494,043 | A | | 2/1996 | O'Sullivan et al. |
| 5,495,852 | A | | 3/1996 | Stadler et al. |
| 5,533,511 | A | | 7/1996 | Kaspari et al. |
| 5,551,434 | A | | 9/1996 | Iinuma |
| 5,551,440 | A | | 9/1996 | Miyawaki |
| 5,568,815 | A | | 10/1996 | Raynes et al. |
| 5,590,649 | A | | 1/1997 | Caro et al. |
| 5,606,977 | A | | 3/1997 | Ramsey et al. |
| 5,617,857 | A | | 4/1997 | Chader et al. |
| 5,617,867 | A | | 4/1997 | Butterfield et al. |
| 5,623,925 | A | | 4/1997 | Swenson et al. |
| 5,634,467 | A | | 6/1997 | Nevo |
| 5,640,964 | A | | 6/1997 | Archibald et al. |
| 5,642,733 | A | | 7/1997 | Archibald et al. |
| 5,649,542 | A | | 7/1997 | Archibald et al. |
| 5,649,543 | A | | 7/1997 | Hosaka et al. |
| 5,680,869 | A | | 10/1997 | Ogura |
| 5,699,807 | A | | 12/1997 | Motogi et al. |
| 5,701,898 | A | | 12/1997 | Adam et al. |
| 5,709,212 | A | | 1/1998 | Sugo et al. |
| 5,718,229 | A | | 2/1998 | Pesque et al. |
| 5,720,292 | A | | 2/1998 | Poliac |
| 5,720,293 | A | | 2/1998 | Quinn et al. |
| 5,722,414 | A | | 3/1998 | Archibald et al. |
| 5,735,799 | A | | 4/1998 | Baba et al. |
| 5,738,103 | A | | 4/1998 | Poliac |
| 5,749,361 | A | | 5/1998 | Mateyko |
| 5,749,364 | A | | 5/1998 | Sliwa et al. |

(56) References Cited

U.S. PATENT DOCUMENTS 5,755,670 A 5/1998 McKown et al.
5,785,650 A 7/1998 Akasaka et al.
5,785,654 A 7/1998 Iinuma et al.
5,797,850 A 8/1998 Archibald et al.
5,810,724 A 9/1998 Gronvall
5,832,924 A 11/1998 Archibald et al.
5,833,602 A 11/1998 Osemwota
5,833,618 A 11/1998 Caro et al.
5,848,970 A 12/1998 Voss et al.
5,855,557 A 1/1999 Lazenby
5,857,777 A 1/1999 Schuh
5,857,967 A 1/1999 Frid et al.
5,868,679 A 2/1999 Miyazaki
5,873,834 A 2/1999 Yanagi et al.
5,876,343 A 3/1999 Teo
5,876,346 A 3/1999 Corso
5,876,347 A 3/1999 Chesney et al.
5,882,311 A 3/1999 O'Rourke
5,895,359 A 4/1999 Peel, III
5,904,654 A 5/1999 Wohltmann et al.
5,908,027 A 6/1999 Butterfield et al.
5,916,180 A 6/1999 Cundari et al.
5,919,141 A 7/1999 Money et al.
5,921,936 A 7/1999 Inukai et al.
5,931,791 A 8/1999 Saltzstein et al.
5,938,597 A 8/1999 Stratbucker
5,938,618 A 8/1999 Archibald et al.
5,941,828 A 8/1999 Archibald et al.
5,964,711 A 10/1999 Voss et al.
5,987,519 A 11/1999 Peifer et al.
5,993,394 A 11/1999 Poliac
6,010,457 A 1/2000 O'Rourke
6,017,314 A 1/2000 Poliac
6,018,677 A 1/2000 Vidrine et al.
6,027,452 A 2/2000 Flaherty et al.
6,032,109 A 2/2000 Ritmiller, III
6,047,201 A 4/2000 Jackson, III
6,068,601 A 5/2000 Miyazaki et al.
6,080,106 A 6/2000 Lloyd et al.
6,099,477 A 8/2000 Archibald et al.
6,105,055 A 8/2000 Pizano et al.
6,132,382 A 10/2000 Archibald et al.
6,141,572 A 10/2000 Haas
6,159,157 A 12/2000 Archibald et al.
6,171,237 B1 1/2001 Avitall et al.
6,176,831 B1 1/2001 Voss et al.
6,228,033 B1 5/2001 Koobi et al.
6,228,034 B1 5/2001 Voss et al.
6,231,517 B1 5/2001 Forstner
6,232,764 B1 5/2001 Rettig et al.
6,241,679 B1 6/2001 Curran
6,245,022 B1 6/2001 Archibald et al.
6,258,031 B1 7/2001 Sunagawa et al.
6,267,728 B1 7/2001 Hayden
6,270,461 B1 8/2001 Chio
6,290,650 B1 9/2001 Butterfield
6,298,255 B1 10/2001 Cordero et al.
6,313,729 B1 11/2001 Winterer et al.
6,322,516 B1 11/2001 Masuda et al.
6,334,850 B1 1/2002 Amano et al.
6,336,900 B1 1/2002 Alleckson et al.
6,340,349 B1 1/2002 Archibald et al.
6,371,921 B1 4/2002 Caro et al.
6,381,562 B2 4/2002 Keane
D458,375 S 6/2002 Thede
6,443,906 B1 9/2002 Ting et al.
6,471,646 B1 10/2002 Thede
6,471,655 B1 10/2002 Baura
6,478,744 B2 11/2002 Mohler
6,514,211 B1 2/2003 Baura
6,520,920 B2 2/2003 Nissila et al.
6,544,188 B1 4/2003 Chesney
6,554,773 B1 4/2003 Nissila et al.
6,554,774 B1 4/2003 Miele
6,558,335 B1 5/2003 Thede
6,589,185 B1 7/2003 Archibald et al.
6,602,198 B2 8/2003 Yokozeki
6,612,993 B2 9/2003 Narimatsu
6,632,181 B2 10/2003 Flaherty et al.
6,658,298 B2 12/2003 Gruzdowich et al.
6,676,600 B1 1/2004 Conero et al.
6,695,789 B2 2/2004 Thede et al.
6,705,990 B1 3/2004 Gallant et al.
6,711,424 B1 3/2004 Fine et al.
6,730,038 B2 5/2004 Gallant et al.
6,733,462 B1 5/2004 Frick et al.
6,932,772 B2 8/2005 Kan
6,974,419 B1 * 12/2005 Voss et al. .................... 600/485
7,048,691 B2 5/2006 Miele et al.
2001/0039383 A1 11/2001 Mohler
2002/0026121 A1 2/2002 Kan
2002/0055680 A1 5/2002 Miele et al.
2002/0062086 A1 5/2002 Miele et al.
2002/0125164 A1 9/2002 Bassinson
2002/0133210 A1 9/2002 Gruzdowich et al.
2003/0004421 A1 1/2003 Ting et al.
2003/0111005 A1 6/2003 Lord et al.
2003/0141916 A1 7/2003 Conero
2003/0149369 A1 8/2003 Gallant et al.
2003/0153824 A1 8/2003 Tsubata
2004/0059234 A1 3/2004 Martin et al.
2004/0073123 A1 * 4/2004 Hessel et al. ................. 600/490
2004/0167409 A1 8/2004 Lo et al.
2004/0186386 A1 9/2004 Kolluri et al.
2004/0210143 A1 10/2004 Gallant et al.
2005/0038346 A1 2/2005 Miele
2005/0049501 A1 3/2005 Conero et al.
2005/0070837 A1 3/2005 Ferrarini et al.
2005/0080345 A1 4/2005 Finburgh et al.
2006/0079792 A1 4/2006 Finburgh et al.
2006/0094965 A1 5/2006 Voss et al.
2006/0184051 A1 8/2006 Hempstead et al.
2006/0206032 A1 9/2006 Miele et al.

FOREIGN PATENT DOCUMENTS

EP 284 095 3/1988
EP 284 096 3/1988
EP 0 342 249 5/1988
EP 0299 827 6/1988
EP 0 466 272 7/1991
EP 0 587 686 2/1992
EP 0 595 668 9/1993
EP 0595 666 9/1993
EP 0 603 666 12/1993
EP 0818 176 7/1996
FR 2 557 318 12/1983
FR 2 758 709 7/1998
WO WO 84/00290 2/1984
WO WO 92/07508 5/1992
WO WO 95/00074 1/1995
WO WO 95/13014 5/1995
WO WO 97/29678 2/1997
WO WO 98/25511 6/1998
WO WO 98/51211 11/1998
WO WO 00/03635 7/1999

OTHER PUBLICATIONS

Computerized Screening, Inc. (CSI) Celebrates 25 Years as Visionary Pioneer in Preventive Screening Technology Article by KNB Communications, posted on Friday, May 2, 2003 (2 pages).

SQU Journal of Medical Sciences Article re Non-dipping Blood Pressure in Normotensive Patients with Obstructive Sleep Apnea by Bazdawi Al-Riyami, Hussain S. Al-Khatim and Mohammad O Hassan (1 page).

Noninvasive Cardiovascular Monitoring (CircMon) information by JR Medical Ltd. (5 pages).

Drzewiecki, G. (1995) "Noninvasive Assessment of Arterial Blood Pressure and Mechanics," The Biomedical Engineering Handbook CRC Pres Boca Raton, FL, pp. 1196-1211.

Hartley, C.J., et al. (1991) "An Ultrasonic Method for Measuring Tissue Displacement: Technical Details and Validation for Measuring Myocardial Thickening," IEEE Trans Biomed, 38:735-747.

(56) References Cited

OTHER PUBLICATIONS

Cariou, Alain, et al. (1998) "Noninvasive Cardiac Output Monitoring by Aortic Blood Flow Determination: Evaluation of the Sometec Cynemo-3000 System," Critical Care Medicine, vol. 26, No. 12, pp. 2066-2072.
Advertisement for HemoSonic,TM. 100 by Arrow International—licensed under U.S. Pat. No. 5,479,928 listed above.
Mehra, Mandeep R., et al. (May/Jun. 2000) "Emergence of Electronic Home Monitoring in Chronic Heart Failure: Rationale, Feasibility, and Early Results with the HomMed Sentry-Observer System," (consisting of 3 pages).
Anderson, E.A., et al. (1989) "Flow-Mediated and Reflex Changes in Large Peripheral Artery Tone in Humans," Circulation 79:93-100.
Boashash, B., et al. (1987) "An Efficient Real-Time Implementation of the Wigner-Ville Distribution," IEEE Trans ASSP 35:1611-1618.
Drzewiecki, G.M., et al. (1985) Generalization of the Transmural Pressure-Area Relation for the Femoral Artery, 7.sup.th Annual IEEE EMBS Conference 507.
Hoeks, A.P.G., et al. (1985) Transcutaneous Detection of Relative Chages in Artery Diameter, Ultrasound in Med and Bio 11:51-59.
Clinical Science (1998) 95, 669-679 article entitled "Non-invasive Measurements of Arterial Structure and Function: Repeatability, Interrelationships and Trial Sample Size" by Yu-Lu Liang, et al. (11 pages) (http://www.clinsci.org).
Clinical Cardiology article entitled "Apparent Bigeminy and Pulsus Alternans in Intermittent Left Bundle-Branch Block" by Laszlo Littmann, M.D. and Jeffrey R. Goldberg. M.D., Departments of Internal Medicine and Family Practice, Carolinas Medical Center, Charlotte, NC (Jun. 1999) (3 pages) (www.clinicalcardiology.org).
Article entitled "A Fourier Transform Based Tof-Hreels Spectrometer" by R.H. Jackson, L.J. LeGore, Z. Yang, P. Kleban and B.G. Frederick, Laboratory for Surface Science and Technology (LASST) and Dept. of Chemistry, Univ. of Maine, Orono, ME (no date) (1 page/p. O-36).
System Theory and Frequency-Selective Fitters (advance copy) (Jun. 20, 2002) G. Baura, (6 pages/pp. 3, 24-28).
Article entitled "Dynamic Ventilatory Response to CO.sub.2 in Congestive Heart Failure Patients With and Without Central Sleep Apnea" by Zbigniew L. Topor. Linda Johannson, Jerry Kasprzyk and John E. Remmers, Center for Biomedical Engineering, Univ. of Kentucky (rec'd Feb. 7, 2000/accepted Feb. 28, 2001) (9 pages/pp. 408-416) (www.jap.org).
American Journal of Respiratory and Critical Care Medicine, vol. 158, No. 4 article entitled "Instability of Ventilatory Control in Patients with Obstructive Sleep Apnea" by David W. Hudgel, Elizabeth A. Gordon, Sitthep Thanakitchara and Eugene M. Bruce, Case Western Reserve Univ. MetroHealth Medical Center, Cleveland, Ohio (Oct. 1998) (pp. 1142-1149) (http://ajrccm.alsjournals.org).
American Journal Regulatoly Integrative Comp Physiol article entitled "Dynamic Baroreflex Control of Blood Pressure: Influence of the Heart vs. Peripheral Resistance" by Huang-Ku Liu, Sarah-Jane, Guild, et al., Depts. of Physiology and Electrical and Electronic Engineering, Univ. of Auckland, New Zealand (rec'd Jun. 14, 2001/ accepted Mar. 22, 2002) (10 pages/pp. R533-R542) (www.ajpregu.org).
"Transient", The American Hertiage Dictionary of the English Language, 2000, Houghton Mifflin Company, p. 1, http://dictionary.reference.com/search?g=translent.
Jameco Electronics Catalog, pp. 1-14, Copyright 1998 by the National Semiconductor Corporation (USA), http://www.national.com.
Article entitled "Monitoring Vital Signs in Clinical and Research Animals" by Janice M. Bright, Cardiology Consultant, Vetronics, Inc.—Current Separations 16:2 (1997) (4 pages/pp. 43-46).
System Specification for SphygmoCor Pulse Wave Analysis System: Model SCOR-Px (no date) (2 pages) (http://www.owymedical.com).
"Annals of Internal Medicine Established in 1927 by the American College of Physicians" by M. Chiara Cavallino, MD, et al., Association of the Auscultatory Gap with Vascular Disease in Hypertensive Patients, vol. 124, Issue 10, (11 pages/pp. 877-883). (May 15, 1996) (http://www.annals.org).
Circulation 1996; 93:2135-2141 article entitled "Randomized. Double-Blind, Placebo-Controlled Study of Supplemental Oral L-Arginine in Patients With Heart Failure" by Thomas S. Rector, PhD, et al. (pp. 1-21) (http://circ.ahajournals.org).

* cited by examiner

COMPACT APPARATUS AND METHODS FOR NON-INVASIVELY MEASURING HEMODYNAMIC PARAMETERS

PRIORITY

This application is a continuation of and claims priority to co-owned and co-pending U.S. patent application Ser. No. 10/961,460 of the same title filed Oct. 7, 2004, which is incorporated herein by reference in its entirety.

RELATED APPLICATIONS

The present application is related to U.S. patent application Ser. No. 10/269,801 filed Oct. 11, 2002 and entitled "Apparatus and Methods for Non-Invasively Measuring Hemodynamic Parameters", and Ser. No. 10/920,999 filed Aug. 17, 2004 of the same title, both incorporated herein by reference in their entirety.

BACKGROUND OF THE INVENTION

1. Field of the Invention

This invention relates generally to apparatus and methods for monitoring parameters associated with the circulatory system of a living subject, and specifically in one embodiment to the non-invasive monitoring of e.g., arterial blood pressure.

2. Description of Related Technology

The accurate, continuous, non-invasive measurement of blood pressure has long been sought by medical science. The availability of such measurement techniques would allow the caregiver to continuously monitor a subject's blood pressure accurately and in repeatable fashion without the use of invasive arterial catheters (commonly known as "A-lines") in any number of settings including, for example, surgical operating rooms where continuous, accurate indications of true blood pressure are often essential.

Several well known techniques have heretofore been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above have generally been somewhat effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers generally to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Other prior art techniques have sought to more accurately place a single tonometric sensor laterally above the artery, thereby more completely coupling the sensor to the pressure variations within the artery. However, such systems may place the sensor at a location where it is geometrically "centered" but not optimally positioned for signal coupling, and further typically require comparatively frequent re-calibration or repositioning due to movement of the subject during measurement. Additionally, the methodology for proper initial and follow-on placement is awkward, essentially relying on the caregiver to manually locate the optimal location for sensor placement on the subject each time, and then mark that location (such as by keeping their finger on the spot, or alternatively marking it with a pen or other marking instrument), after which the sensor is placed over the mark.

Tonometry systems are also commonly quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery. Many of the foregoing approaches similarly suffer from not being able to maintain a constant angular relationship with the artery regardless of lateral position, due in many cases to positioning mechanisms which are not adapted to account for the anatomic features of the subject, such as curvature of the wrist surface.

Another deficiency of prior art non-invasive hemodynamic measurement technology relates to the lack of disposability of components associated with the device. Specifically, it is desirable to make portions of the device which may (i) be contaminated in any fashion through direct or indirect contact with the subject(s) being monitored); (ii) be specifically calibrated or adapted for use on that subject; (iii) lose calibration through normal use, thereby necessitating a more involved recalibration process (as opposed to simply replacing the component with an unused, calibrated counterpart), or (iv) disposable after one or a limited number of uses. This feature is often frustrated in prior art systems based on a lack of easy replacement of certain components (i.e., the components were not made replaceable during the design process), or a prohibitively high cost associated with replacing components that are replaceable. Ideally, certain components associated with a non-invasive hemodynamic assessment device would be readily disposable and replaced at a very low cost to the operator. Yet another disability of the prior art concerns the ability to conduct multiple hemodynamic measurements on a subject at different times and/or different locations. For example, where blood pressure measurements are required in first and second locations (e.g., the operating room and recovery room of a hospital), prior art methodologies necessitate either (i) the use of an invasive catheter (A-line), (ii) transport of the entire blood pressure monitoring system between the locations, or (iii) disconnection of the subject at the first monitoring location, transport, and then subsequent connection to a second blood pressure monitoring system at the second location.

The disabilities associated with invasive catheters are well understood. These include the need to perforate the subject's skin (with attendant risk of infection), and discomfort to the subject.

Transport of the entire blood pressure monitoring system is largely untenable, due to the bulk of the system and the desire to maintain monitoring equipment indigenous to specific locations.

Disconnection and subsequent reconnection of the subject is also undesirable, since it requires placing a sensor or apparatus on the patient's anatomy a second time, thereby necessitating recalibration, and reducing the level of confidence that the measurements taken at the two different locations are in fact directly comparable to one another. Specifically, since the sensor and supporting apparatus is physically withdrawn at the first location, and then a new sensor subsequently placed again on the subject's tissue at the second location, the likelihood of having different coupling between the sensor and the underlying blood vessel at the two locations is significant. Hence, identical intra-vascular pressure values may be reflected as two different values at the different locations due to changes in coupling, calibration, sensor parameters, and related factors, thereby reducing the repeatability and confidence level associated the two readings.

Another disability of the prior art relates to the lack of any readily implemented and reliable means or mechanism for correction of blood pressure readings for differences in hydrostatic pressure resulting from differences in elevation between the pressure sensor and the organ of interest. For example, where a surgeon or health care provider wishes to know the actual pressure in the brain or head of the subject, the pressure reading obtained from another location of the body (e.g., the radial artery) must be corrected for the fact that the subject's blood volume exerts additional pressure at the radial artery, presumed to be lower in elevation than the subject's head. The additional pressure is the result of the hydrostatic pressure associated with the equivalent of a "column" of blood existing between the radial artery and the uppermost portions of the subject's anatomy.

Additionally, differences in pressure resulting from hydrodynamic effects associated with the cardiovascular system. While quite complex and sophisticated, the circulatory system of a living being is in effect a piping system which, inter cilia, generates flow resistance and therefore head loss (pressure drop) as a function of the blood flow there through. Hence, significant difference between the pressures measured at the output of the heart and the radial artery may exist due to purely hydrodynamic effects.

Prior art techniques for correcting for hydrostatic pressure difference generally comprise measuring the difference in elevation between the measurement location and the organ of interest, and then performing a manual or hand calculation of the hydrostatic pressure correction resulting from this difference, based on an assumed gravitational field vector magnitude g (commonly rounded to 9.8 $m/s^2$). Such techniques are cumbersome at best, and prone to significant errors at worst.

Yet another disability with many prior art systems relates to their bulk and size, especially those portions of the apparatus affixed to the subject; e.g., at the radial artery. Simply stated, the smaller and lighter the device, the greater the degree of flexibility with respect to orientation and placement of the subject and their limbs. For example, certain types of surgical procedures require one or more arms of the subject to be placed tightly at their side(s), which can be difficult where the blood pressure measurement device disposed on the radial artery is bulky and heavy. Similarly, when it is desired to "dangle" the subject's arm, excessive weight of such prior art devices can cause undue stress on and perhaps even injury to the subject being monitored. The weight of the apparatus also tends to change the physical dynamics of the non-invasive measurement process, thereby reducing accuracy and repeatability.

Furthermore, such bulk can cause the caregiver to place the subject's anatomy in a specific orientation (which may or may not be optimal) to accommodate the apparatus. This, coupled with typically several wires or cords running from the apparatus to a parent monitor or other device, makes the use of the prior art apparatus difficult in certain circumstances, and can significantly add to the clutter of an already crowded surgical area, thereby restricting movement of both the subject and any surgical or caregiver personnel.

Based on the foregoing, there is needed an improved apparatus and methodology for accurately, continuously, and non-invasively measuring blood pressure within a living subject. Such improved apparatus and methodology would ideally allow for prompt and accurate initial placement of the tonometric sensor(s), while also providing robustness and repeatability of placement under varying patient physiology and environmental conditions. Such apparatus would also incorporate low cost and disposable components, which could be readily replaced in the event of contamination or loss of calibration/performance (or purely on a preventive or periodic basis). A very small, compact and lightweight form factor is also highly desired, and a lack of direct (wired) electrical connections is ideal in certain applications.

Such apparatus and methods would furthermore be easily utilized and maintained by both trained medical personnel and untrained individuals, thereby allowing certain subjects to accurately and reliably conduct self-monitoring and maintenance of the system.

SUMMARY OF THE INVENTION

The present invention satisfies the aforementioned needs by an improved apparatus and methods for non-invasively and continuously assessing hemodynamic properties, including arterial blood pressure, within a living subject.

In a first aspect of the invention, an improved hemodynamic assessment apparatus is disclosed. In one embodiment, the apparatus comprises at least one sensor adapted to generate first signal relating to the pressure applied thereto; a substantially U-shaped body adapted to adjustably clamp onto a limb proximate a blood vessel of interest; an actuator coupled to the at least one sensor and the body, the actuator being adapted to controllably applanate the at least one sensor against the tissue of the limb proximate the blood vessel; and a signal interface adapted to transfer second signals to an external device, the external device being adapted to generate an estimate of the blood pressure based at least in part on the second signals.

In a second aspect of the invention, a selectively controllable pivot apparatus is disclosed. In one embodiment, the pivot apparatus comprises: at least first and second movable components, the components being rotatably disposed around respective ones of at least first and second axes; at least one control mechanism adapted to selectively control the motion of the at least first and the components; and an actuator mechanism, operatively coupled to the locking mechanism, the actuator allowing selective control of the motion of at least first and second components by movement thereof.

In a third aspect of the invention, a non-invasive blood pressure measurement apparatus adapted for use on radial artery of a living subject is disclosed. In one embodiment, the apparatus comprises: an articulated body adapted to fit over a substantial fraction of the circumference of the subject's wrist area; a sensor assembly having at least one pressure sensor adapted to sense pressure data from the artery; a sensor actuator adapted to movably position the at least one pressure sensor relative to the tissue and the artery; and a support element adapted to at least support the at least one sensor prior to coupling to the actuator; wherein the body and support element further cooperate to stabilize the body.

In a fourth aspect of the invention, a hemodynamic assessment apparatus is disclosed, comprising in one embodiment: a bracelet adapted to receive a portion of the anatomy of a living subject; actuator apparatus substantially integral with the bracelet and adapted to move a sensor; and alignment apparatus adapted to mate with a portion of the anatomy, the alignment apparatus configured to maintain a desired orientation of the sensor prior to coupling thereof to the actuator.

In a fifth aspect of the invention, improved hemodynamic assessment apparatus, is disclosed, in one embodiment comprising: a spatially compact structure adapted to securely receive at least a portion of the anatomy of a living subject, the structure having a plurality of articulated elements, the articulated elements at least allowing the structure to be particularly adapted to the anatomy of the subject; an alignment apparatus adapted couple to the structure and to receive a sensor at least partly therein; and a coupling element cooperating with the alignment apparatus and the sensor to initially position the sensor with respect to the anatomical portion; wherein the coupling element is adapted to be removable from the assessment apparatus to permit variable positioning of the sensor subsequent to the initial positioning.

In a sixth aspect of the invention, a blood pressure monitoring system is disclosed. In one embodiment, the system comprises: at least one pressure sensor adapted to measure a pressure waveform from a blood vessel in the wrist area of a living subject; an actuator adapted to control the position of the at least one sensor relative to the blood vessel; and a structure adapted to be worn substantially around the wrist area and to maintain the actuator in a substantially constant position with respect to the blood vessel; wherein the structure comprises a gap and can be placed on the wrist area by passing at least a portion of the wrist area through the gap.

In a seventh aspect of the invention, a non-invasive blood pressure monitoring apparatus is disclosed, in one embodiment comprising: a bracelet-like structure having a sensor; and signal processing apparatus, the processing apparatus adapted to generate scaled blood pressure signals based on data obtained using the sensor from a living subject, the scaled signals being scaled at least in part using at least one physiologic parameter associated with the subject, such as for example their body mass index (BMI) or a quantity related thereto.

In an eighth aspect of the invention, apparatus adapted to position a sensor relative to a portion of the human anatomy is disclosed. In one embodiment, the apparatus comprises: a first contact element; a second contact element disposed in substantial opposition to the first element and adapted to hold the sensor; and a third element, the third element being hingedly coupled to the first and second elements, the hinged coupling allowing selective adjustment of the apparatus on the portion of the anatomy.

In a ninth aspect of the invention, improved joint apparatus for controlling the position of a hemodynamic sensing apparatus with respect to a living subject is disclosed. In one embodiment, the apparatus is configured such that actuation of a single mechanism of the joint apparatus permits adjustment of at least two pivots associated with the sensing apparatus. In one variant, the single mechanism comprises two substantially opposed buttons.

In a tenth aspect of the invention, joint apparatus for controlling the position of a hemodynamic sensing apparatus with respect to a living subject is disclosed, in one embodiment comprising a mechanism adapted to sense the preload applied to the sensing apparatus and selectively lock the position of the apparatus when a desired preload level is reached.

In an eleventh aspect of the invention, improved physiologic sensing apparatus is disclosed. In one embodiment, the apparatus comprises: at least one pressure sensor; and a substantially U-shaped support structure adapted to receive at least a portion of the anatomy of a subject therein; wherein the support structure is adapted to couple at least one force felt by the at least one sensor to the at least portion of the anatomy.

In a twelfth aspect of the invention, improved sensor actuator apparatus is disclosed, comprising in one embodiment: a stationary element; a plurality of components adapted to move relative to the stationary element, at least one of the components further being adapted for coupling to the sensor; and at least one motor fixedly mounted to the stationary element and operatively coupled to at least one of the components, the at least one motor being adapted to move the at least one component in at least a first direction while maintaining the attitude of the sensor substantially constant.

These and several other features of the invention will become apparent from the following description of the invention, taken in conjunction with the accompanying drawings.

DETAILED DESCRIPTION OF THE INVENTION

Figure 1:
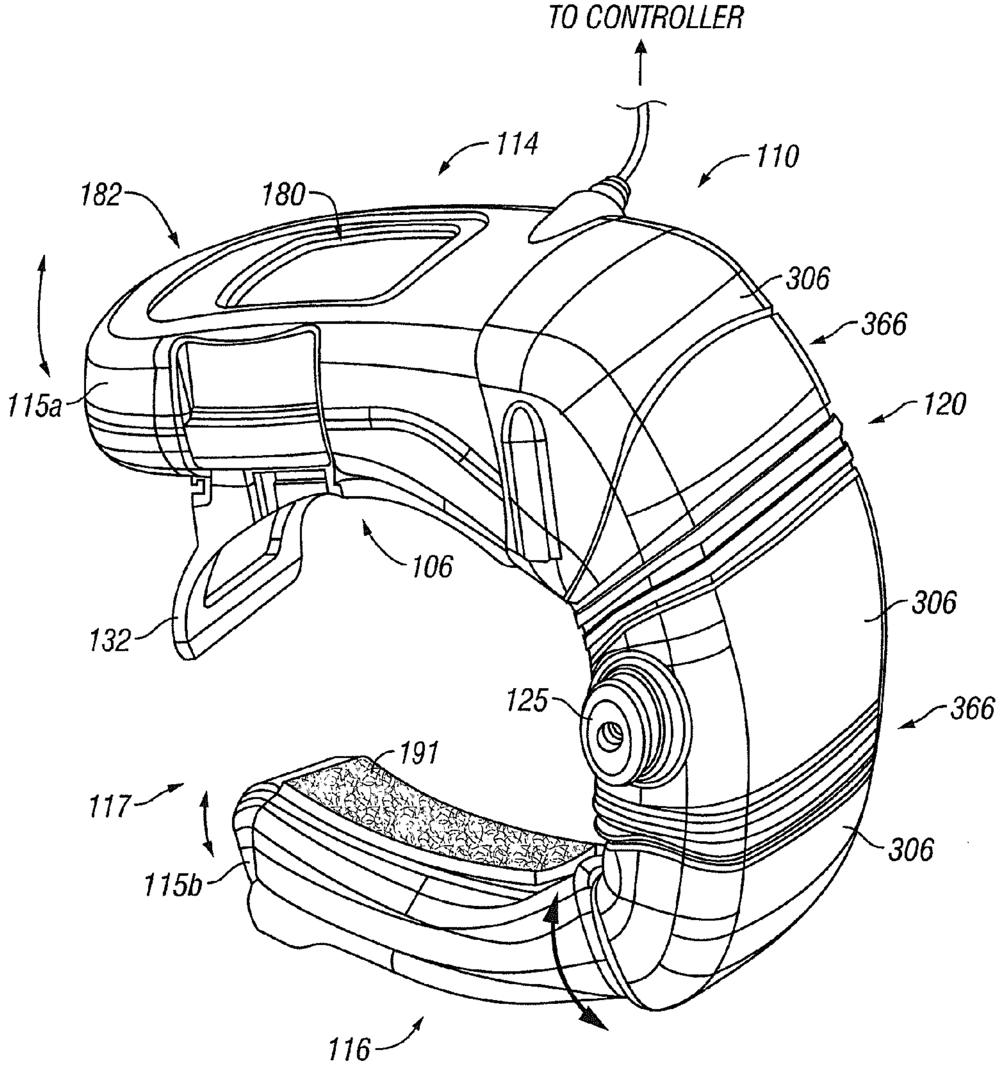
FIG. 1 is a perspective view of one exemplary "bracelet" embodiment of the hemodynamic assessment apparatus of the present invention and associated support frame.

Reference is now made to the drawings wherein like numerals refer to like parts throughout.

It is noted that while the invention is described herein primarily in terms of a method and apparatus for assessment of hemodynamic parameters of the circulatory system via the radial artery (i.e., wrist or forearm) of a human subject, the invention may also be readily embodied or adapted to monitor such parameters at other blood vessels and locations on the human body, as well as monitoring these parameters on other warm-blooded species. All such adaptations and alternate embodiments are readily implemented by those of ordinary skill in the relevant arts provided the present disclosure, and are considered to fall within the scope of the claims appended hereto.

As used herein, the term "hemodynamic parameter" is meant to include parameters associated with the circulatory system of the subject, including for example pressure (e.g., diastolic, systolic, pulse, or mean), blood flow kinetic energy, velocity, density, time-frequency distribution, the presence of stenoses, $SpO_2$, pulse period, as well as any artifacts relating to the pressure waveform of the subject.

Additionally, it is noted that the terms "tonometric," "tonometer," and "tonometery" as used herein are intended to broadly refer to non-invasive surface measurement of one or more hemodynamic parameters such as pressure, such as by placing a sensor in communication with the surface of the skin, although contact with the skin need not be direct (e.g., such as through a coupling medium or other interface).

The terms "applanate" and "applanation" as used herein refer to the direct or indirect compression (relative to a state of non-compression) of tissue, blood vessel(s), and other structures such as tendon or muscle of the subject's physiology. Similarly, an applanation "sweep" refers to one or more periods of time during which the applanation level is varied (either increasingly, decreasingly, or any combination thereof). Although generally used in the context of linear (constant velocity) position variations, the term "applanation" as used herein may conceivably take on any variety of other forms, including without limitation (i) a continuous non-linear (e.g., logarithmic) increasing or decreasing compression over time; (ii) a non-continuous or piece-wise continuous linear or non-linear compression; (iii) alternating compression and relaxation; (iv) sinusoidal or triangular waves functions; (v) random motion (such as a "random walk"; or (vi) a deterministic profile. All such forms are considered to be encompassed by the term.

As used herein, the term "wireless" refers to any sort of non-wired interface including, without limitation, signal, data or electrical interfaces, inductive or capacitive power or signal couplings, and radio frequency, microwave, laser, optical, acoustic/ultrasonic, or infrared couplings.

Overview—

In one fundamental aspect, the present invention comprises improved and highly compact apparatus and associated methods for accurately and repeatably (if desired) disposing one or more sensors with respect to the anatomy of a subject to facilitate subsequent hemodynamic parameter measurements using the sensor(s). For example, as will be described in greater detail below, the present invention is useful for accurately placing a pressure sensor assembly for continuously and non-invasively measuring the blood pressure from the radial artery of a human being using an extremely small and lightweight form factor. However, literally any kind of sensor (ultrasound, optical, etc.) can be used alone or in combination consistent with the invention, including for example the devices and associated techniques described in co-pending and co-owned U.S. patent application Ser. Nos. 09/815,982 entitled "Method and Apparatus for the Noninvasive Assessment of Hemodynamic Parameters Including Blood Vessel Location" filed Mar. 22, 2001, Ser. No. 09/815,080 entitled "Method and Apparatus for Assessing Hemodynamic Parameters within the Circulatory System of a Living Subject" filed Mar. 22, 2001, U.S. Pat. No. 6,554,774 issued Apr. 29, 2003 entitled "Method and apparatus for assessing hemodynamic properties within the circulatory system of a living subject" and Ser. No. 10/920,999 entitled "Apparatus And Methods For Non-Invasively Measuring Hemodynamic Parameters" filed Aug. 17, 2004, each of which are assigned to the assignee hereof and incorporated herein by reference in their entirety. The present invention is particularly compatible with the techniques and apparatus described in co-owned U.S. Pat. No. 6,730,038 to Gallant, et al. issued May 4, 2004 and entitled "Method and Apparatus for Non-Invasively Measuring Hemodynamic Parameters Using Parametrics" and also U.S. patent application Ser. No. 10/393/660 entitled "Method and Apparatus for Control of Non-Invasive Parameter Measurements" filed Mar. 20, 2003, each also incorporated herein by reference in its entirety.

In one exemplary embodiment, the aforementioned pressure sensor is coupled to an actuator mechanism carried by a substantially circumferential "bracelet" assembly worn by the subject in the area of the radial artery. The actuator mechanism, when coupled to the sensor, controls the sensor lateral (and proximal, if desired) position as well as the sagittal position (corresponding to the level of applanation of the underlying tissue) according to any number of control schemes, including for example that set forth in Assignee's co-pending U.S. patent application Ser. No. 10/211,115 filed Aug. 1, 2002, entitled "Method and Apparatus for Control of Non-Invasive Parameter Measurements" and incorporated herein by reference in its entirety, and in U.S. Pat. No. 6,730,038 referenced above. Additionally, an exemplary embodiment provides varying attitude control for the sensor with respect to the blood vessel during applanation if desired.

However, the exemplary embodiment of the present invention is also compatible with systems having separate sensor(s) and applanation mechanisms, as well as combinations of the foregoing features and sensors. The actuator of the invention is advantageously "displacement" driven, and accordingly does not rely on measurements of applied force, but rather merely displacement. This approach greatly simplifies the construction and operation of the actuator (and parent control system) by obviating force sensors and signal processing relating thereto, and further makes the actuator and system more robust.

The apparatus of the present invention also advantageously maintains a highly rigid coupling between the sensor assembly and the "bracelet" used to receive the subject's anatomy, thereby further enhancing the accuracy of the system through elimination of nearly all compliance within the apparatus. In one embodiment, this rigid coupling comprises using the bracelet itself as the stabilizing apparatus. In a second embodiment, the bracelet is further stabilized through use of a brace or support element which provides a stable platform against which the actuator of the bracelet can act.

Other significant features of the present invention include (i) ease of installation and proper adjustment on the subject being monitored; (ii) very light weight and small form factor; (iii) ease and flexibility of use under a variety of different operational environments; (iv) repeatability of measurements; and (v) disposability of certain components. These features are achieved through the use of novel structures and techniques for placing the sensor(s) and operating the device, as well as significant modularity in design and consideration of the constraints relating to the typical (and atypical) clinical environment. Optional wireless signal and even power interfaces may be used with the invention, as well as a compact battery system, to provide for a completely autonomous device.

In one aspect, the present invention overcomes the disabilities associated with the prior art by providing an assembly which has a minimal form factor and which is readily placed on and adjusted to the subject being monitored, thereby increasing the clinical robustness and the range of applications in which the device can be used. Specifically, by providing a small and lightweight "bracelet" (or comparable form) which is easily placed and adjusted to the proper preload, literally any skill level of caregiver (including the subject themselves) can obtain accurate and reliable results in conjunction with most any type of surgical or medical procedure, in an almost completely non-obtrusive manner for the subject. The small form factor is especially useful in providing continuous non-invasive measurements of the subject where the limb (e.g., arm) is constrained next to or against the body (sometimes colloquially referred to as "mummy tuck" position).

Furthermore, the bracelet apparatus is substantially agnostic in terms of which limb it is placed on (e.g., can be used on the left arm or right arm of an individual with equal success, and without any special adaptation or adjustment).

Apparatus for Hemodynamic Assessment—

Referring now to FIGS. 1-4, exemplary embodiments of the hemodynamic assessment apparatus 100 of the invention is described in detail.

FIG. 1 shows generally a first embodiment of the "bracelet" assembly 110 of the invention.

It is known that the ability to accurately measure the pressure associated with a blood vessel depends largely upon the mechanical configuration of the applanation mechanism. Under the typical prior art approaches previously discussed, the pressure transducer alone comprises the applanation mechanism such that the mechanism and transducer are fixed as a single unit. Hence, the pressure transducer experiences the full force applied to deform the tissue, structures, and blood vessel. This approach neglects the component of the applanation force required to compress this interposed tissue, etc. as it relates to the pressure measured tonometrically from the blood vessel. Conversely, under no compression, the magnitude of the pressure within the blood vessel is attenuated or masked by the interposed tissue such that the pressure measured tonometrically is less than that actually existing in the vessel (so-called "transfer loss").

In contrast, the sensor assembly 101 of the present invention (see FIGS. 1*c* and 1*d* discussed below) embodies the pressure transducer assembly 103 disposed within an applanation element 102, the latter having a specially designed configuration adapted to mitigate the effects of such transfer loss in a simple, repeatable, and reliable way such that it can be either (i) ignored or (ii) compensated for as part of the tonometric measurement.

The applanation element 102 (FIG. 1*c*) is coupled to a wrist bracelet assembly 110 (FIG. 1) via an actuator 106 assembly (described in greater detail subsequently herein with respect to FIGS. 3*a*-3*g*) so as to provide a platform against which the motor of the actuator 106 may exert reaction force while applanating the subject's tissue. In the illustrated embodiment, the wrist bracelet assembly 110 comprises an "interior" brace element 114, adapted to fit the inner wrist and hand surfaces of the subject, and an "anterior" element 116 adapted to straddle and communicate with the outside surfaces of the subject's wrist (or optional brace 195, if used) as best shown in FIG. 1.

In the illustrated embodiment, the distal ends 115*a*, 115*b* of the bracelet elements 114, 116 are also made so as to be (i) rounded in form, thereby avoiding any sharp or uncomfortable edges, and (ii) roughly coextensive in projection, thereby creating a gap 117 between the distal ends 115*a*, 115*b* through which the subject's wrist may be passed. Hence, the assembly 110 is somewhat "horseshoe" (or alternatively "U" or "C") shaped when fitted onto the subject's anatomy.

In the present embodiment, the assembly 110 is adapted to be placed onto the selected limb (e.g., wrist area) via the medial region thereof, such that the gap 117 is disposed laterally, although it will be appreciated that other orientations may be used consistent with the invention (including placement via the lateral region so that the gap is disposed medially).

In addition to the interior and anterior elements 114, 116, the bracelet 110 also comprises a selectively adjustable pivot element 120 disposed between and mechanically coupled to the two elements 114, 116. The pivot element 120 (FIGS. 1*f* and 1*h*) of the illustrated embodiment comprises two (2) hinge or pivot axes 121*a*, 121*b* disposed substantially parallel to one another and substantially transverse (normal) to a plane bisecting the interior and anterior elements 114, 116, although it will be recognized that these geometric relationships need not be enforced, and others may be used including a mechanism with a greater or lesser number of axes. The two axes 121*a*, 121*b* allow respective ones of the interior and anterior elements 114, 116 to rotate with respect to the pivot element 120 (and hence each other, indirectly), thereby allowing the size of the gap 117 to vary. This variability of the gap 117 permits, inter alia, the expansion or opening of the device 110 during fitting on or removal from the subject, thereby making the bracelet 110 easier to slide on and off. As will be described in greater detail subsequently herein, this feature also permits the rapid and accurate adjustment of the pre-load (non-applanated compression) of the device prior to hemodynamic assessment.

The pivot element 120 is further configured to be selectively lockable by the user so as to facilitate adjustment thereof as well as maintaining a high degree of rigidity for the bracelet 110 as a whole during use. Specifically, the element 120 includes a locking mechanism 123 controlled via locking/unlocking actuators 124, whereby the user can lock and unlock the mechanism 123 to permit or prevent rotation of the interior/anterior elements around their pivot axes 121*a*, 121*b* (as well as the rotation of the anterior element around its longitudinal axis as described in greater detail below). In the illustrated embodiment, the actuators comprise a set of substantially co-linear buttons 125 with associated rods or bars which selectively engages/disengages one or more clutch mechanisms 126 disposed within the locking mechanism 123, as described in greater detail subsequently herein. The clutch and rod mechanisms are configured to provide a substantially binary or two-state system; i.e., "locked" or "unlocked", although other approaches may be used. Specifically, the buttons, clutch and rod are biased using internal biasing members (e.g., Belville washers) such that rotation around the axes 121*a*, 121*b* is allowed when the buttons are depressed, and not allowed when the buttons are released. This approach is selected for use in the present embodiment for a variety of reasons including inter alia, (i) ease of operation and the mechanism by any level of user, and (ii) providing the user with readily cognizable feedback regarding the state of the mechanism. Furthermore, by constructing the illustrated embodiment of the mechanism 123 such that both buttons must be depressed to release the mechanism for rotation (or alternatively one button pressed, yet with a force greatly exceeding that of normal incidental contact), incidental contact or bumping of one button will not cause the mechanism to unintentionally release.

Regarding ease of operation, the aforementioned binary or discrete state approach advantageously obviates the user having to determine what an appropriate level of friction/resistance for the mechanism is, which notably may also vary as a function of the application and other factors such as ambient temperature, humidity, etc. Stated simply, the exemplary configuration takes any guess-work or ambiguity out of the sizing, patient fitting, and measurement process since the user is only provided two states; i.e., "locked" and "unlocked". The locked state unequivocally locks the mechanism under all applications and conditions, and the unlocked state similarly unlocks the mechanism under all applications and conditions. This relieves the user from having to divine an optimal adjustment level or the like.

Regarding positive feedback, the exemplary mechanism unequivocally tells the user in which of the two states it is operating. This feedback is accomplished both by the appearance of the buttons (i.e., their position relative to the rest of the structure 110, which can be viewed by the operator) and the compliance or moveability of the pivots in the pivot member 120. Other indicia may also be utilized alone or in concert with the foregoing, such as audible feedback ("click" when changing states), indicator LEDs or lights such as those based on a position switch, and the like. For example, in one variant of the illustrated embodiment, a "force profile" is provided for the buttons 125 which has a characteristic that indicates to the user that the buttons are fully seated when pressed. Specifically, the force on the buttons 125 needs to increase to a level at which the buttons begin to move, but once moving the required force mitigates to some degree, so that as the user pushes on the buttons, they "give way" at the appropriate load to let the user feel them move.

Furthermore, the pivot mechanism 120 of the exemplary embodiment is optionally configured such that the two states of the frictional clutch mechanism 123 are asymmetric. Specifically, through proper selection, sizing, and design of the mechanism springs and other components (described below), the "locked" state is made stable as compared to the "unlocked" state, thereby in effect having the mechanism preferentially operate in or default to the locked state (such as when the user's fingers slip off the buttons 125 inadvertently). This approach is employed so as to minimize the opportunity for the user or subject to inadvertently transit from the locked to the unlocked state, which would likely result in an interruption in the hemodynamic measurement underway (and perhaps potentially damage to the sensor assembly or apparatus 110 or render subsequent readings inaccurate). By making the mechanism 123 somewhat "failsafe" to the locked state, a much more deliberate and affirmative action is required by the user or subject to unlock the device.

It will be appreciated, however, that by virtue of the use of clutch mechanisms 126 as described herein, the exemplary embodiment also has the advantage of being able to be opened or unlocked with sufficient force, thereby providing an additional safety mechanism. Specifically, should the buttons 125 jam, or other internal mechanisms fail, leaving the apparatus 110 in the "locked" state on a subject's wrist, the apparatus 110 can be forcibly removed by simply grasping the interior and anterior elements 114, 116 and pulling them apart with sufficient force. Clearly, the level of force necessary to pull the elements 114, 116 apart (which in effect is controlled by the friction of the clutch mechanisms 126) can be adjusted as desired, so as to both avoid inadvertent or undesired loosening and allow the average user to pull the apparatus apart.

Another advantage of the apparatus 100 of the illustrated embodiment relates to its stability. By way of an optional brace element 195 (see FIG. 1*a* and related discussion) and the support frame 132 (FIG. 1*e* and related discussion), the bracelet apparatus 110 provides a highly stable platform for the sensor applanation element 102. The bracelet apparatus 110 is retained in place on the subject's anatomy (e.g., wrist area) through contact with the brace element 195, friction or contact with the skin by portions of the interior and anterior elements 114, 116, as well as its coupling to the support frame 132. In one embodiment, the support frame is further bonded to the user's skin using, e.g., a removable adhesive substance (e.g., tape or coating) which adds yet further rigidity and stability to the system as a whole.

Since the device 110 is comparatively lightweight, it can be readily maintained in the proper orientation with respect to the blood vessel being measured without any further external restraining or positioning mechanisms such as extra straps, adhesive or surgical tape, etc., even during motion by the subject being monitored. As described elsewhere herein, the user merely (i) positions the bracelet 110 (by pressing the buttons 125 and placing the device 110 over the wrist, including the brace element 195 and the sensor support frame 132), and then (ii) adjusts the preload or static compression of the wrist area by the interior/anterior elements 114, 116 of the apparatus 110 by depressing the outer surfaces of the interior and anterior elements. This process is further aided through pre-positioning of the sensor assembly 101, such as by using the reticle and related components as described in detail in co-pending application Ser. No. 10/920,999 filed Aug. 17, 2004 previously incorporated herein.

Hence, positioning and adjustment of the apparatus 110 as a whole is "target" based; i.e., the desired target area of the radial artery or other blood vessel is used as the basis for alignment of the sensor assembly 101, which necessarily dictates alignment of the rest of the apparatus 110 due to the somewhat fixed relationships between the components. Accordingly, proper positioning of the sensor (e.g., via the reticle) necessarily results in proper positioning of the sensor frame, and so forth, thereby removing a significant source of variability associated with many prior art approaches, and making the present apparatus more clinically robust.

In addition to light weight, the exemplary apparatus 110 of FIG. 1 utilizes a very small and compact form factor with a substantially smooth and conformal exterior surface which increases the range of different applications for which it may be used. As previously referenced, certain applications and surgical procedures require precise positioning of the limb(s) of the subject which may conflict with prior art systems due to their bulk, weight, required electrical or other interconnections (e.g., cords, wiring, inflation tubes, etc.). One particular instance relates to surgical procedures where the subject's (available) arm is required to be disposed tightly at their side Under the prior art, monitoring of the radial or brachial artery in such cases is difficult at best and impossible at worst. The present embodiment overcomes this disability by providing a form factor which can be used in literally any orientation and available space. The substantially smooth and regular outer surfaces of the apparatus, including the use of rounded edges on the external surfaces, also help avoid any external devices or objects (such as cords from other surgical devices, latex gloves, etc.) from getting caught or hung up on the apparatus during use. The smooth contours also aide in minimizing pressure points against the patient's anatomy which could lead to tissue damage since the patient may be anaesthetized, and hence cannot feel the pressure or move the relevant limb.

In another aspect of the invention, the apparatus 110 is also optionally fitted with a mechanism adapted to aid the user in proper adjustment of the preload or static compression. As used in the present context, the term "mechanism" refers broadly to any mechanical, electro-mechanical, pneumatic, electrical, or other apparatus. In one embodiment (FIGS. 1*f* and 1*g*), the adjustment mechanism comprises a "cocking and trigger" mechanism 137 which allows the user adjust the preload or tightness of the bracelet 110 after it has been placed and the buttons 125 have been released.

With the pivot mechanism 120 in the unlocked state (i.e., buttons depressed) as previously described, the user places the bracelet apparatus 110 over the wrist area of the subject, aligning the pre-positioned sensor assembly 101 with the corresponding adapter portion 377 of the actuator 106 (described elsewhere herein) and brace element 195 with the anterior element 116, and simply applies compressive force with their hand to move the interior and anterior elements 114, 116 closer to one another around the subject's wrist. At this point, the bracelet 110 is loosely adjusted on the subject's wrist, yet the preload is not yet adjusted.

Accordingly, to adjust the preload, the user simply grasps the outer portions of the interior and anterior elements (including placing their thumb or forefingers within the optional recess 180 formed in the outer surface of the interior element 114 as shown best in FIG. 1), and presses the two elements 114, 116 closer together in a clamping fashion. The cocked trigger mechanism 137 is then actuated (uncocked) when sufficient preload (compressive pressure) is achieved, thereby locking the axes of the pivot mechanism 120 in place. The rotation of the distal portion of the anterior element 116 around its axis is also locked by actuation of the trigger mechanism 137 as described in detail subsequently herein with respect to FIG. 2.

Figure 1A:
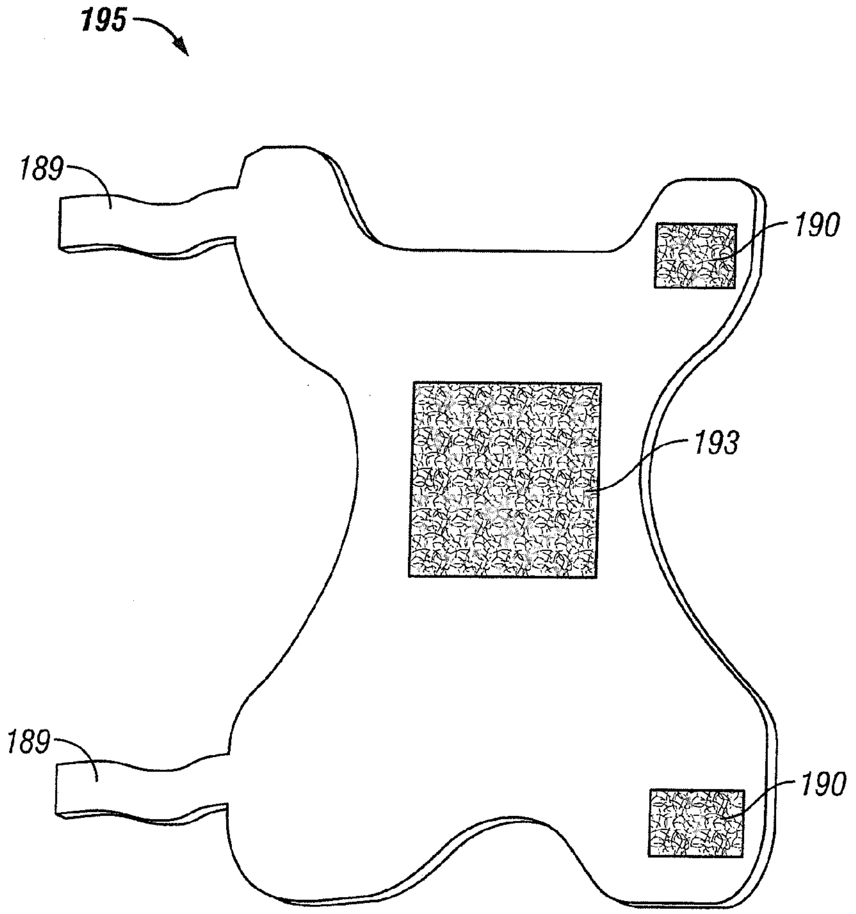
FIG. 1*a* is a top perspective view of one exemplary embodiment of the brace element used in conjunction with the apparatus of FIG. 1.
Figure 1B:
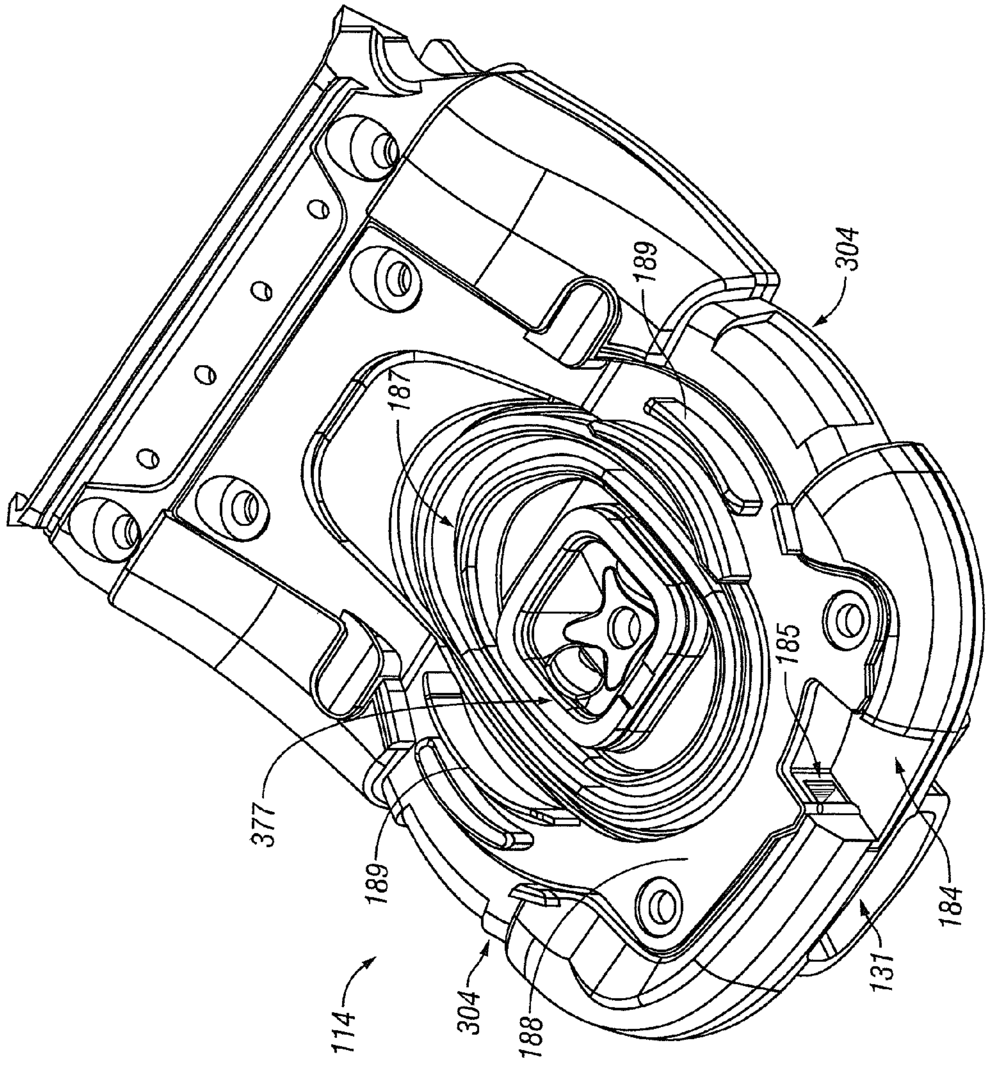
FIG. 1*b* is a bottom perspective view of the interior portion of the apparatus of FIG. 1, showing the actuator and mating surfaces for the support frame.
Figure 1C:
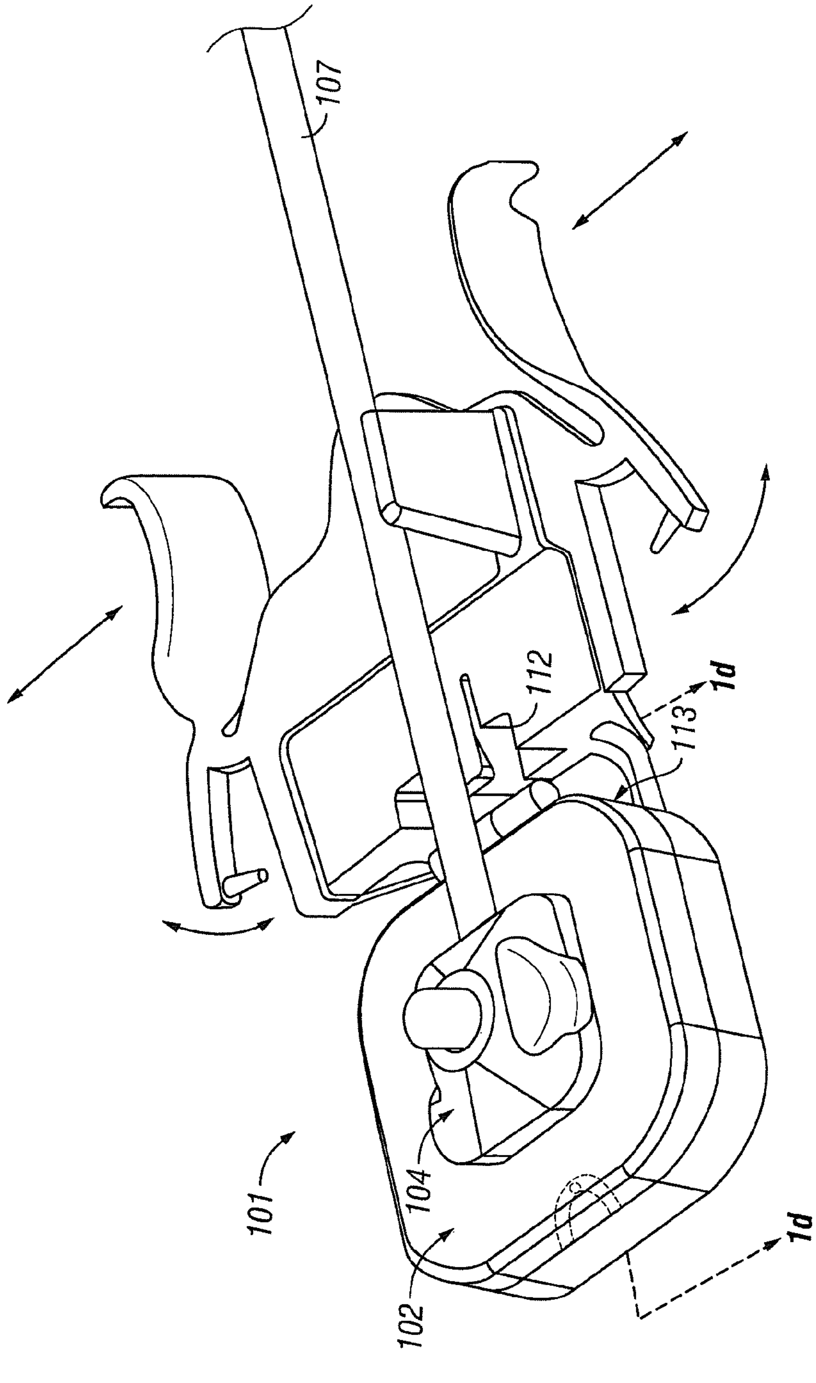
FIG. 1*c* is a top perspective view of one exemplary embodiment of the sensor and paddle assembly of the present invention.
Figure 1D:
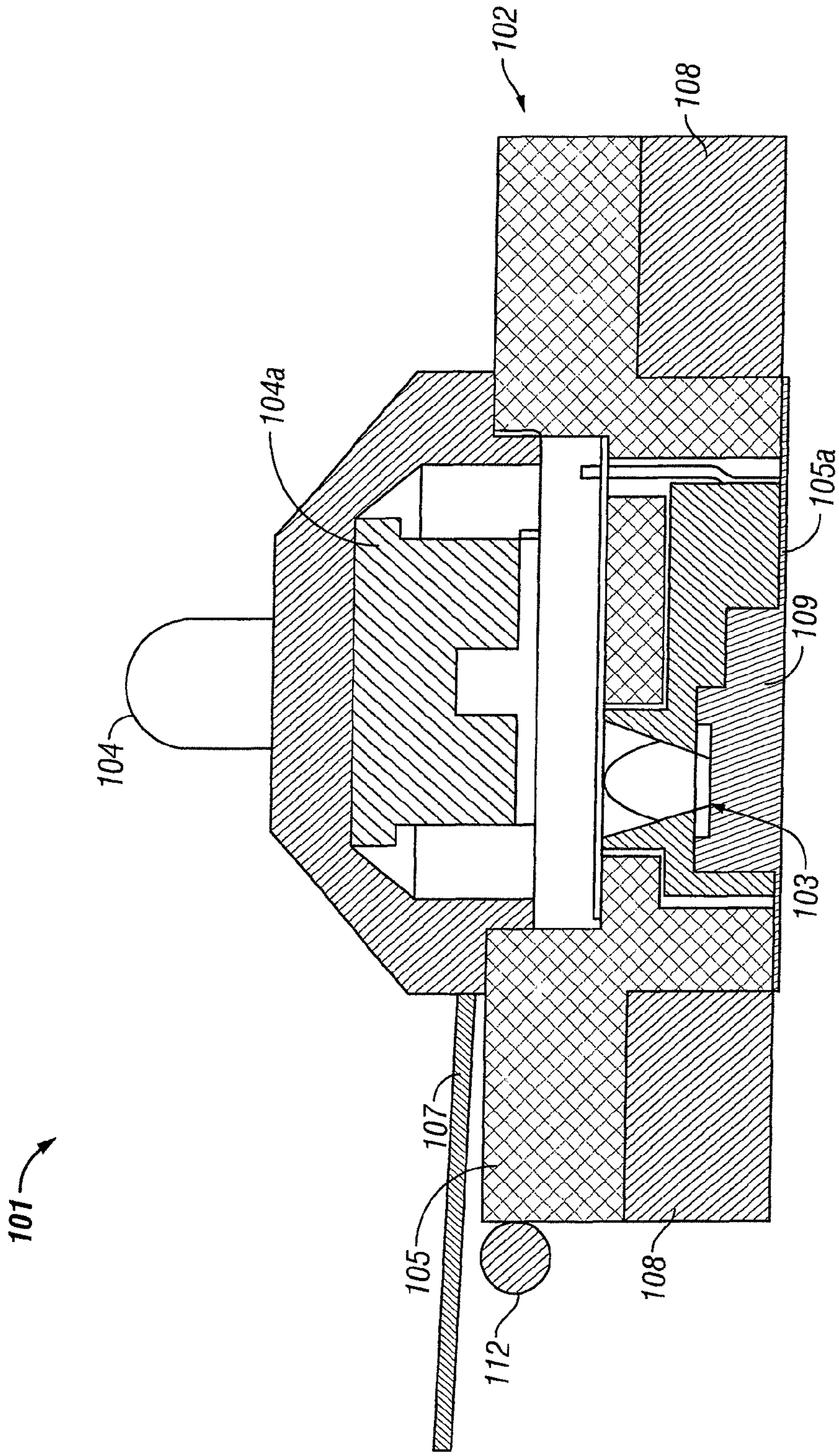
FIG. 1*d* is a cross-sectional view of the sensor assembly of FIG. 1*c*, taken along line 1*d*-1*d*.
Figure 1E:
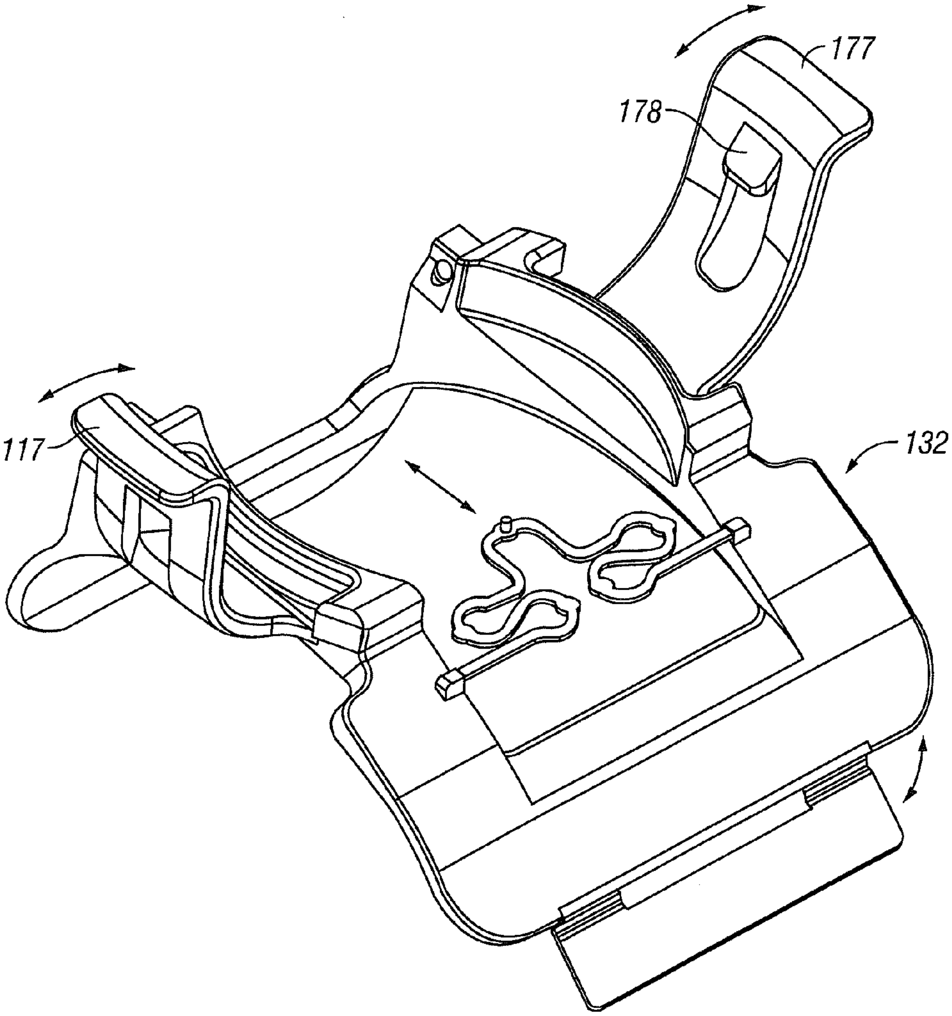
FIG. 1*e* is a perspective view of one exemplary embodiment of the support frame used with the sensor assembly of FIGS. 1*c* and 1*d*.
Figure 1F:
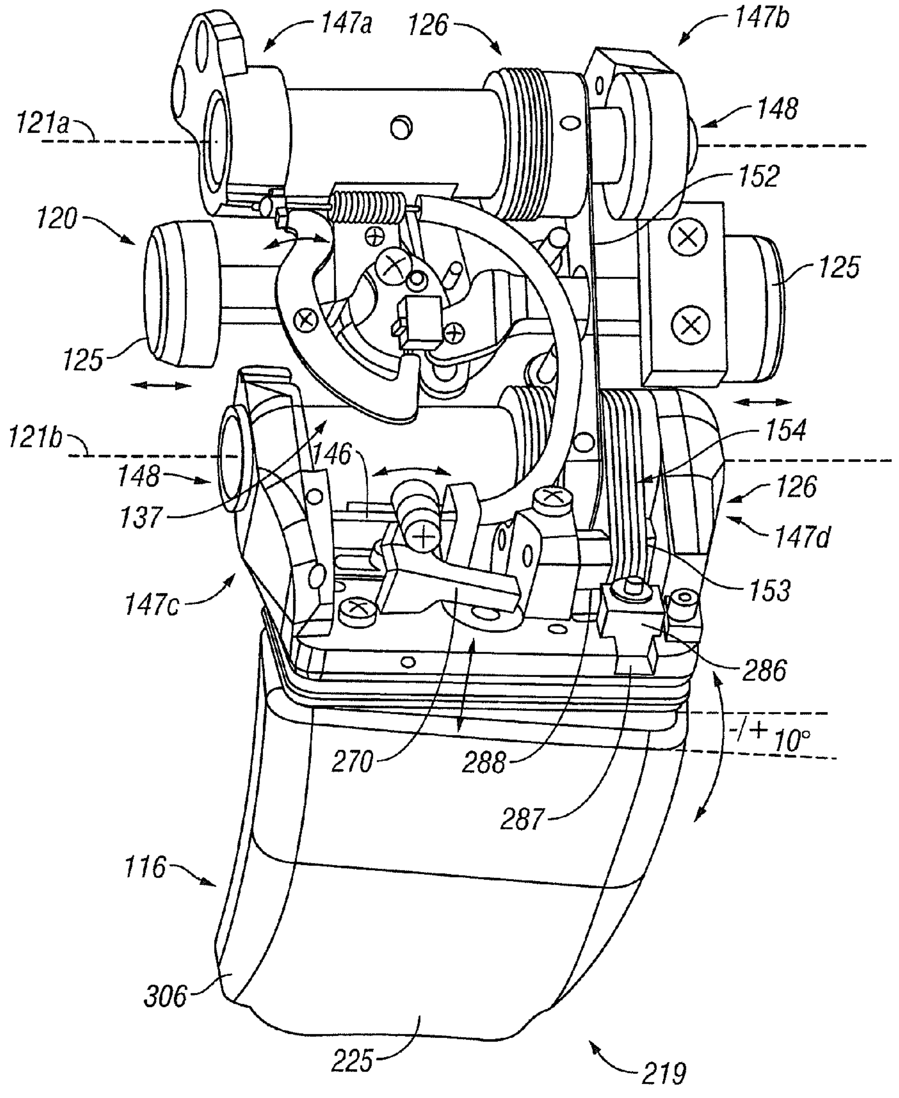
FIG. 1*f* is a perspective view of the apparatus of FIG. 1 shown partially disassembled, illustrating the pivot and trigger mechanisms thereof.
Figure 1G:
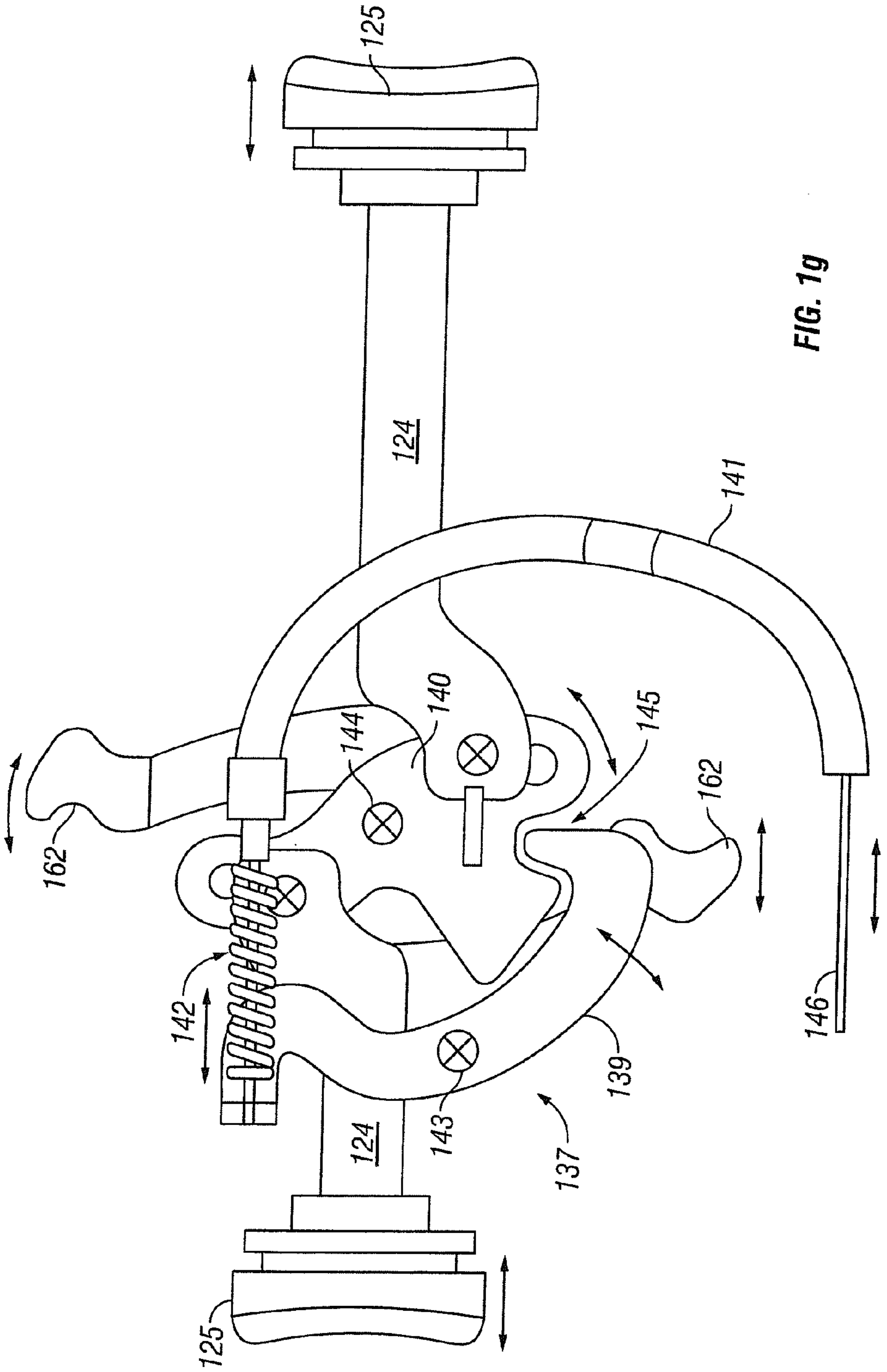
FIG. 1*g* is an elevational view of the trigger mechanism components of the apparatus of FIG. 1*f*.

As illustrated in FIGS. 1*f* and 1*g*, the cocking and trigger mechanism 137 comprises a number of related components including a trigger arm 139, central pivot element 140, actuator cable 141, and bias element (e.g., spring) 142. As best shown in FIG. 1*g*, the central pivot element rotates around a pivot 144, and is slidably coupled to both of the actuator rods 124 such that when the buttons 125 are pushed inward, the pivot element 140 rotates around the axis 144. The pivot element 140 also includes an eccentric region 145 which interacts with the distal portion of the trigger arm 139. Specifically, in the "cocked" condition (shown in FIG. 1*g*), the distal portion of the arm 139 is received within the eccentric region 145, (which corresponds with the distal end 146 of the cable 141 being withdrawn as the trigger arm rotates around its axis 143 under force of the spring 142. The interaction of the trigger arm 139 and pivot element 140 also keeps the actuator rods 124 and hence buttons 125 in a retracted or "pressed in" position until the trigger mechanism 137 is actuated. As described in further detail subsequently herein, the preload mechanism of the apparatus 110 pulls on the distal end 146 of the cable 141, thereby rotating the trigger arm 139 around its pivot, and retracting the distal end of the trigger arm 139 out of the eccentric region 145. This retraction allows the pivot element 140 to rotate counterclockwise (under bias from the eccentric arms 162, discussed below), thereby popping the two actuator rods 124 and buttons 125 outward. This rotation of the pivot element also disposes the distal portion of the arm 139 to ride on the outer periphery of the pivot element 140, until such time as the buttons 125 are again depressed.

Hence, the cocking mechanism 137 acts as a coarse force sensor, locking the rotational portion of the anterior element 116 when the apparatus 110 is sufficiently compressed onto the subject's wrist. This force-based approach takes any guess-work out of establishing the desired level of preload before measurement of the hemodynamic parameters of interest via the sensor element 102, and allows for proper adjustment of the apparatus 110 on subjects of varying size and tissue compliance.

In another embodiment, an electromechanical force sensor of the type well known in the art is disposed within the interior regions of the interior/anterior elements 114, 116 such that either an optical element (e.g., LED or incandescent light), audible element (relay, buzzer, beeper, etc.), or other indication is generated electrically upon application of the desired force to the sensor. The sensor may be a discrete device having no other function but the aforementioned compression or preload sensing, or alternatively may be integrated with other components of the apparatus 110, such as the exemplary strain beam actuator sensor described subsequently herein.

In yet another embodiment, the adjustment process is based on position or proximity of one or more components of the apparatus 110 to other components thereof, or to one or more features of the subject's anatomy. For example, in one variant, occlusion of an optical pathway between an emitter (e.g., diode) and receiver by tissue is used to signal when the apparatus 110 is properly fitted and adjusted. As is well known, the application of compressive force to the tissues of the wrist (or other limb) will cause some degree of distension thereof, such distension being measurable and predictable. Yet other mechanisms may be used, including ultrasonics (such as where sufficient acoustic return is correlated to a desired degree of coupling between an ultrasonic transducer and the subject's tissue), capacitance (e.g., achieving a given capacitance indicates sufficient coupling), inductance, thermal profile, or even electro-optical sensing (e.g., where sufficient reduction in the level of incident visible or IR energy corresponds to occlusion of the sensor during compression of the relevant tissue). Myriad different mechanisms may be used alone or in combination consistent with the present invention, all such mechanisms being readily employed by those of ordinary skill provided the instant disclosure.

In the illustrated embodiment, the bracelet interior and anterior elements 114, 116 each comprise a plurality of different components. The interior element 114 includes the sensor actuator mechanism 106, a plurality of status indicators (e.g., LEDs) to assist in operation of the apparatus 100, as well as a data interface 131 (FIGS. 3*a*-3*c*) to permit signal transmission to and from the apparatus 110 as required. It will be recognized that while the exemplary embodiments are described in terms of a wired electrical interface (including optionally one compliant with RS-232, USB/mini-USB, IEEE-1394, or other comparable standard), a wireless interface of the type now ubiquitous in the art may be utilized as well either in place of or in concert with the wired interface. For example, the interface may comprise a Bluetooth, IEEE Std. 802.11a or g, or IrdA compliant interface. Any number of air interfaces and spectral access techniques/protocols may be used, including without limitation narrowband (FDMA), DSSS, TDMA, CSMA/CD, ALOHA, FHSS, OFDM, or even UWB (such as 802.15 DSSS or OFDM, or other ultra-wideband technology). Construction of a suitable wireless interface is well known to those of ordinary skill in the RF and electronic arts, and accordingly is not described further herein.

The aforementioned data interface 131 is also optionally combined with an electrical (power) interface which supplies power to the apparatus 110 for operation of the motor(s) (described below) and any electrical indications or other ancillary functions. Alternatively, the electrical interface can be separated from the data interface, such as via a removable or fixed electrical power cord running between the apparatus and the control module.

As yet another alternative, a battery power supply may be used, such as where the battery(ies) is/are disposed within the unused volume of interior element 114 or anterior element 116 and provide power to the apparatus autonomous of any external supply, thereby providing the device with great mobility. Lithium, NiCd, or similar long-lived batteries may be used in order to extend the operating duration of the apparatus 110.

In yet another embodiment, the battery disposed within the apparatus 110 may be of the rechargeable type, with an inductive charger (e.g., "paddle" or other shape) of the type well known in the art used to provide energy to recharge the battery. In one variant, the recharging element comprises a receptacle or holder into which the apparatus 110 is fitted when not in use. When so fitted, the inductive elements of the charger and apparatus 110 are in substantial proximity to one another, thereby allowing transfer of electrical energy there between via the well known process of electromagnetic induction. Hence, when not in use, the apparatus 110 can simply be placed in its charger/holder, thereby preparing it for subsequent use. Indicator and/or charge level circuitry may also be employed if desired in order to provide the user with an indication of charge progress and battery depletion.

In yet another embodiment, the inductive charger may be contained or built into the substrate (e.g., operating room table) on which the subject is lying, thereby in effect providing battery recharging on a continuous or semi-continuous basis during use. For example, where the surgery is performed such that the subject's arm is disposed laterally outward, the portion of the surgical table which supports the subject's arm can be fitted with an inductive charging/power transfer unit such that when the apparatus 110 is disposed on the subject's wrist, and the wrist disposed on the support portion, the apparatus 110 is in proximity to the inductive charger, thereby permitting energy transfer.

In still another embodiment, a "solar" powered array of the type well known in the electronic arts is provided on e.g., the top or outer surfaces of the body of the bracelet apparatus, thereby allowing at least a portion (up to and including all) power requirements of the apparatus to supported by the array. As used herein, the term "solar" includes literally any frequency of electromagnetic radiation in the visible or near-visible regions, and is in no way limited to naturally generated solar radiation. This is especially significant since the primary uses of the bracelet apparatus are indoors, where natural solar radiation levels are quite low compared to wavelengths generated by incandescent, fluorescent or other sources of light. In one exemplary embodiment, the array includes a plurality of Zener diodes connected to a battery system, wherein when forward biased due to the voltage output of the solar cells of the array, the battery is charged, and this potential can then be drawn off as needed by other components of the apparatus. Myriad other solar cell configurations are well known in the art, and may be used consistent with the invention in order to afford, inter alia, increased mobility and operational simplicity, and/or reduced weight and electrical (e.g., power supply) cabling.

In operation, the present embodiment of the bracelet 110 of the invention also optionally notifies the user/operator of the presence of the sensor assembly 101 (as well as the status of its coupling to the actuator and the sufficiency of electrical tests of the sensor assembly 101) through an integrated indication. Specifically, the interior element 114 of the present embodiment includes a multi-color indicator light array 181 (in the form of a series of light-emitting diodes 182) disposed on its outer surface; see FIG. 1 and FIG. 3*a*. This array 181 is electrically coupled to a phototransistor 185 (FIG. 1*b*) which determines the presence or lack of presence of the sensor assembly 101 (specifically, the sensor paddle described in, inter alia, co-pending application Ser. No. 10/920,999 filed Aug. 17, 2004 previously incorporated herein) when the paddle is received within a sensing cavity 184 (FIG. 1*b*) and all electrical connections are made. Specifically, the presence of the sensor assembly 101 is detected by a sensing feature (e.g., raised vertical tab) disposed atop the paddle. In the present embodiment, the LED array 181 glows yellow upon insertion of a sensor connector into the actuator 106. The system logic (e.g., software programming) then looks for the paddle (tab) by determining if a phototransistor has a blocked optical transmission path by virtue of the paddle tab being disposed into the cavity 184, thereby indicating that it is a "new" non-calibrated sensor. Specifically, calibrated sensors will have their paddle removed, thereby allowing for optical transmission across the phototransistor 185. If a new sensor assembly is detected, the system then "zeroes" the sensor by balancing the sensor bridge circuit and activating the LED array 181 in a selected color (e.g. green), signaling the user to remove the paddle 133 (FIG. 1*c*). In the illustrated embodiment, the apparatus can only be calibrated with the paddle in place, since the latter protects the active area at the bottom of the sensor from any loads which might affect the calibration. In addition, an EEPROM associated with the sensor assembly 101 is written with the required data to balance the sensor bridge circuit in that particular sensor. Exemplary EEPROM and sensor calibration apparatus and methods are described in co-owned U.S. Pat. No. 6,676,600 to Conero, et al. issued Jan. 13, 2004 and entitled "Smart physiologic parameter sensor and method" incorporated herein by reference in its entirety.

If the installed sensor has been used before, but an intervening event has occurred (e.g., the patient has been moved), the paddle will no longer be in place. In this case, the LED array 181 glows a different color (e.g., yellow) and upon insertion, the system logic would determine that the paddle is not in place. The system then reads the EEPROM for the bridge circuit balancing data (previously uploaded at initial sensor use), and balances the bridge offsets. The LED array 181 is then energized to glow green. However, if the system does not detect an installed paddle and cannot read the calibration data in the EEPROM, the LED array will remain yellow and an error message will optionally be displayed prompting the operator to remove the sensor assembly 101.

It will be recognized that other techniques for determining the presence of the sensor assembly 101 and/or paddle may be used consistent with the invention, including mechanical switches, magnets, Hall effect sensor, infra-red, laser diodes, etc.

Additionally, other indication schemes well known to those of ordinary skill in the electronic arts may be used, including for example one or more single color LED which blinks at varying periods (including no blinking) to indicate the presence or status of the components, such as by using varying blink patters, sequences, and periods as error codes which the operator can use to diagnose problems, multiple LEDs, light pipes. LCD or TFT indicators, etc. The illustrated arrangement, however, has the advantages of low cost and simplicity of operator use, since the user simply waits for the green light to remove the paddle and commence measurement. Furthermore, if the red light stays illuminated, the user is alerted that a malfunction of one or more components has occurred.

Figure 5:
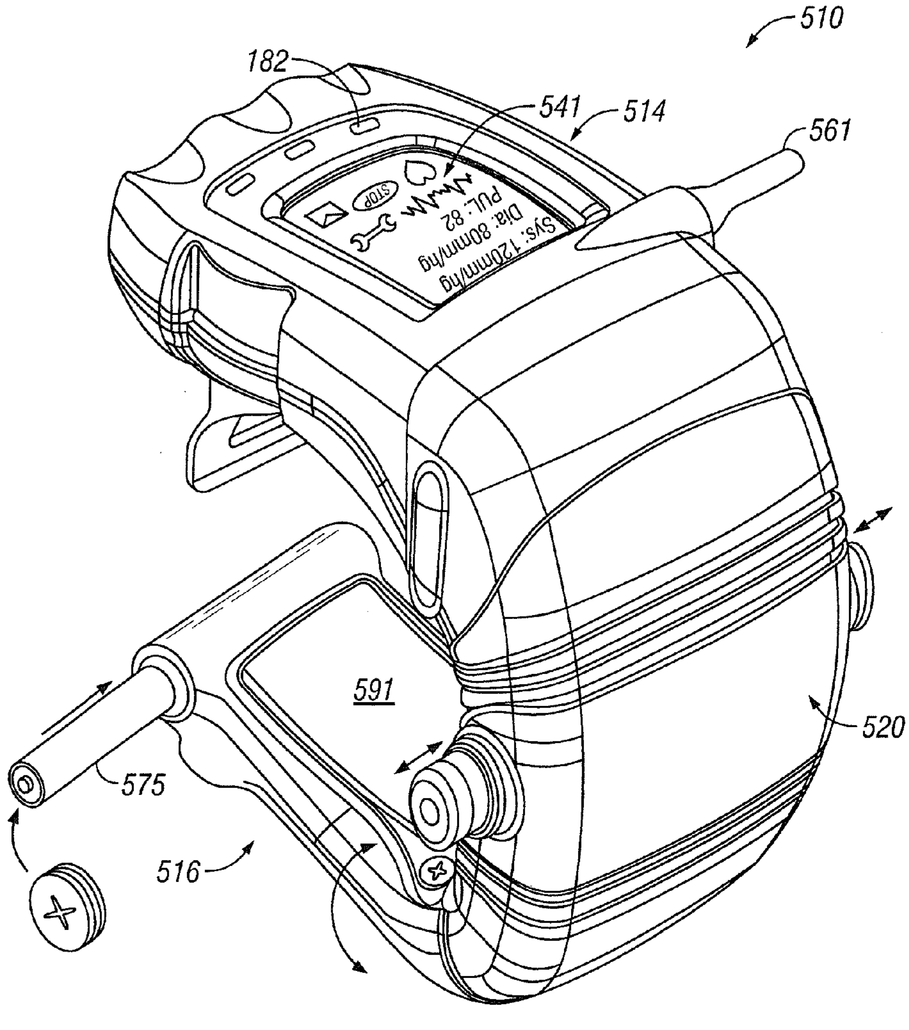
FIGS. 5 and 5*a* illustrate an alternate ("stand-alone") embodiment of the hemodynamic assessment apparatus of the present invention.

The bracelet apparatus 110 may also be used with or include the "universal" interface circuit described in Assignee's co-pending U.S. patent application Ser. No. 10/060,646 filed Jan. 30, 2002 and entitled "Apparatus and Method for Interfacing Time-Variant Signals", which is also incorporated herein by reference in its entirety. Such interface circuitry advantageously permits the hemodynamic assessment apparatus 100 of the present invention to interface with most any type of parent monitor, thereby allowing for greater operational flexibility. It will be recognized that use of the aforementioned universal interface circuit (which may be disposed entirely in the parent monitoring system, or alternatively within the bracelet 110 itself when the autonomous or semi-autonomous variants of the bracelet described subsequently herein with respect to FIG. 5 are used) advantageously extends the flexibility and scope of utility of the invention. Specifically, the universal interface circuit allows calibration (e.g., re-zeroing) of the external monitoring system without having to calibrate (re-zero) the sensor, or even know its zero value. This is to be distinguished with respect to prior art disposable pressure transducer (DPT) systems, which require calibration or re-zeroing of both the monitor and the sensor before each use. Thus, once the sensor of the present embodiment is initially zeroed, it can be interfaced to any actuator, parent monitoring system, or external patient monitor (via the universal interface circuit) without having to remove the sensor from the patient's wrist (or re-insert the paddle 133). This feature advantageously allows the caregiver to move the patient with the sensor (and brace/actuator) attached to another physical location having the same or different parent monitoring system, without obtaining any additional information regarding the sensor zero value. Thus, use of the universal interface circuit in conjunction with the apparatus 110 of the present invention effectively decouples the sensor assembly 101 from the parent system/monitor and provides the equivalent of "plug and play" capability for the sensor.

As best shown in FIGS. 1, 1*b*, 1*f* and 3*a*-3*b*, the interior and anterior elements 114, 116 and pivot mechanism 120 are covered by an interlocking set of protective or environmental covers 306, which act to, inter alia, (i) protect the various internal components of the apparatus 110 from external mechanical, chemical, and electrical influences; (ii) protect users from being pinched or caught on the various internal mechanisms; (iii) provide a more aesthetic external appearance; (iv) provide broader and more comfortable load surfaces over which the various forces generated by the apparatus can be distributed onto the subject's anatomy; (v) provide electrical insulation of the subject and caregiver(s) from the internal voltages associated with the various electrical components (such as the motors 332, 334, circuit board 313, etc described subsequently herein); (vi) provide the user/caregiver with an easily grasped set of surfaces by which they can manipulate the apparatus 110 as desired, and (vii) allow relative movement of the various components of the apparatus 110 while still meeting the foregoing objectives and requirements.

In the illustrated embodiment, these covers 306 are comprised of a molded lightweight polymer such as ABS. Small machine screws of the type known in the art are used to bind many of these cover components to one another and the various structural components 120, 302, 208, although it will be appreciated that other fastening schemes including, e.g., fastener-less "snap fit" and adhesives may be used in place of, or in combination with, the fastener-based arrangement shown.

The covers 306 also comprise one or more flexible bellows or "boot" elements 366 (see FIG. 1) formed from a flexible polymer (e.g., elastomer such as Silicone rubber or Urethane rubber, which is ideally chosen to also be skin-compatible) which provide each of the aforementioned functions yet are sufficiently flexible to permit relative motion of the interior and anterior elements 114, 116 with respect to the pivot mechanism 120. Such bellows or boot elements may also be used if desired at the interface between the distal portion of the anterior element 116 and the pivot mechanism 120, since the former rotates around an axis relative to the latter (e.g. +/−10 degrees) until being locked by the trigger mechanism 137 and associated components.

The interface between the anterior element 116 and the pivot mechanism 120 also optionally comprises two foam "O-rings" which seat over both the anterior pivot 206 and over the slot through which the rod 282 of the locking mechanism (described below) moves.

Furthermore, one or more finger grooves (not shown) can be disposed within the outer surface of the interior and/or anterior element coverings if desired so as to make the apparatus 110 as ergonomic and intuitive to use as possible.

Brace Element—

Referring now to FIG. 1*a*, one exemplary embodiment of the brace element 195 is described in detail. As shown in the Figure, the brace element 195 comprises a foam rubber or similar material formed approximately ⅛ to 3/16 inch thick, depending on material density, so as to be flexible enough to be wrapped around the limb of interest (e.g., forearm) of the subject to be monitored, yet sufficiently non-compliant so as to dissipate the reaction force generated by the bracelet apparatus 110 during fitting and operation. In one variant, the brace 195 includes one or more Velcro patches 193 disposed on its exterior surface (i.e., that facing away from the subject's skin) which cooperate with the Velcro patch 191 of the anterior element 116 (FIG. 1) to provide a stable yet moveable interface between the two components, as described in greater detail below. The patch 193 is made large enough such that precise placement of the anterior element 116 is not required; i.e., a "natural" placement can be used, with the patches 191, 193 being large enough to accommodate a wide range of different positions as may be required.

The illustrated embodiment includes molded-in retaining straps 189 with corresponding Velcro patches 190 on the brace 195 which allow the brace 195 to be removably affixed to the subject, although it will be recognized that other schemes (such as elastomeric bands, snaps, or even adhesives) may be used. Also, the brace may be formed such that no straps are required; i.e., with sufficient width such that the edges of the brace can overlap one another, where they may be affixed to one another with e.g., Velcro or a similar mechanism.

The illustrated embodiment of the brace 195 is also optionally made disposable, thereby enhancing the maintenance of a sterile field during surgery and the like. Advantageously, this disposability is facilitated by the choice of materials and design of the brace of FIG. 1*a*, specifically the use of a low-cost foam polymer and integral straps which can be fabricated at extremely low cost. Even when the brace 195 is configured to include the Velcro patch(es) 193, the cost of manufacture is extremely low. However, this design also provides the necessary degree of rigidity and support for the bracelet apparatus, and also allows one size of the brace 195 to accommodate a variety of different physiologic shapes and sizes. Furthermore, the disposability of the illustrated embodiment of the brace 195 allows for the brace to move with a given patient or subject, such as where the subject moves from one hospital ward to another.

As referenced above, the brace also cooperates with the rotatable distal portion of the anterior element 116 in this regard. Specifically, since the degree of curvature or taper of the forearm region of different individuals will vary substantially, a fixed anterior element configuration for the bracelet 110 would cause varying degrees of pitch of the apparatus 110 (and most importantly the actuator mechanism 106). This pitch can result in some degree of error in the hemodynamic waveform measurement if severe enough. Accordingly, through use of (i) a pitch-variable anterior element configuration (see FIG. 2*a*, et seq.), and (ii) an adjustable pivot or fulcrum (i.e., attachment point between the brace 195 and anterior element pad 191), literally any size and shape of limb can be accommodated by the apparatus 110 without deleteriously pitching the sensor or actuator out of the vertical (normal) plane with respect to the blood vessel of interest.

The brace 195 can also incorporate other optional features as desired, such as for example perforations or holes to permit heat and moisture to diffuse from the subject's skin, instrumentation (e.g., temperature or pressure sensors, or bioelectrical leads), impregnated substances (e.g., powder, lubricants, anti-bacterial agents), and the like.

It will be realized that while a substantially flexible and even disposable brace is described herein, other types of brace structures may also be used. For example, a harder plastic or rubber brace could be used. As another alternative, the brace may simply comprise a wrist band or even surface-applied patch; i.e., one disposed immediately under the anterior patch 191. For example, a rectangular (e.g., 2×4 in.) patch having an easily removable adhesive on one side and the Velcro patch 193 on the other could be used. They key attributes of any such alternatives are (i) dissipation or spreading of reaction force from the patch 193 or other interface, and (ii) flexibility or variability of position so as to avoid having to make precise placements of the anterior element 116.

Similarly, interfaces other than Velcro patches may be used, to include mechanical joints such as lightweight polymer ball joints. Myriad different configurations for interfacing the anterior element 116 to the brace 195 or other such structure will be appreciated by those of ordinary skill when provided the present disclosure.

Sensor Assembly

As shown in FIGS. 1*c* and 1*d*, the exemplary sensor assembly 101 generally comprises an applanation element 102, used to compress the tissue generally surrounding the blood vessel of interest under the force of the actuator 106, and to apply force to the blood vessel wall so as to begin to overcome the wall or hoop stress thereof. The sensor assembly 101 also includes coupling mechanism structures 104 adapted to couple the sensor to its parent actuator 106 via an adapter 377 (described in greater detail below with respect to FIGS. 3*a*-3*c*), housing elements 105 and 105*a*, pressure transducer assembly 103 with associated die, electrical interface device 107, interface medium (e.g., silicone or RTV) 109, and contact or bias element 108. A coupling structure 112 disposed on one face 113 of the sensor housing 105 is used to couple the sensor assembly 101 to a support structure (e.g., support "paddle") to position the sensor assembly 101 in a desired location and orientation.

The sensor assembly 101 of the present embodiment is coupled to the support frame 132 (FIG. 1*e*) using a selectively lockable suspension arrangement; i.e., the sensor assembly 101 is loosely coupled and suspended within the frame 132 via the actuator 106 when unlocked, and rigidly coupled in the frame 132 when locked by the paddle. Suspension of the sensor assembly 101 (i.e., the unlocked state) is desirable during use, when the actuator 106 is coupled to the sensor assembly 101, and is controlling its movement. The locked state is desirable, inter alfa, when initially positioning the sensor (and associated support frame 132) on the subject, and when coupling the actuator 106 to the sensor assembly 101.

The construction and operation of the exemplary sensor assembly 101, support frame 132 and paddle referenced above are described in co-owned and co-pending U.S. patent application Ser. No. 10/920,999 filed Aug. 17, 2004 entitled "Apparatus And Methods For Non-Invasively Measuring Hemodynamic Parameters" previously incorporated herein.

It will be appreciated that while the illustrated embodiment(s) of the bracelet apparatus 110 described herein utilize the sensor assembly 101 as the applanation element, other schemes may be used consistent with the invention. For example, an actuator coupled to an applanation element (not shown) which is separate from or otherwise decoupled from the pressure or other sensor may be employed. Hence, the present invention should in no way be considered limited to embodiments wherein the sensor (assembly) also acts as the applanation mechanism. This approach does, however, simplify the associated mechanisms and signal processing considerably.

It will also be recognized that the sensor, applanation element and alignment frame configurations of FIGS. 1*e*-1*e* are merely exemplary, and other sensor configurations (e. g., single or multiple transducer, alone or combined with other types of sensors, and/or using different bias element geometry) and means for aligning the sensor on the subject's anatomy may be used consistent with the present invention.

Furthermore, the use of an electrical interface cord or "pigtail" 107 can be supplemented or replaced with other types of signal interfaces, including a direct electrical connection between the sensor dome 104 and the adapter 377 (such as via contacts or other interfaces disposed on each).

Pivot Mechanism

Referring now to FIGS. 1*f*-1*i*, the construction details of the exemplary pivot element mechanism 120 are described. As shown in FIG. 1*f*, the two axes 121*a*, 121*b* previously described comprise multiple components that cooperate to provide a pivot functionality, including metallic, pivot assemblies 147*a-d* disposed in substantially parallel orientation within a frame element 150. The frame element 150 is formed of, e.g., machined lightweight aluminum alloy, although other materials (including even rigid polymers) may be used with equal success. The lightweight aluminum is chosen for the present embodiment due to low weight and cost, as well as ease of machining. A series of primary friction or "dry" clutch plates 152, part of the clutch mechanism previously referenced, are disposed generally transverse to two shaft assemblies 148 and perforated thereby. These plates 152 are in the present embodiment comprised of a high-grade steel alloy, including optionally a passivating Chromium (Cr) content such as found in stainless steel to resist corrosion. Each plate surface is polished to the desired level in order to afford a high degree (surface area) of contact between adjacent ones of the plates, and allow for unimpeded relative movement when the load is removed. As is well known, multi-plate clutch systems afford the benefit of a high strength along with the aforementioned ease of relative motion when unloaded, due in large part to the fact that the applied stress is distributed across the significant surface area of many plates, thereby limiting the load carried by any given region of any particular plate. In this fashion, when an external force presses the individual plates into direct contact with each other, a rigid plate-to-plate coupling is established, which affords the "locked" state of the mechanism 120 as previously described.

The primary plates 152 are also interleaved with secondary clutch plates 153 (see FIGS. 1*f*, 1*h* and 1*i*), the latter segregating the friction area of the primary plates 152 to the region 154 immediately surrounding the shaft assemblies 148 and providing a mechanical coupling to interior and anterior coupling blocks (not shown) the blocks and secondary plates 153 which both rotate around their respective pivots 147*a*, 147*b* when the mechanism 120 is in the "unlocked" state. The two groups of secondary clutch plates 153 (one for each shaft assembly 148) are captured within their respective blocks 157, 158 such that the friction or lack thereof between the primary and secondary plates lock or unlocks the blocks 157, 158 and their associated anterior and interior element components.

Figure 1H:
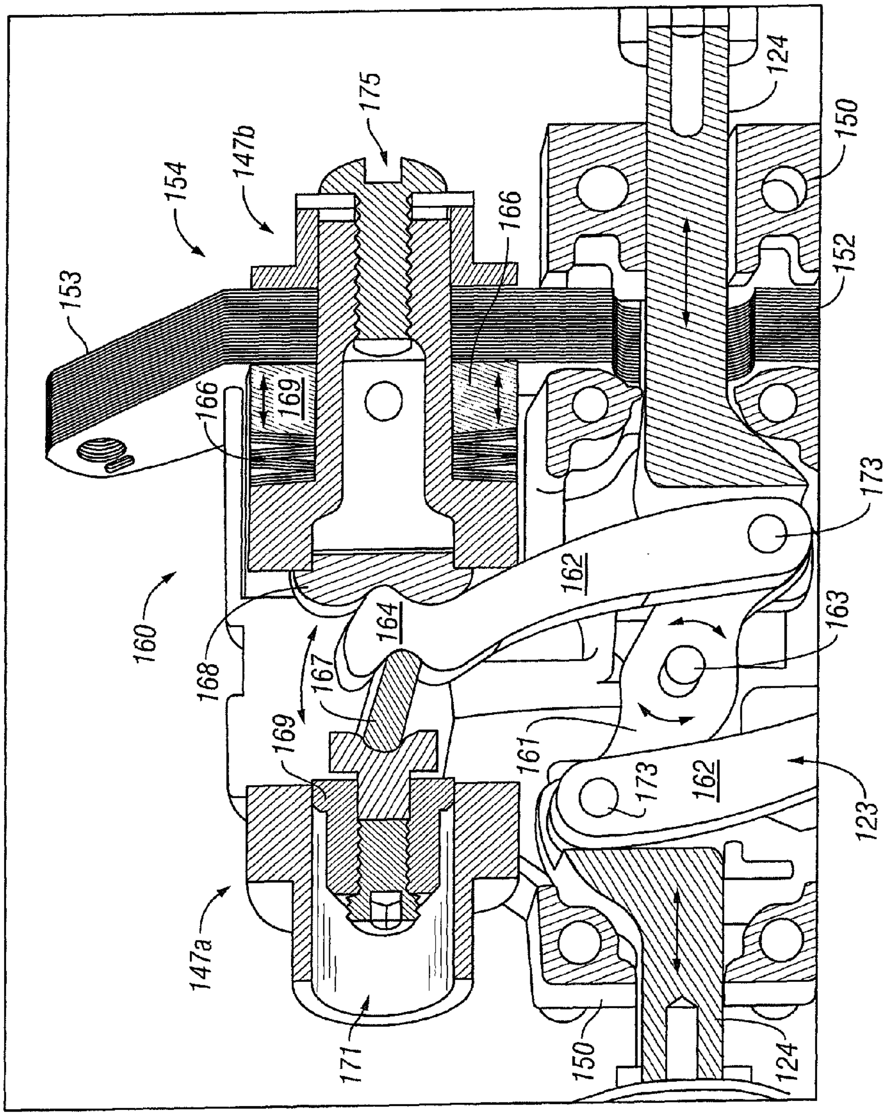
FIG. 1*h* is a partial cross-sectional view of the pivot mechanism of FIG. 1*f*, illustrating the locking mechanism and clutch plate arrangement thereof.

Within the locking mechanism 123, loading of the clutch plates 152, 153 is accomplished in the present embodiment using, inter alia, two compressible load assemblies 160 which are indirectly coupled to the actuator mechanisms and buttons 125 as shown best in FIG. 1*h*. Specifically, the actuator bars 124 contact a central pivot arm 161 and rotationally coupled eccentric arms 162. Upon translation of the actuator bar 124 across its range of motion locked to unlocked, or vice versa), the central pivot 161 rotates around its axis 163, thereby causing the eccentric arms 162 to rotate and their eccentric outer portions 164 to actuate their respective load assemblies 160. Specifically, the shape of each eccentric portion 164 is such that it interacts with a load pin 167 in contact therewith, as well as a contact member 168 of the relevant load assembly 160. The contact member 168 creates a base from which the eccentric portion 164 can "lever" the load pin 167 away (i.e., in the opposite direction). The load pin 167 pushes against the opposite end of the drive shaft 169, which accordingly translates the portion of the drive shaft 169 in communication with the springs 166 (e.g., Bellville washers in the illustrated embodiment) in the same direction, thereby compressing the springs and unloading the clutch plates to some degree. When the springs are sufficiently compressed, the clutch plates 152, 153 are unloaded, thereby allowing relative movement between these plates. The reaction force generated by this transverse force assertion is absorbed by the pivot assembly 147*a* disposed in the frame element 150, via the load pin 167.

Conversely, when the actuator buttons 125 are released, the eccentric arms 162 are rotated around their pivots 173, thereby allowing rotation of their eccentric portions 164, which allows some decompression of the washers 166.

It will be appreciated that other materials and configurations may be used for the clutch plates 152, 153, such as where the primary and secondary plates are made of heterogeneous materials, having varying dimensions, and/or have different coatings on one or more surfaces thereof. Furthermore, individual ones of the primary and/or secondary plates can be specially configured as well to achieve a desired purpose such as greater or lesser friction, longevity, reduced weight, etc. A "wet" plate clutch system may also be substituted for all or a portion of the dry plate system previously described if desired.

Each load assembly 160 is also provided with an adjustment mechanism 175 (e.g., a threaded set screw or comparable) which allows the effective length of that assembly 160 (uncompressed) to be adjusted. As also shown in FIG. 1*h*, the pivot assembly 147*a* includes an adjustment mechanism 171 (e.g., set screw) which allows adjustment of the preload against the load pin 167. This mechanism 171, in conjunction with the mechanism 175 of the load assembly 160, advantageously provides almost complete adjustability for the operation of the locking mechanism. Specifically, in conjunction with other components and adjustments present in the mechanism 120 (such as the shape and dimensions of the eccentric portion 164 of the eccentric arms 162), the designer or user create the desired transition profile; i.e., the required applied force to the actuator bar 124 as a function of its displacement which causes transition from the locked to unlocked states, and vice versa. As will be appreciated, the selection of adjustments, dimensions, and components for the mechanism 120 described herein can produce literally any desired transition profile ranging from, e.g., one that is progressive or "gentle" to one that is effectively binary (e.g., minimal movement of the actuator bars 124 causes a near instantaneous state change).

The foregoing adjustments and component/dimension selections also provide for variation of the allowable range of motion for the interior and anterior elements 114, 116, so as to accommodate different sizes of subjects for monitoring. This permits, inter alia, the manufacture of a "one size fits all" apparatus rather than having to produce multiple different sizes.

In the illustrated embodiment, the load sources 166 comprise a plurality of Bellville washers of the type known in the mechanical arts, although other mechanisms (including helical springs, spring washers, compressive elastomers, etc.) may be used with proper adaptation. Bellville washers (springs) are chosen in the present embodiment based on their significant mechanical advantage (which is advantageously provided over a very limited range of motion, thereby allowing the mechanism 120 to be more spatially compact), ruggedness and high cyclic load or fatigue endurance, and comparatively low weight.

While the foregoing embodiment of the mechanism 120 has great utility, it will be recognized that myriad other configurations and approaches may be readily used consistent with the present invention. For example, the actuator bars 124 and buttons 125 described above may be replaced with a knob or the like which can be rotated through a range of motion, this rotation causing movement of the pivot arm 161 and eccentric arms 162 as previously discussed. Alternatively, a completely "analog" or non-discrete system with a large number of adjustment states may be provided, such as where the aforementioned locking assembly 123 (or other comparable mechanism) is made to be adjustable through a range of frictional levels, thereby allowing the user to specify a desired level of rigidity for the mechanism 120. As another alternative, a toothed washer arrangement may be used, such as where two opposed and complementary finely toothed or splined washer elements are provided to maintain the locked state until a frictional or compressive force applied thereto is reduced such that the washers can move relative to one another.

As yet another alternative, a progressive mechanical arrangement may also be employed; e.g., wherein the movement of the mechanism actuators 124 progressively or even step-wise increases or decreases the applied friction.

As an alternative to the exemplary preload mechanism 203 described elsewhere herein, the pivot mechanism 120 of the present invention may also be practiced using a ratchet-like mechanism of the type known in the mechanical arts, such as e.g., where the closure of the device (i.e., the movement of the two element 114, 116 towards each other so as to bring the apparatus into compression over the subject's anatomy) can occur in small progressive steps of increasing compression, yet release or movement in the opposite direction to expand the apparatus is completely frustrated unless a release mechanism such as a lever or button is actuated. This approach has the advantage of not requiring the user or caregiver to position the apparatus precisely and then actuate the latch mechanism without any further movement; the user can simply open up the gap 117 sufficiently, slide the apparatus onto the wrist of the subject, and then slowly press the two elements 114, 116 toward one another through the range of motion in the ratchet mechanism, thereby progressively tightening the apparatus onto the subject's wrist until the desired level of preload is achieved. The caregiver then simply stops pressing, and the mechanism 120 remains in a static position until the release mechanism (releasing the ratchet) is actuated. Such a capability is especially useful where the caregiver has limited dexterity, such as when the subject themselves is placing the bracelet onto their own wrist, and has only one free hand with which to position the bracelet.

In yet another embodiment, the interior and anterior elements 114, 116 of the apparatus are biased together by the pivot mechanism 120, such that a progressively increasing force is required as the gap 117 is enlarged by the user or caregiver. Hence, in practice, the caregiver will open the gap 117 such as by grasping the interior and anterior elements in their two hands, respectively, and gently pull apart to open the gap 117 sufficiently to place the apparatus onto the subject's wrist. Once this pulling force is released by the caregiver, the bias elements of the mechanism (not shown) which may comprise for example a spring assembly, elastomeric bands or the like, or any other types of mechanisms well known in the mechanical arts, move the two elements 114, 116 back towards one another, until a sufficient reaction force is generated by the compression of the subject's tissue between the two elements 114, 116 (i.e., via the interposed brace element 195 if used, and the sensor support frame 132), at which point mechanical equilibrium is achieved. At this point, a separate latch mechanism (similar to the two-state mechanism described above) can optionally be used to "freeze" the device in place if desired. The bias elements and mechanism may also be adapted such that the level of bias applied at a given relative physical positioning between the two elements 114, 116 can be adjusted to a desired level, thereby allowing for accommodation of the specific physical attributes of different subjects (e.g., larger, smaller, more frail, etc.) and also of the preload placed on the tissue of the subject's arm in the region of the radial artery.

While the foregoing embodiments are described in terms of a manually operated configuration, it will be understood that one or more functions of the mechanism 120 including, e.g., movement of the actuators 124 or similar component, relative movement of the interior and anterior elements 114, 116 relative to the mechanism 120, etc. can be wholly or partially controlled or provided by another external motive force; e.g., an electric motor, electromagnet, pneumatic arrangement, etc. For example, in one variant, an electromagnet or similar arrangement can be used to move the actuator bar 124 upon selection by the user of an electronic "lock/unlock" function, such as via an electrical switch disposed on the bracelet apparatus, or alternatively from an external host, controller or monitor. In another variant, movement of the interior and/or anterior elements 114, 116 is accomplished through a motor driven helical or worm gear arrangement. Numerous other possibilities readily appreciated by those of ordinary skill in the mechanical arts may be used as well.

Anterior Element

Figure 2A:
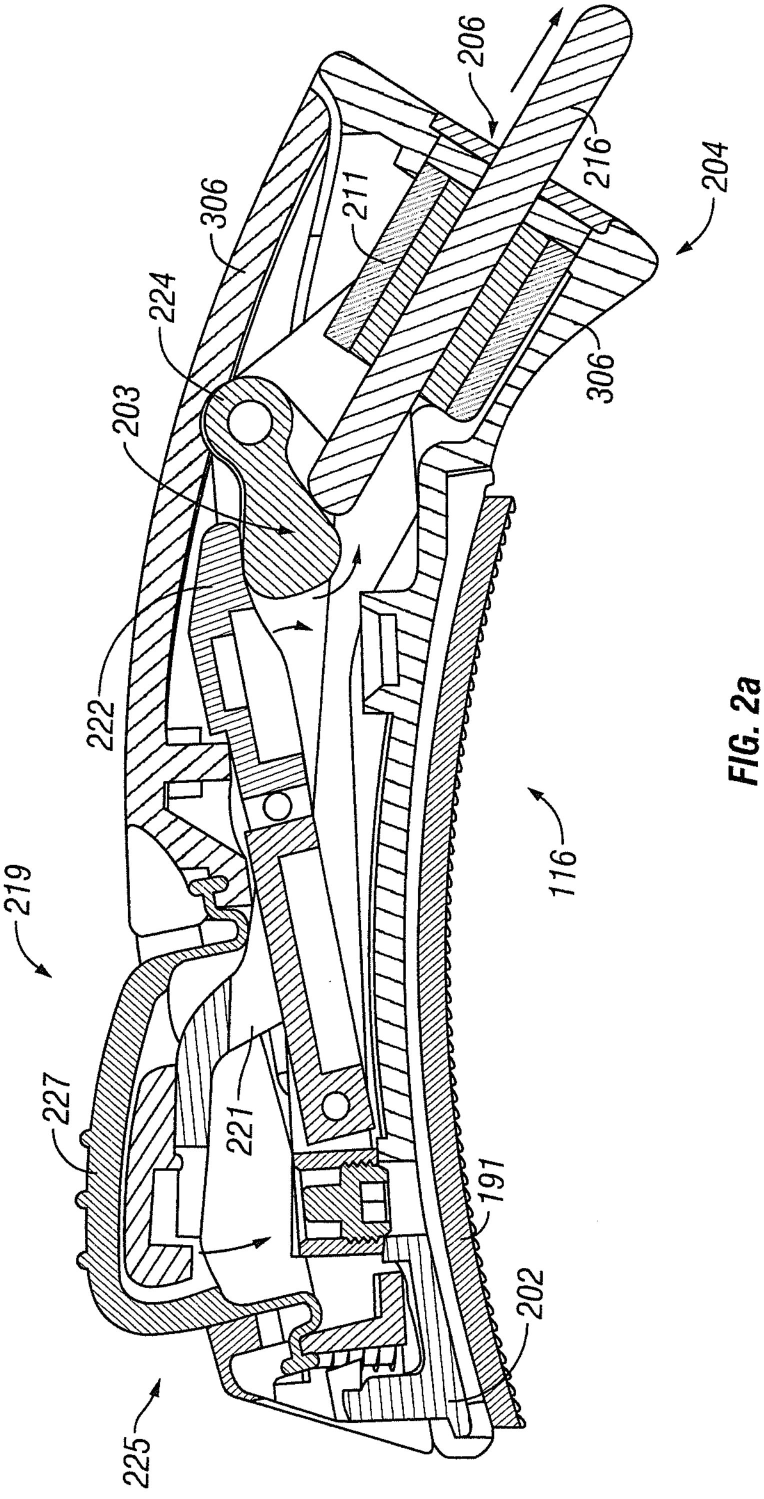
FIG. 2*a* is a cross-sectional view of the anterior element of bracelet apparatus of FIG. 1, showing the various components thereof.
Figure 2B:
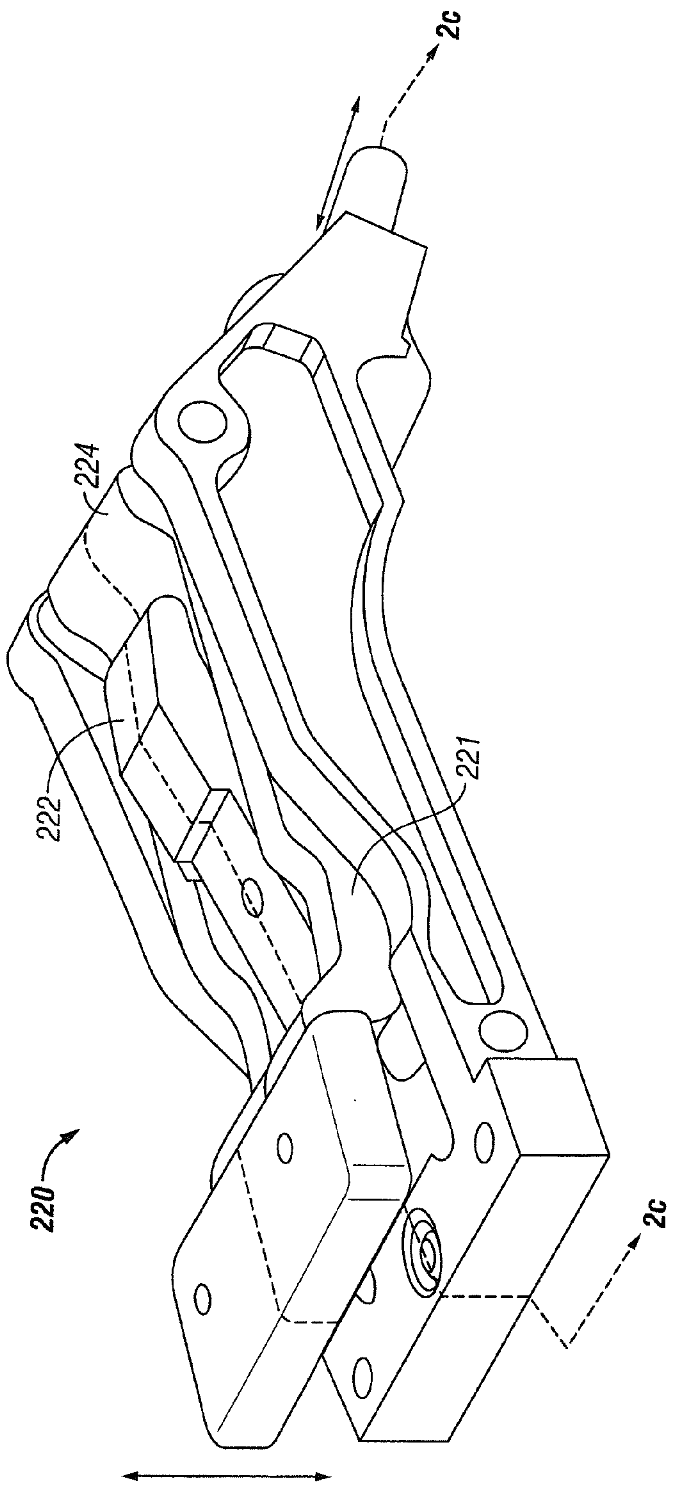
FIG. 2*b* is perspective view of one exemplary embodiment of the preload mechanism apparatus of the anterior element of FIG. 2*a*.
Figure 2C:
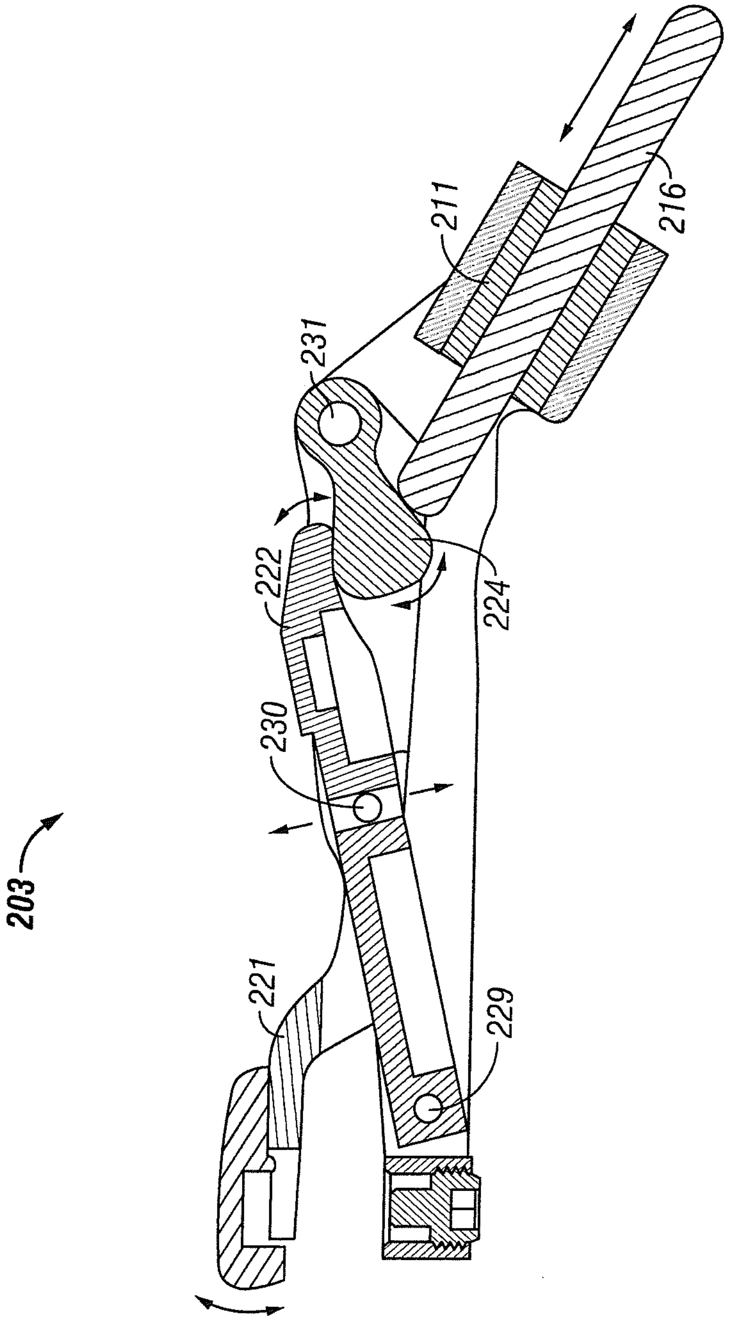
FIG. 2*c* is cross-sectional view of the preload mechanism apparatus of the anterior element of FIG. 2*a*.
Figure 2D:
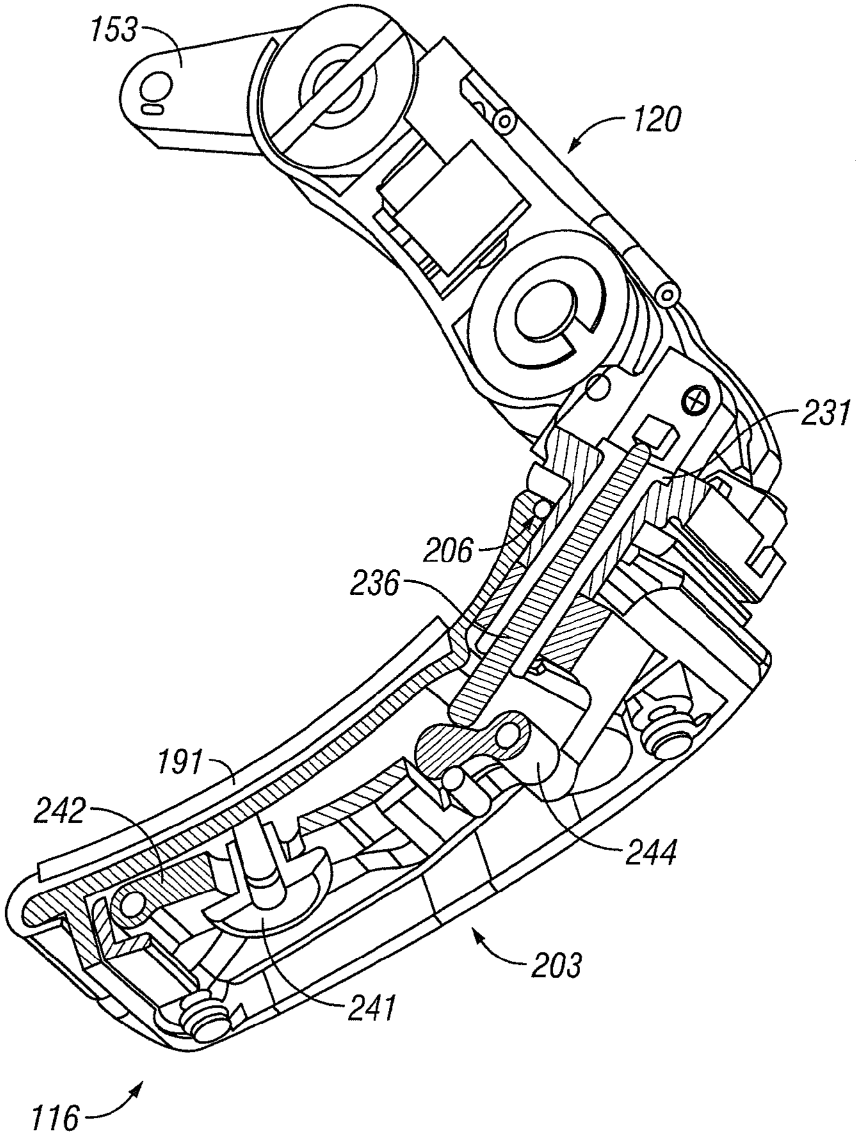
FIG. 2*d* is perspective view of another embodiment of the apparatus of FIG. 1, shown partially disassembled and in section.

Referring now to FIGS. 2*a*-2*c*, a first exemplary embodiment of the anterior element 116 of the bracelet apparatus 110 of FIG. 1 is described in detail. As shown in FIG. 2*a*, the anterior element 116 generally comprises a sub-frame assembly 202 having a preload actuator mechanism 203, mating portion 204, rotation joint 206, and cover elements 306.

The anterior element further comprises a rotation joint 206, which also includes a bushing 211 that acts as a guide for the actuator rod 216 of the preload actuator mechanism 203 (described in greater detail below). The bushing 211 is concentric with the rod 216, thereby allowing the anterior element 116 to rotate around the axis of the bushing 211 (+/−10 degrees in the illustrated embodiment, although these values may be varied as desired, and may even be asymmetric). The central channel formed by the bushing 211 is occupied by the rod 216, which moves longitudinally along its axis within the bushing 211. It will be appreciated that while a substantially straight rod 216 is shown in the illustrated embodiment, other configurations may be used, such as where a curved or bent element (not shown) is used, thereby adding a greater degree of curvature to the anterior element 116.

As will be appreciated, effectively the entire anterior element 116 can rotate with respect to the pivot mechanism 120 (see FIG. 1*f*), yet be maintained as a unitary assembly. This rotation capability advantageously allows the anterior element 116 to self-orient during installation and operation of the bracelet apparatus, and provide the most comfortable fit for the particular features of the subject's anatomy. It also helps accommodate variations in each subject's anatomy and changes in position thereof (such as flexing of the arm, bending at the wrist, etc.) during positioning, while still providing a substantially compliance-free environment for the sensor disposed on the opposite (interior element 114) side of the wrist. Hence, even across significant variations in each different subject's anatomy, a substantially vertical (normal) bias and position is maintained for the sensor assembly 101 and actuator 106, thereby allowing for more consistent and accurate sensor measurements.

In the illustrated embodiment, a standard retaining ring (e.g., C-clip or the like) is clipped into a groove in a tube which rides within the outer bushing 211 of the pivot or rotation joint 206. The bushing 211 and tube are part of the joint 206 disposed in the end of the anterior element 116. The retaining ring is clipped in place onto the tube after it passes through the bushing 211, which stops the tube from backing out of the bushing, yet allows it to rotate. It will be appreciated that other mechanisms for keeping the two components (i.e., anterior element 116 and pivot mechanism 120) in a locked but rotating configuration may be used consistent with the invention.

As discussed above with respect to the trigger mechanism 137, the rotation of the anterior element 116 is frozen or locked when the appropriate level of preload is reached. However, in an alternate embodiment of the invention, the rotation of the anterior element 116 is left unlocked (even during operation) so as to account for variations or movements of the subject even during the measurement process. It will also be appreciated that the anterior element 116 can also be made user-adjustable; i.e., where the user or caregiver is required to affirmatively adjust the element 116 into a desired orientation, and the element 116 remains in that position due to, e.g., friction in the pivot/bushing mechanism 206, 211.

In another embodiment (not shown), the anterior element 116 can be adapted for easy removal from the bracelet 110, such by actuating a local push-button which retracts a spring-loaded ball lock device of the type well known in the mechanical arts, or comparable mechanism. In this fashion, the caregiver or user can readily swap out different configurations of anterior element, such as those adapted for different anatomical sizes or features, different grades of compliance, different padding/covering options, different controller, display, electronics, power supply, communications, etc., packages, and the like.

Combinations of the foregoing may also be utilized, such as where the user must manually position the removable anterior element 116 when unlocked, yet the element 116 locks when the trigger mechanism 137 is actuated as previously described.

As shown best in FIGS. 2*b* and 2*c*, the preload actuator mechanism 203 of the present embodiment includes a series of components which collectively act in a "scissor-like" fashion and allow the user the easily and accurately set the preload of the bracelet apparatus 110 as a whole around the user's wrist or other limb. Specifically, the illustrated embodiment comprises a mechanical linkage 220 actuated by pressure placed on a load lever 221 disposed within the distal portion 219 of the anterior element 116. This linkage 220 comprises a pivoted load arm 222, pivoted load pawl 224, and the aforementioned actuator rod 216. The various pivots 229, 230, 231 of the mechanism 203 provide the aforementioned scissor-like operation. As shown in FIG. 2*a*, the load lever 221 is disposed beneath a protrusion 225 formed in the outer surface of the outer covering 227 of the anterior element 116.

The placement of the load lever 221 under this protrusion 225 is purposeful, in that it provides a shape that a user's fingers naturally grasp. Specifically, the angles, shape and placement of the protrusion 225 is such that a user's fingers naturally use it as the contact point for their fingers, thereby disposing the user's fingers (and hence the application of force) right onto the end portion of the lever 221. This approach advantageously assures that the force of the user's hand is applied to the lever 221, thereby allowing for an accurate determination of preload. For example, were the user's fingers placed more distant from the lever 221, significant additional force (and hence preload) would have to be applied before the bias force of the lever 221 were overcome, and the preload mechanism actuated. Hence, the user would exceed the desired preload potentially by a significant amount, which could cause errors within the subsequent hemodynamic measurement(s).

Not withstanding, a variety of different shapes or configurations can be used to guide or position the user's fingers over the lever 221, such as for example (i) finger grooves or recesses formed within the outer surface of the anterior element, (ii) a temperature sensor connected to an indicator (e.g., LED) such that the LED is illuminated green when the user has their fingers on the desired spot, and so forth. As another alternative, a levered tool (e.g., plastic "pliers", not shown) specifically configured to interface with the interior and anterior element outer surfaces can be used, thereby assuring consistent placement of the biasing (preload) compressive force to the apparatus 110. Other approaches will also be recognized by those of ordinary skill.

As previously discussed, when the bracelet 110 is disposed on the subject's anatomy, the user then establishes the proper preload by, e.g., placing their opposed thumb and forefingers in respective' ones of the recess 180 and protrusion 225 formed on the outer surfaces of the interior and anterior elements 114, 116, and pressing their fingers together. The load level 221 is biased outward (such as via mechanical feedback from the spring 142 of the trigger mechanism 137 through the linkage 220, or via a spring placed under the lever 221 or pivoted load arm 222) and acts like a force sensor of sorts, resisting movement until sufficient load or force is applied to it. As the load lever 221 moves inward under force, it acts against the load arm 222, causing it to rotate around its pivot 230 as shown in FIG. 2*b*. This rotation causes the load pawl 224 to rotate around its pivot 231, thereby acting on the actuator rod 216 and causing it to translate along its longitudinal access within the channel of the bushing 211 as previously described.

This movement of the rod 216 acts against a pivoted trigger pawl 270 which is attached to the distal end 146 of the cable 141 of the trigger mechanism 137 (see FIG. 1*f*). Specifically the rod 216 rotates the pawl 270 and pulls the cable through its (fixed) sheathing, thereby rotating the trigger arm 139 and retracting its distal end from the recess 145 of the pivot element 140 as previously described with respect to FIG. 1*g*. This retraction transitions the trigger mechanism (and pivot mechanism) from the "cocked" state to the "uncocked" state, and thereby locking the pivot assembly 120 in place (as well as preventing further rotation of the anterior element 116 with respect to the pivot assembly 120).

It will be appreciated that the level (and/or profile) of preload necessary to actuate the mechanism 203 (and hence the trigger mechanism 137) can be varied as desired through any number of means, including for example, the use of additional biasing or control mechanisms (e.g., springs, elastomeric inserts, etc.) within the mechanical linkage 220, and/or adjustment of the size and shape of the various linkage components and even the compliance of the outer covering 227 in the region of the protrusion 225. The profile, i.e., amount of force that must be applied as a function of travel of the lever 221 to trigger the mechanisms 203, 137, can also be varied so as to be quite sharp (rapid transition) or more progressive (slower actuation) as desired.

Figure 2E:
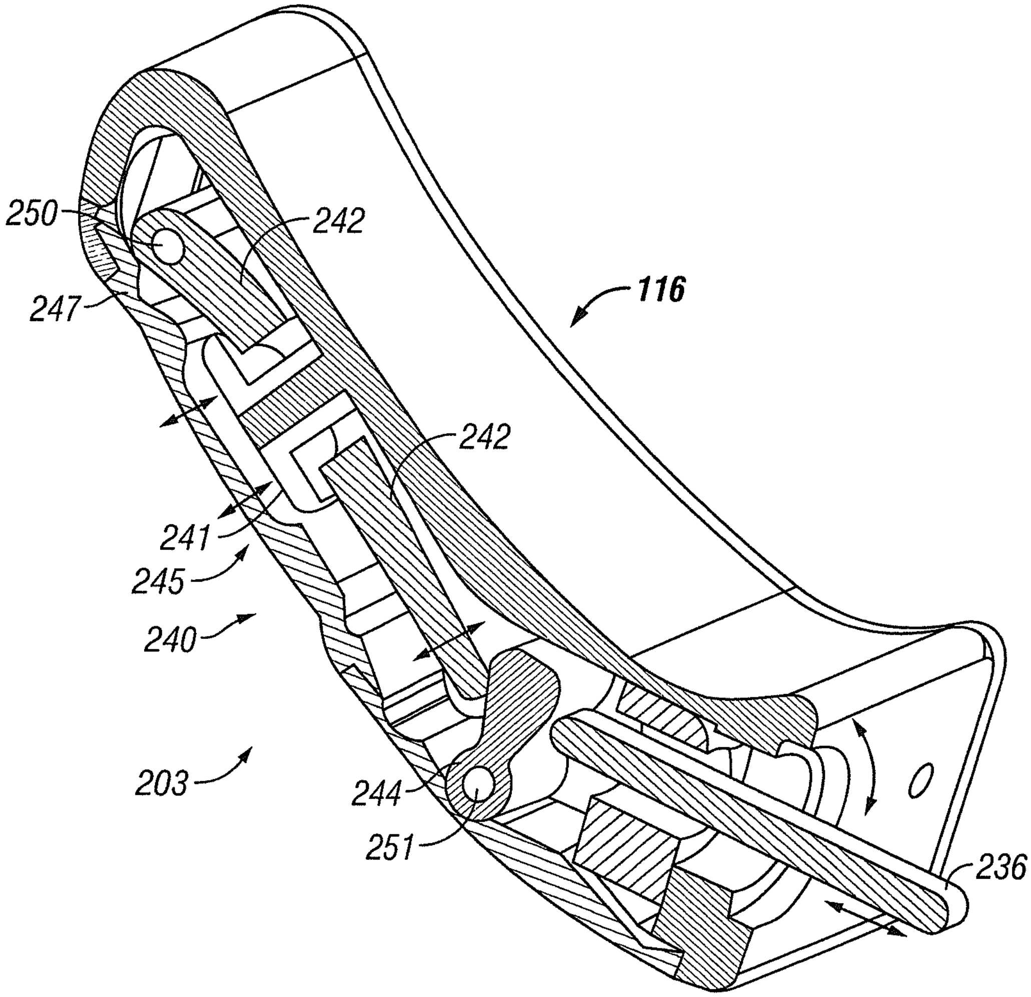
FIG. 2*e* is sectional view of the anterior element of the apparatus of FIG. 2*d*, illustrating the preload mechanism contained therein.
Figure 2F:
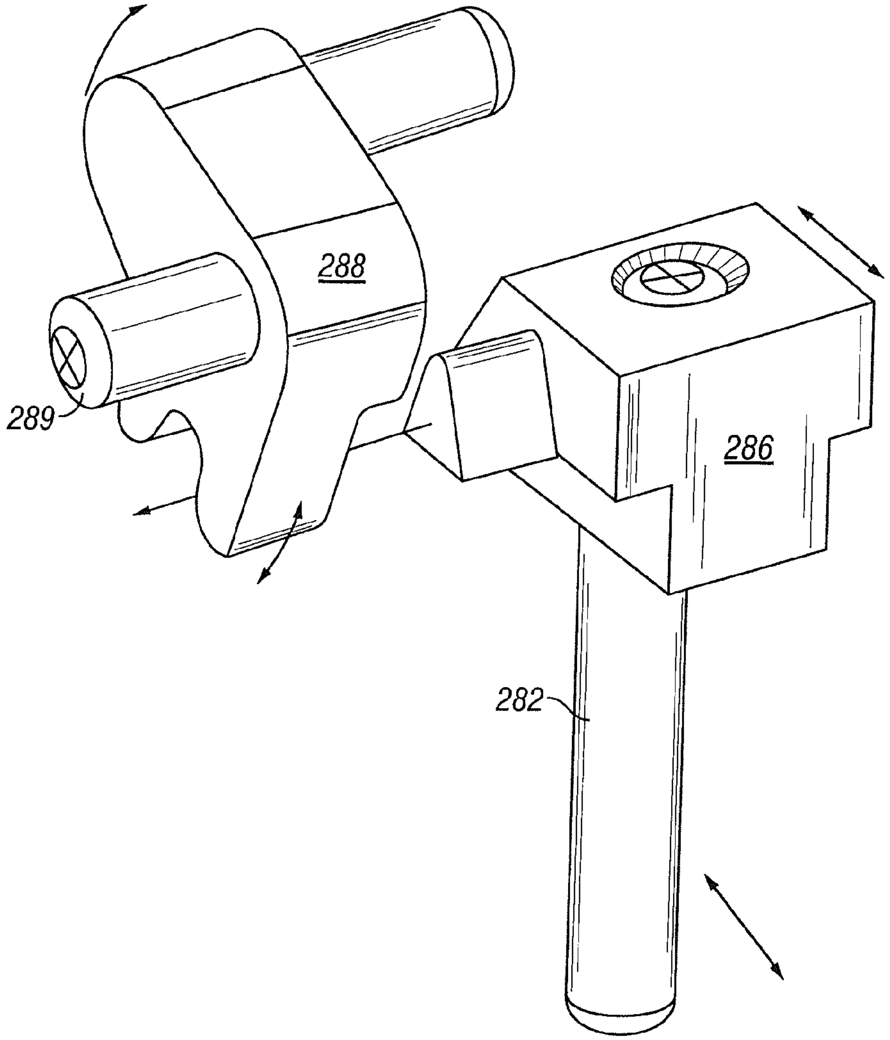
FIG. 2*f* is a perspective exploded view of an exemplary embodiment of the pitch transfer portion of the locking mechanism for the anterior element, showing the traveling block and two-toothed gear.

In another embodiment of the preload mechanism, (FIGS. 2*d* and 2*e*) uses a mechanical linkage 240 actuated by pressure placed on a load button 241 disposed within the anterior element 116. This linkage 240 comprises a pivoted load arm 242, pivoted load pawl 244, and the actuator rod 236. As shown in FIG. 2*e*, the load button 241 is disposed beneath a recess 245 formed in the outer surface of the pliable outer covering 247 of the anterior element 116. When the bracelet 110 is disposed on the subject's anatomy, the user then establishes the proper preload by, e.g., placing their opposed thumb and forefingers in respective ones of the recesses 180, 245 formed on the outer surfaces of the interior and anterior elements 114, 116, and pressing their fingers together. The load button 241 is biased outward (such as via a spring placed concentric to the load button shaft 248 under the button, or alternatively under the pivoted load arm 242) and acts like a force sensor of sorts, resisting movement until sufficient load or force is applied to it. As the load button 241 moves inward under force, it acts against the load arm 242, causing it to rotate around its pivot 250 as shown in FIG. 2*e*. This rotation causes the load pawl 244 to rotate around its pivot 251, thereby acting on the actuator rod 236 and causing it to translate along its longitudinal access within the channel of the bushing 231 as previously described. This movement of the rod 236 triggers the associated mechanism 137 within the pivot assembly 120, effectively transitioning the pivot assembly from the "cocked" state to the "uncocked" state, and thereby locking the pivot assembly 120 in place (as well as preventing further rotation of the anterior element 116 with respect to the pivot assembly 120).

It will be appreciated that any number of schemes can be used to bias the load button 241 so as to establish the desired level of preload, including e.g., springs, compressible yet resilient elastomers, spring washers, etc. Furthermore, the biasing or retarding force can be disposed at various locations throughout the preload mechanism 203, such as under the button 241, under the load ann. 242, against the load pawl 244, concentric with the actuator rod 236, or against the cable pawl 270.

Anterior Element Locking Mechanism

As previously described, the anterior element 116 is allowed to rotate (when unlocked) around its pivot 206 to a certain degree, e.g., +/−10 degrees. The mechanism 280 for locking the anterior element 116 is now described in detail with reference to FIGS. 1*f*, and 2*f*.

Figure 1I:
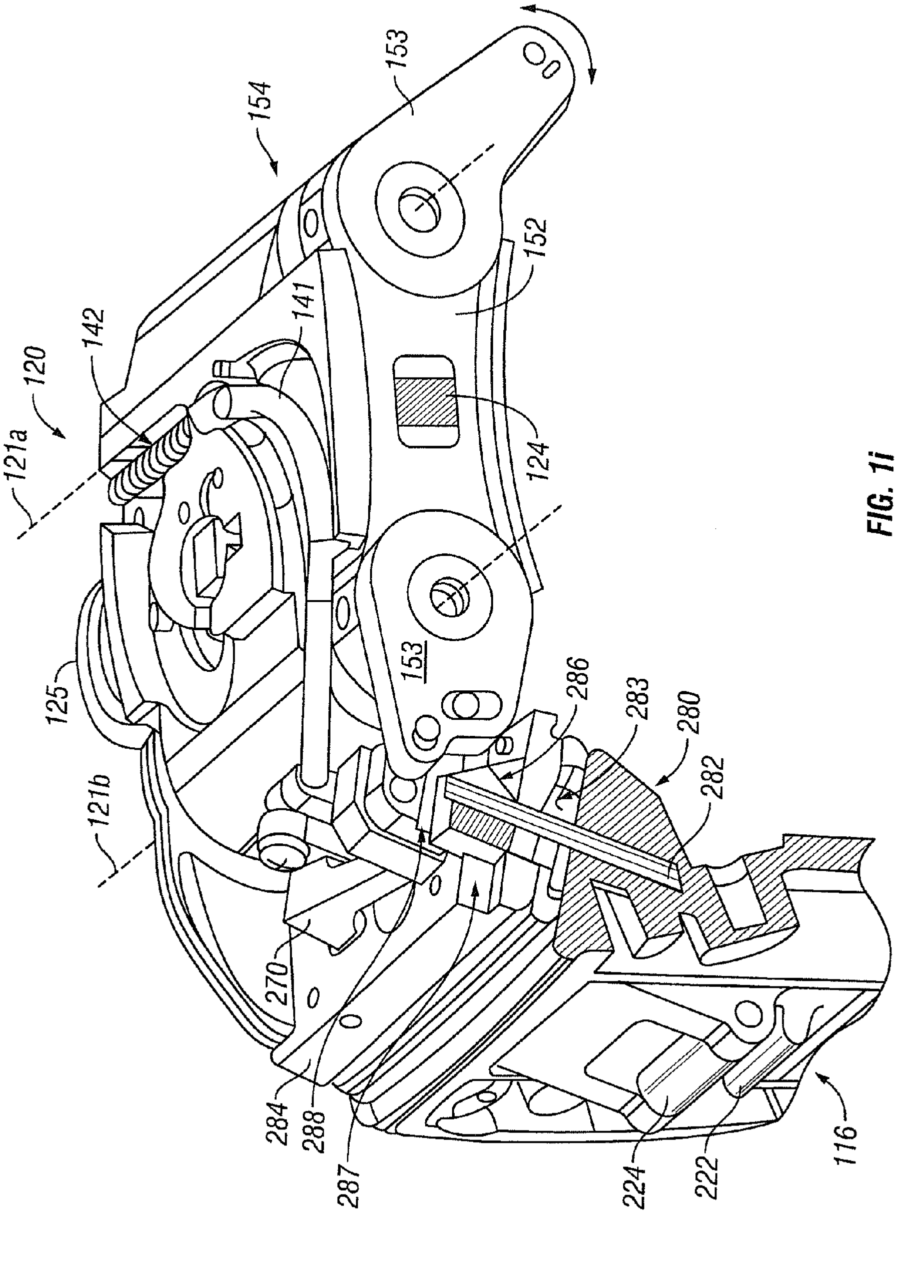
FIG. 1*i* is a perspective view of the apparatus of FIG. 1 shown partially disassembled, illustrating the pivot and trigger mechanisms thereof, and portions of the anterior element pivot and preload mechanisms.

As shown in FIG. 1*i*, the locking mechanism 280 comprises a rod 282 captured within the anterior element 116, yet somewhat free to travel within an elongated slot 283 formed within the anterior mating block 284 of the pivot mechanism 120. As the anterior element 116 rotates around its central pivot 206 (previously described), the captured rod 282 moves within the slot 283 in an arced but generally linear fashion. A traveling block 286 within the pivot mechanism 120 to which the other end of the rod 282 is attached moves along within a complementary channel or groove 287. The block 286 further engages a pivoted two-toothed gear 288 (FIG. 2*f*) which rotates around its pivot point 289 as the block 286 travels in its groove 287. The gear 288 is also coupled to the lower clutch plates 153 of the pivot mechanism 120, such that as the gear 288 rotates, so do at least some of the clutch plates 153 (i.e., with respect to the main clutch plates 152 with which they are interspersed).

When the trigger mechanism 137 is actuated (uncocked), the clutch plates 152, 153 are locked together or frozen in place relative to one another (and the pivot mechanism 120 as a whole), thereby frustrating any rotation of the gear 288 around its pivot. Accordingly, this freezes the traveling block 286 within its channel 287, which also freezes the rod 282 in place relative to the pivot mechanism 120. Accordingly, rotation of the anterior element 116 around its pivot 206 is frustrated, and the anterior element is "locked" in place.

As with the pivot mechanism 120, trigger mechanism 137, and preload mechanism 203, many of the components of the anterior element rotation locking mechanism 280 are fashioned (e.g., machined) from lightweight aluminum alloy such as Aluminum 5052 H-32 alloy, or 606116, or 707516, in order to provide both high strength and light weight at reasonable cost. However, it will be appreciated that other materials such as other metals, polymers, or even composites may be used for one or more of the components of these mechanisms.

Interior Element and Actuator

Referring now to FIGS. 3*a*-3*g*, a first exemplary embodiment of the interior element 114 (including the actuator assembly) of the invention is described in detail. The actuator 106 described herein is designed to provide adjustment or movement of the position of the sensor assembly 101 in both sagittal and lateral (transverse) directions; however, it will be appreciated that it may be modified to provide more or less degrees of freedom (including, for example, distal-proximal adjustment). Hence, the following embodiments are merely exemplary in nature.

Figure 3A:
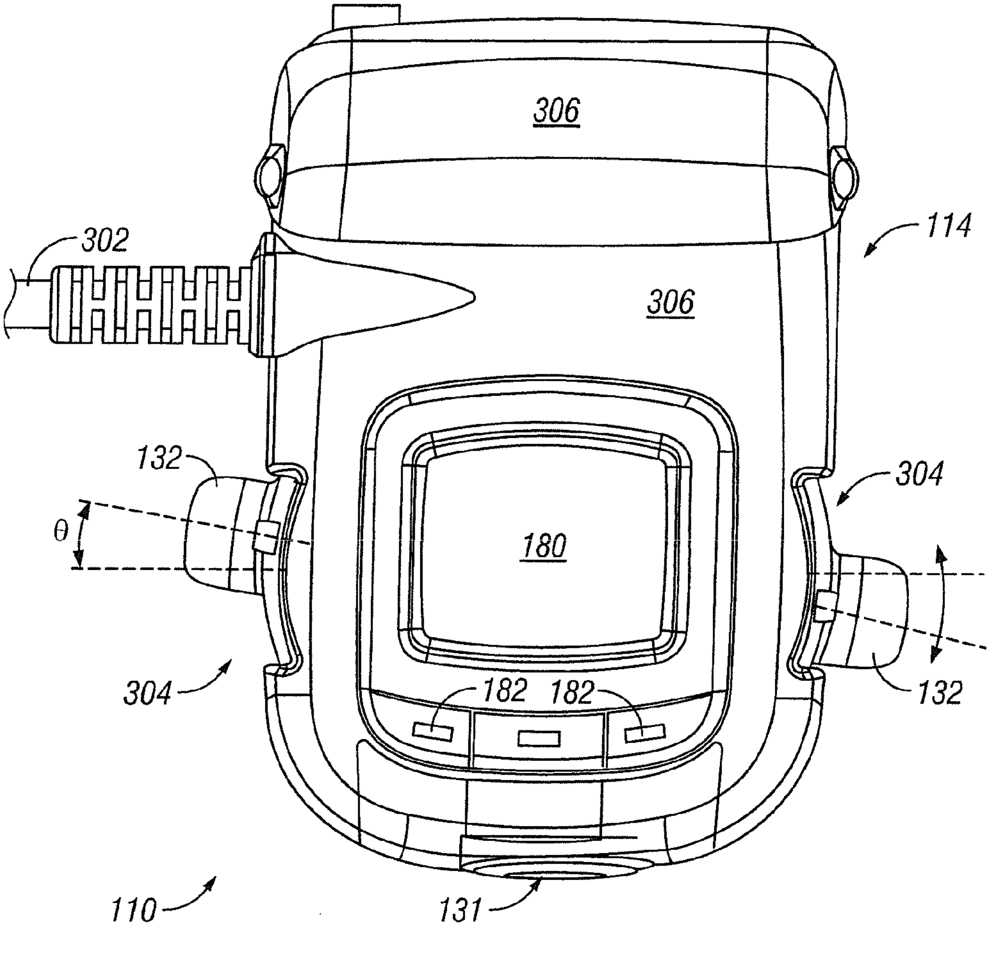
FIG. 3*a* is a top elevational view of the exemplary apparatus of FIG. 1, illustrating the interior element thereof and its relationship to the support frame.

FIG. 3*a* is a top elevational view of the bracelet 110 of FIG. 1, showing the top surface of the interior element 114. As illustrated, the element 114 comprises a somewhat rounded shape and includes a preload recess 180, plurality of indicators 182, electrical signal and power coupling 302, and two lateral latch mechanisms 304 adapted to mate with the sensor support frame 132 (e.g., that of FIG. 1*e*) as described elsewhere herein. The outer surfaces of the interior element 114 are comprised of a series of interlocking molded plastic (e.g., ABS) cover elements 306 which mate to the underlying frame components described below. An electrical (signals) interface port 131 is also disposed in the front portion of the interior element 114, thereby allowing electrical communication with the sensor assembly 101 during use.

The interior element 114 is articulated with respect to the pivot assembly 120 as previously discussed, thereby allowing the apparatus 110 to be clamped over the subject's limb.

Figure 3B:
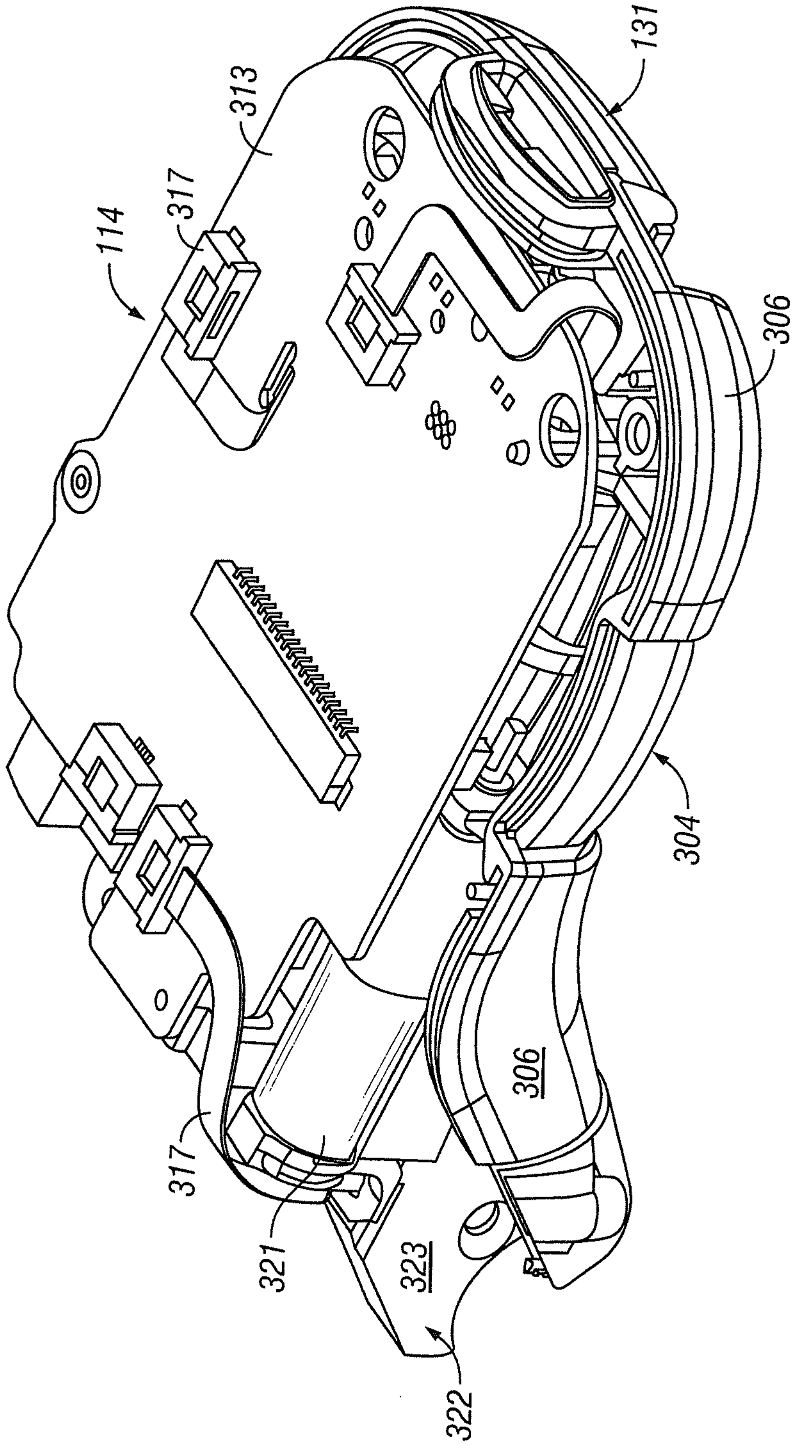
FIG. 3*b* is a top perspective view of the interior element of FIG. 3*a* shown partially disassembled, illustrating the various internal components including the circuit board.

FIG. 3*b* illustrates the interior element of FIG. 3*a* with some of the exterior covers 306 removed. As shown, the interior element 114 includes an internal circuit board 313, which includes inter alia, electrically conductive traces (not shown), integrated circuits (not shown), electrical ribbon cable and connectors 317, and other various electrical and electronic components. A lateral positioning motor (and associated gearbox assembly) 334, used for lateral positioning of the sensor assembly 101 during operation, is also shown. The circuit board 313 provides electrical interface for the various electrical functions within the apparatus 110, including the motor control and power circuits, transfer of the electrical signals derived from the sensor assembly 101 to the external controller, support for electrically driven indications (e.g., LEDs), etc. FIGS. 4*a*-4*d* herein illustrate an exemplary schematic of the various electrical functions within the apparatus 110. The construction and operation of these boards and their associated components is well known and accordingly not described further herein. It will be recognized, however, that in order to minimize the volume consumed by the board 313 and related components, maximal use of both miniaturized surface mount components and integrated circuits is provided in the illustrated embodiment.

Figure 3C:
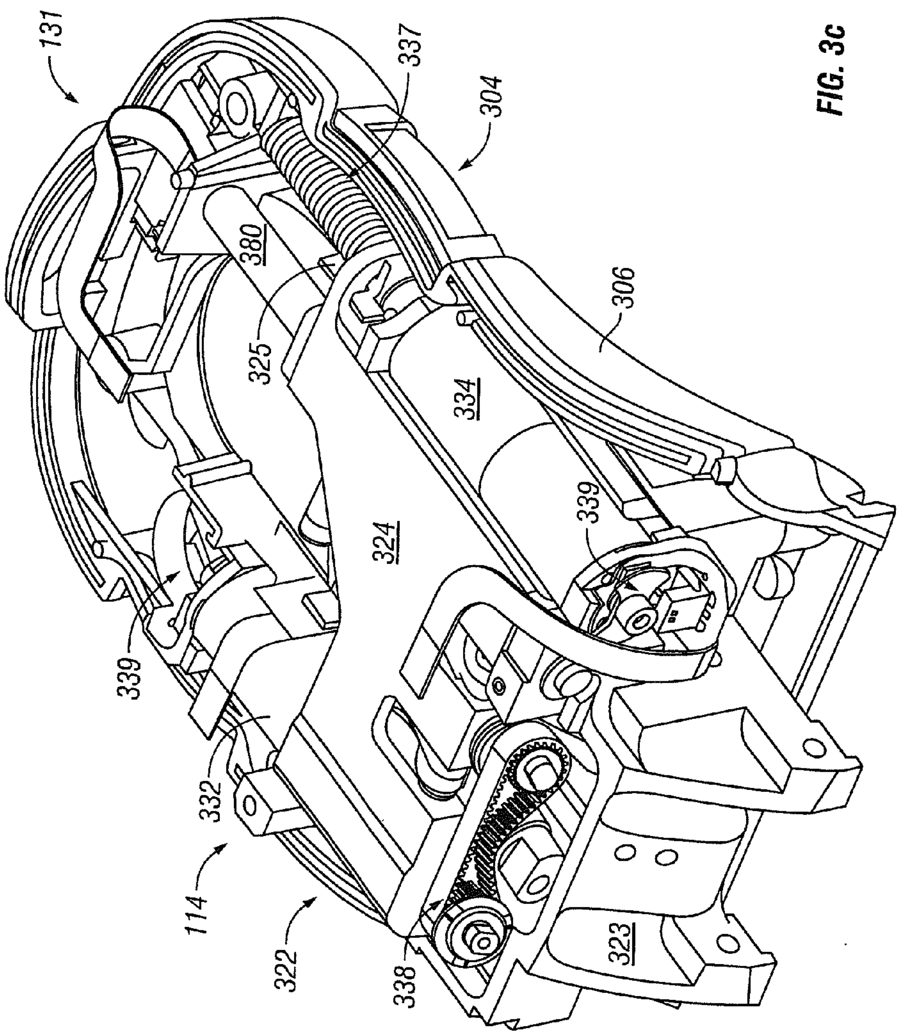
FIG. 3*c* is a top perspective view of the interior element of FIG. 3*a* with circuit board removed, illustrating the motor and actuator assemblies thereof.

Referring now to FIG. 3*c*, the interior element 114 further comprises a primary frame 322 which is comprised of two constituent frame components 323, 324 (FIGS. 3*f* and 3*g*) each formed of a lightweight aluminum alloy or other rigid material. The two frame components 323, 324 move with respect to one another under the action of the lateral positioning motor 334 as described in greater detail subsequently herein.

The frame 322 as a whole acts as a support structure for other components of the actuator assembly 106 and lateral positioning mechanisms. The one (non-traveling) component 323 of the frame 322 is mated (either via threaded fasteners, bonding, etc.) to a coupling block of the pivot mechanism 120, or alternatively the two components (i.e., frame component 323 and the coupling block) may comprise one commonly formed component, thereby providing additional rigidity and weight savings. The bearing portion 304 of the frame element 323 cooperates with the pivot mechanism 120 (including the secondary clutch plates 153), such that the interior element 114 can rotate (or not) around the corresponding pivot mechanism axis 121 depending on the state of the clutch plates 152, 153. Specifically, the pivot assemblies 147*a*, 147*b* (FIG. 1*f*) are attached to the non-traveling component 323 of the frame 322 in the illustrated embodiment, although other attachment schemes may be used.

Figure 3D:
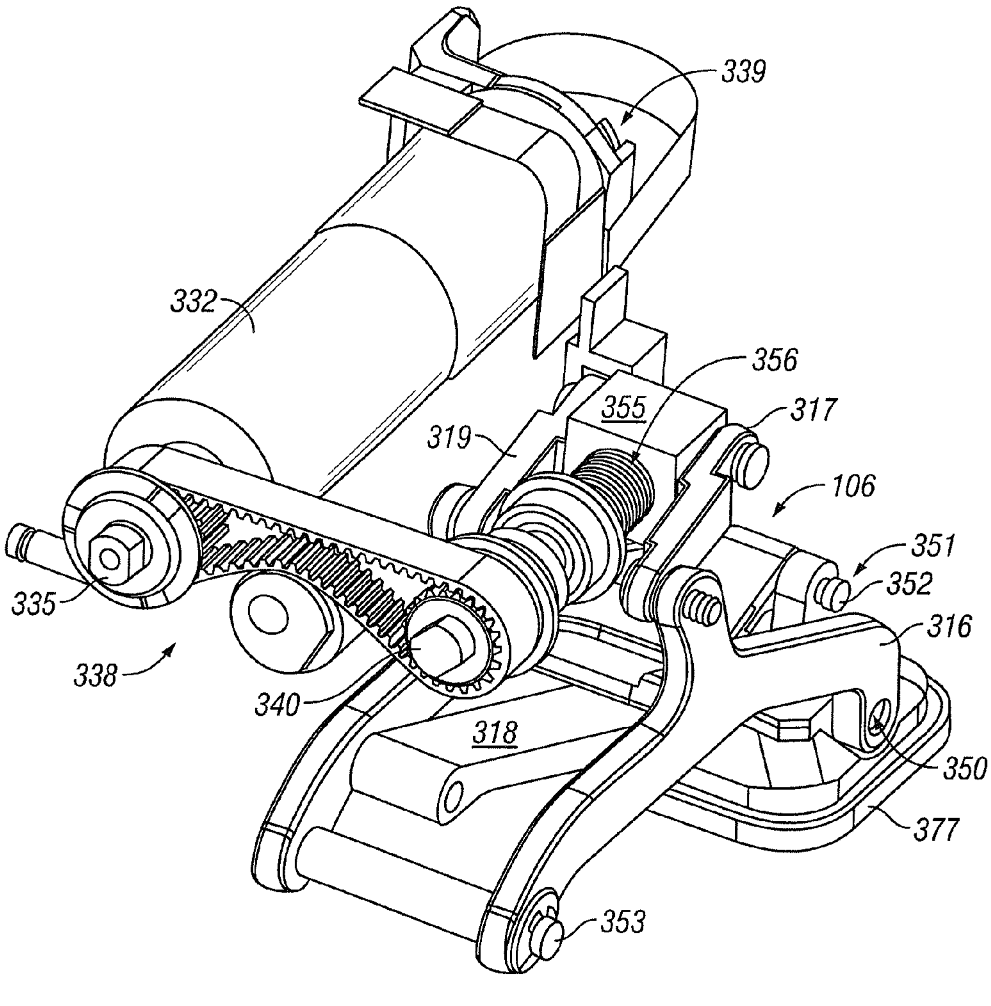
FIG. 3*d* is a rear perspective view of the actuator assembly of the apparatus of FIG. 3*a* shown in isolation.
Figure 3E:
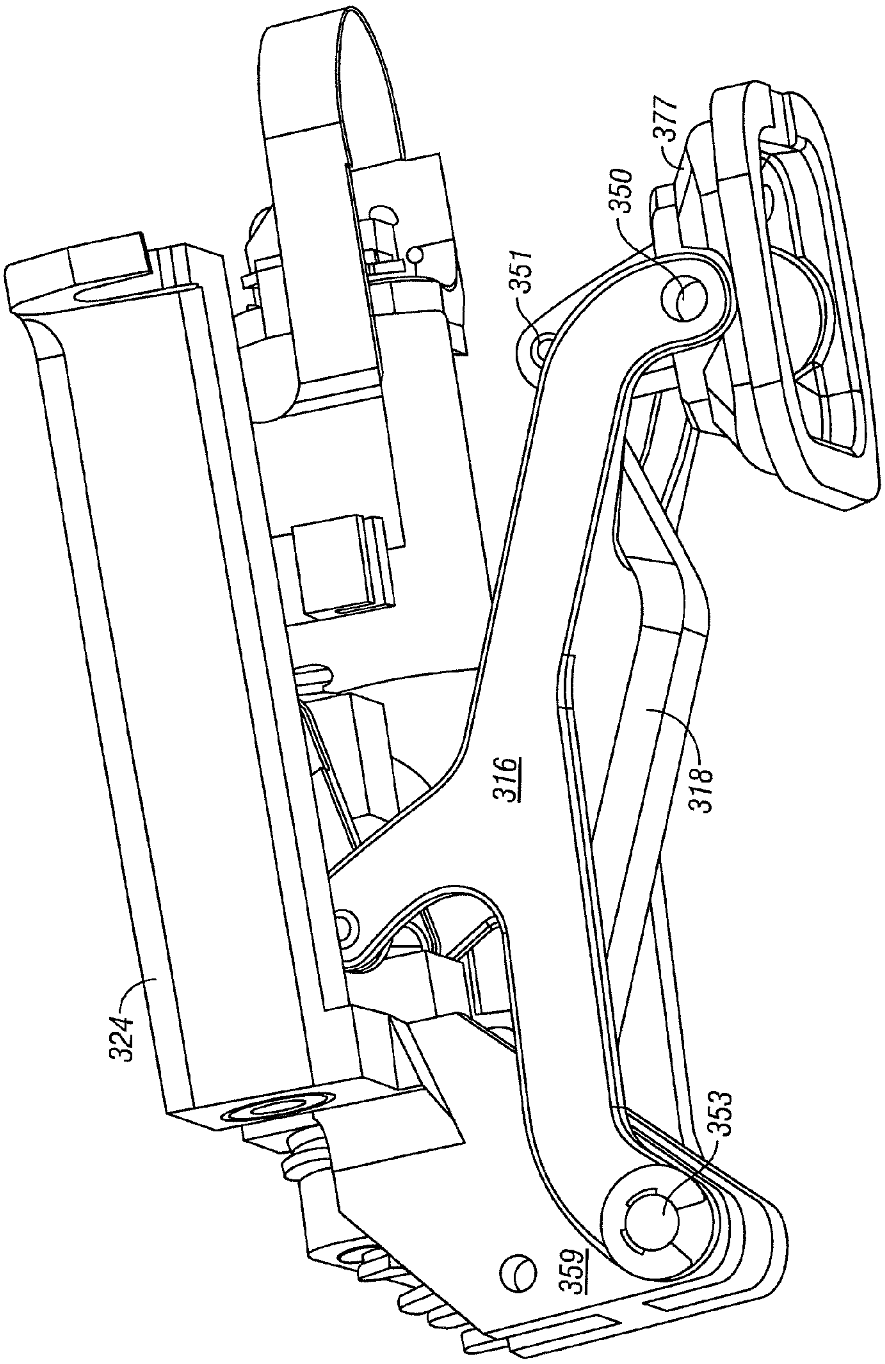
FIG. 3*e* is a side perspective view of the actuator assembly of FIG. 3*d* shown coupled to a first portion its supporting frame.

As shown in FIGS. 3*c*-3*e*, the frame 322 collectively houses many of the components of the actuator 106, including the applanation and lateral positioning motors 332, 334 and lever arms 316, 318 used to position the sensor assembly 101 when coupled to the adapter 377. The construction and operation of these components are now described in greater detail.

Figure 3F:
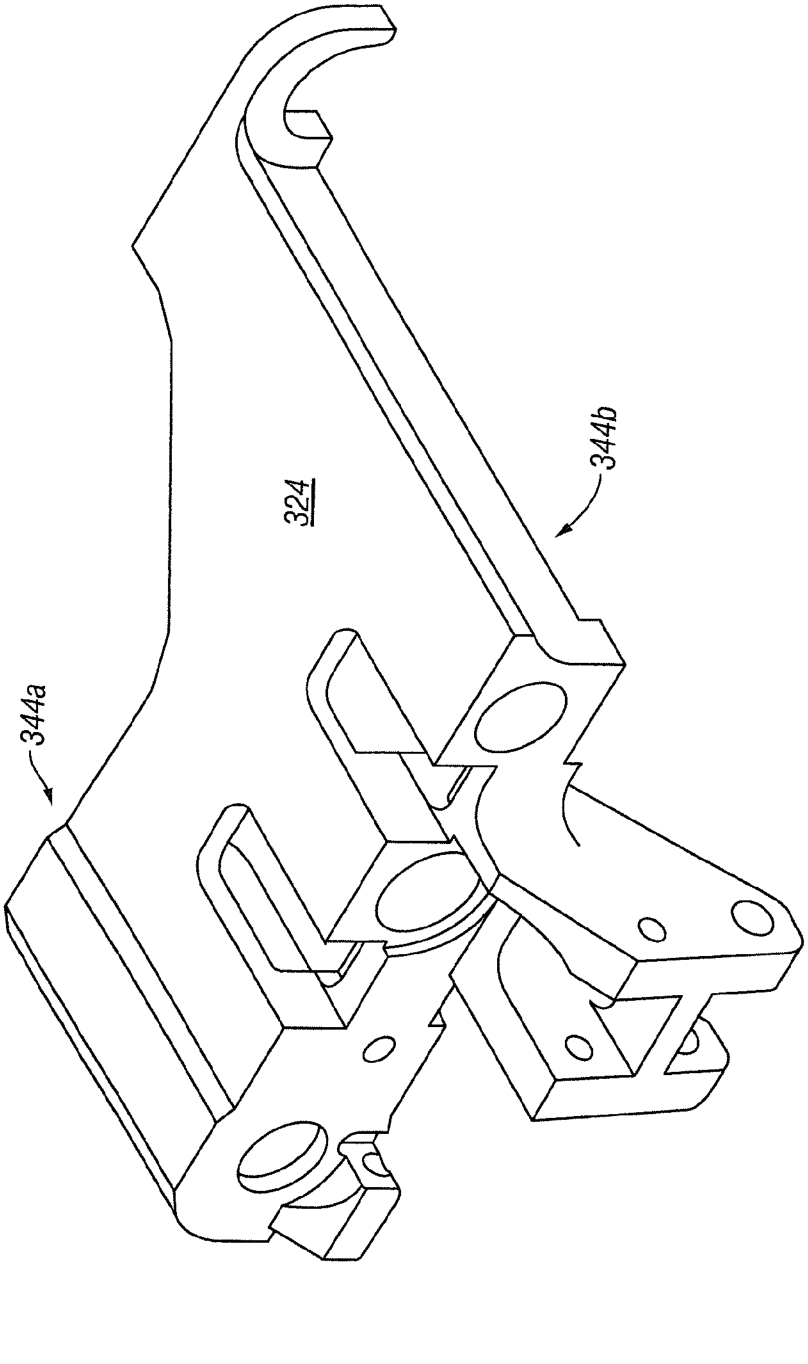
FIG. 3*f* is a top perspective view of the first portion of the actuator supporting frame of FIG. 3*e*, shown in isolation.
Figure 3G:
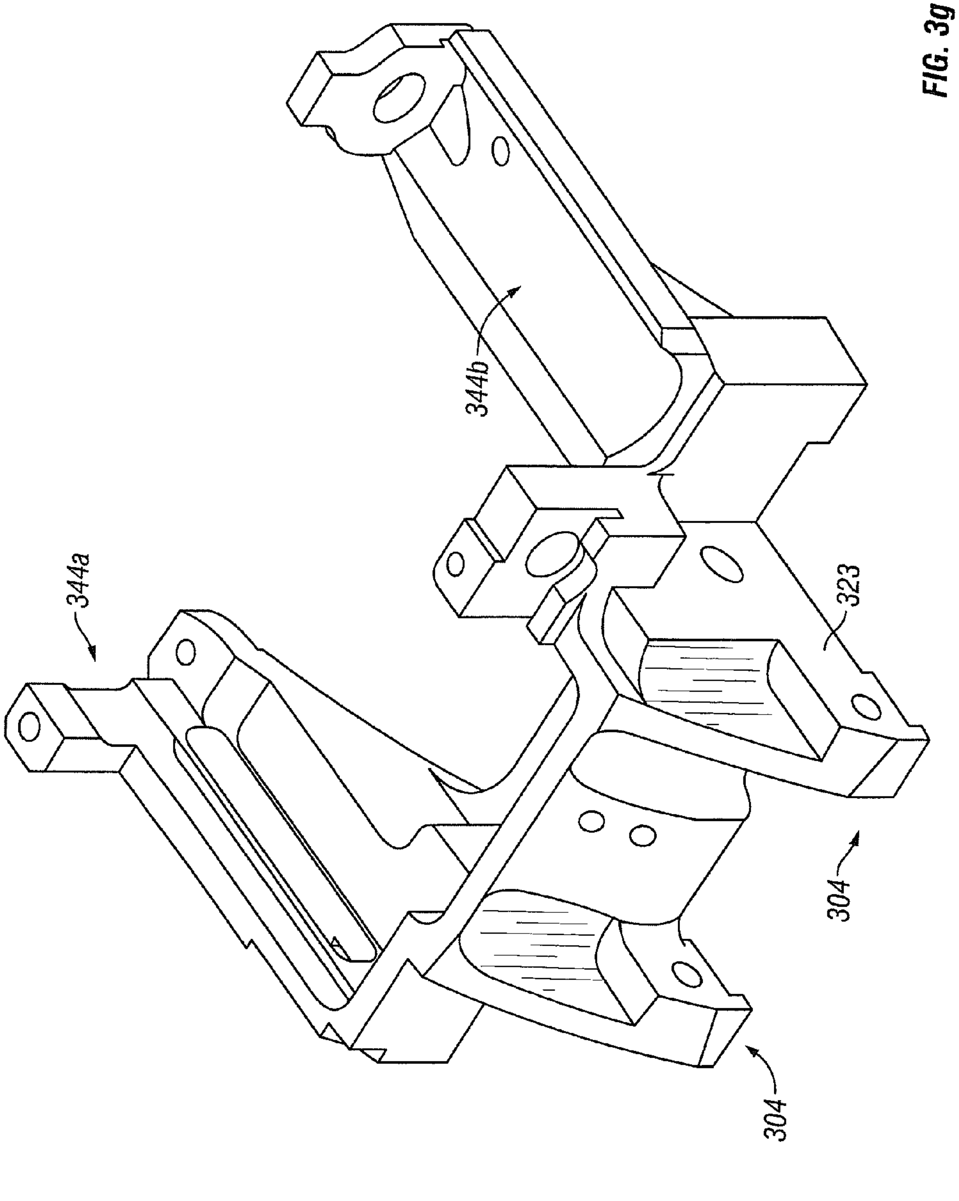
FIG. 3*g* is a top perspective view of the second portion of the actuator supporting frame, shown in isolation.
Figure 4A:
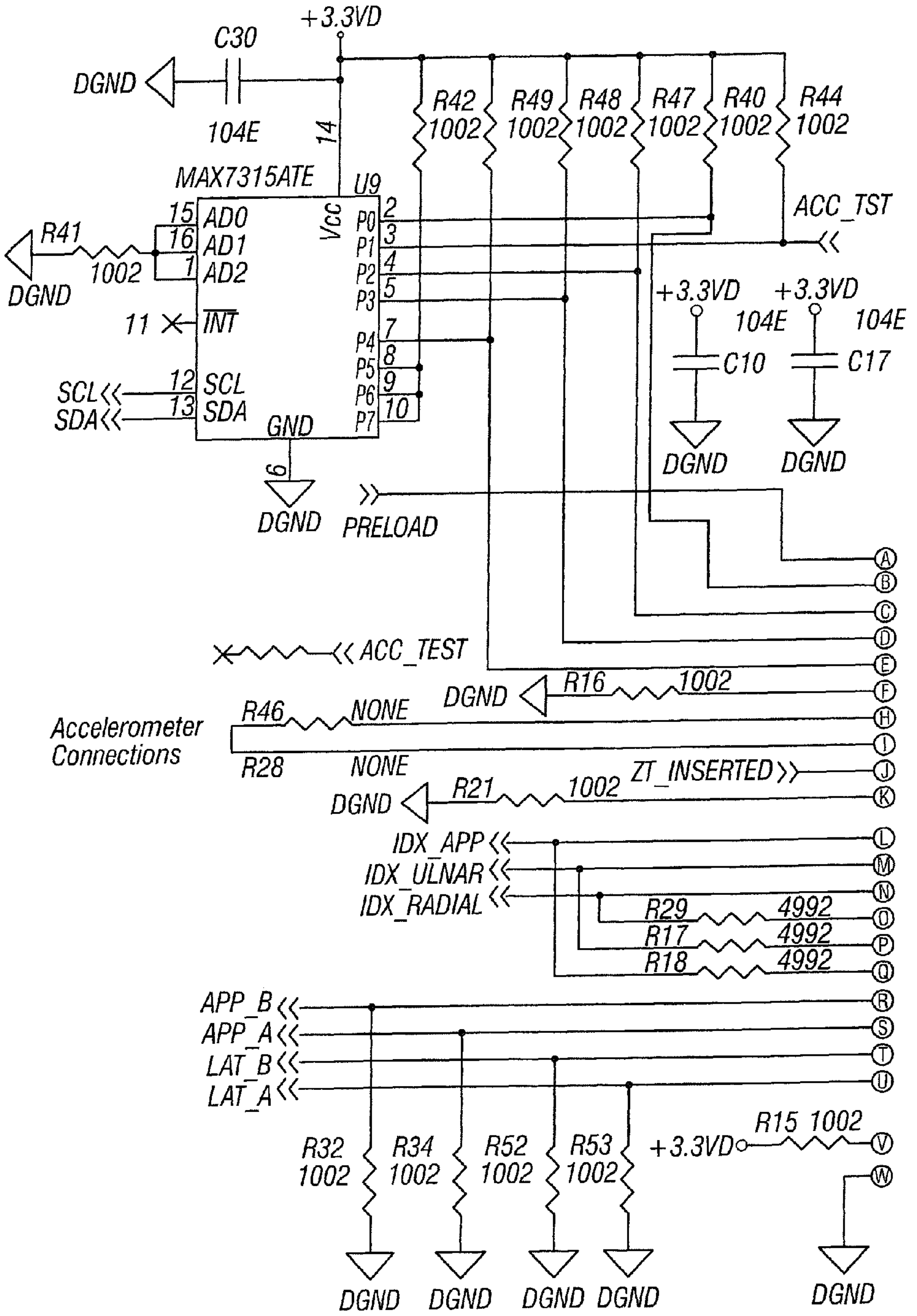
FIGS. 4*a*-4*d* are schematics of exemplary embodiments of the logic, pressure sensor, applanation index, and lateral index circuits of the apparatus of FIG. 1.
Figure 4A:
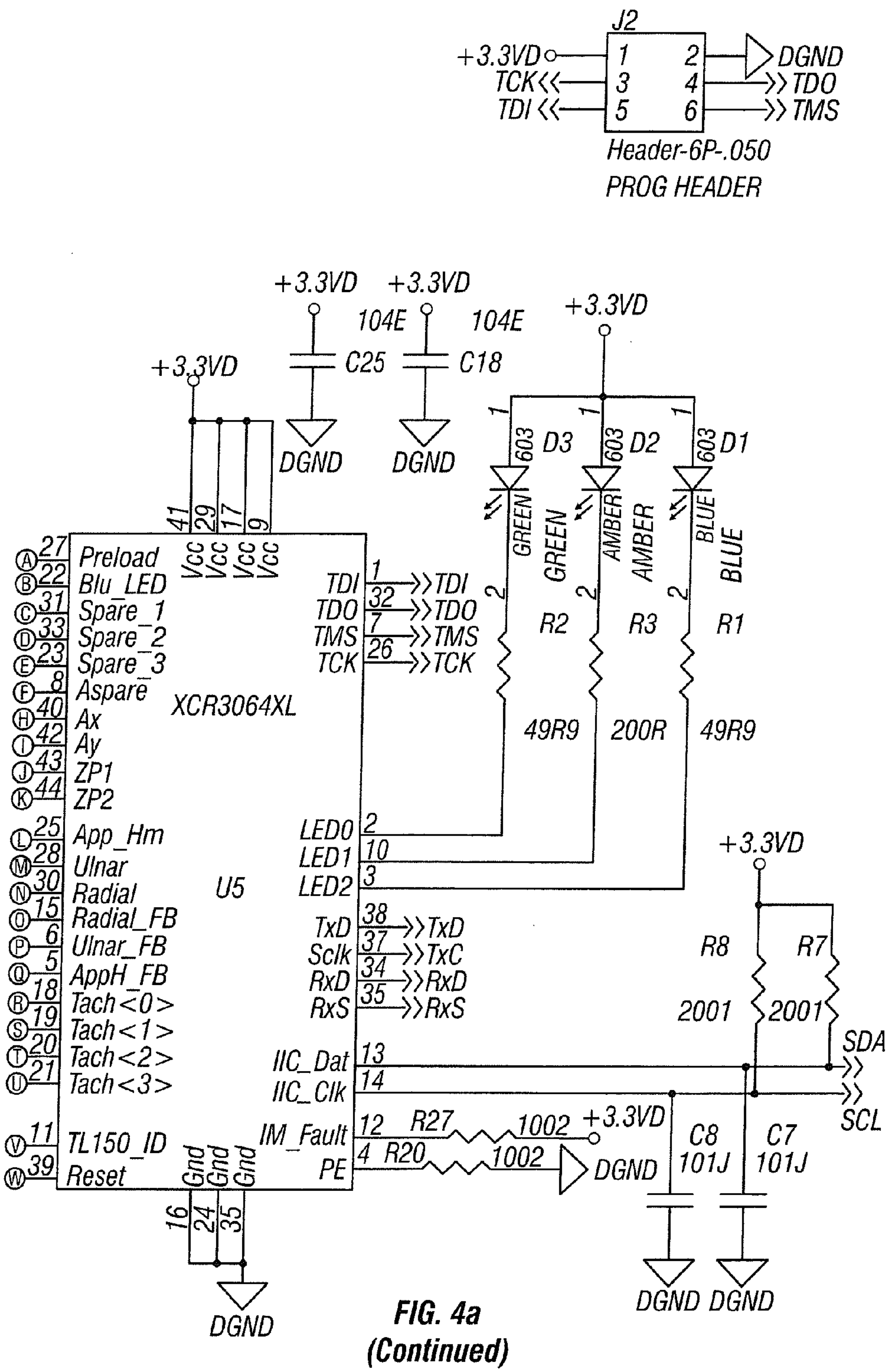
Figure 4B:
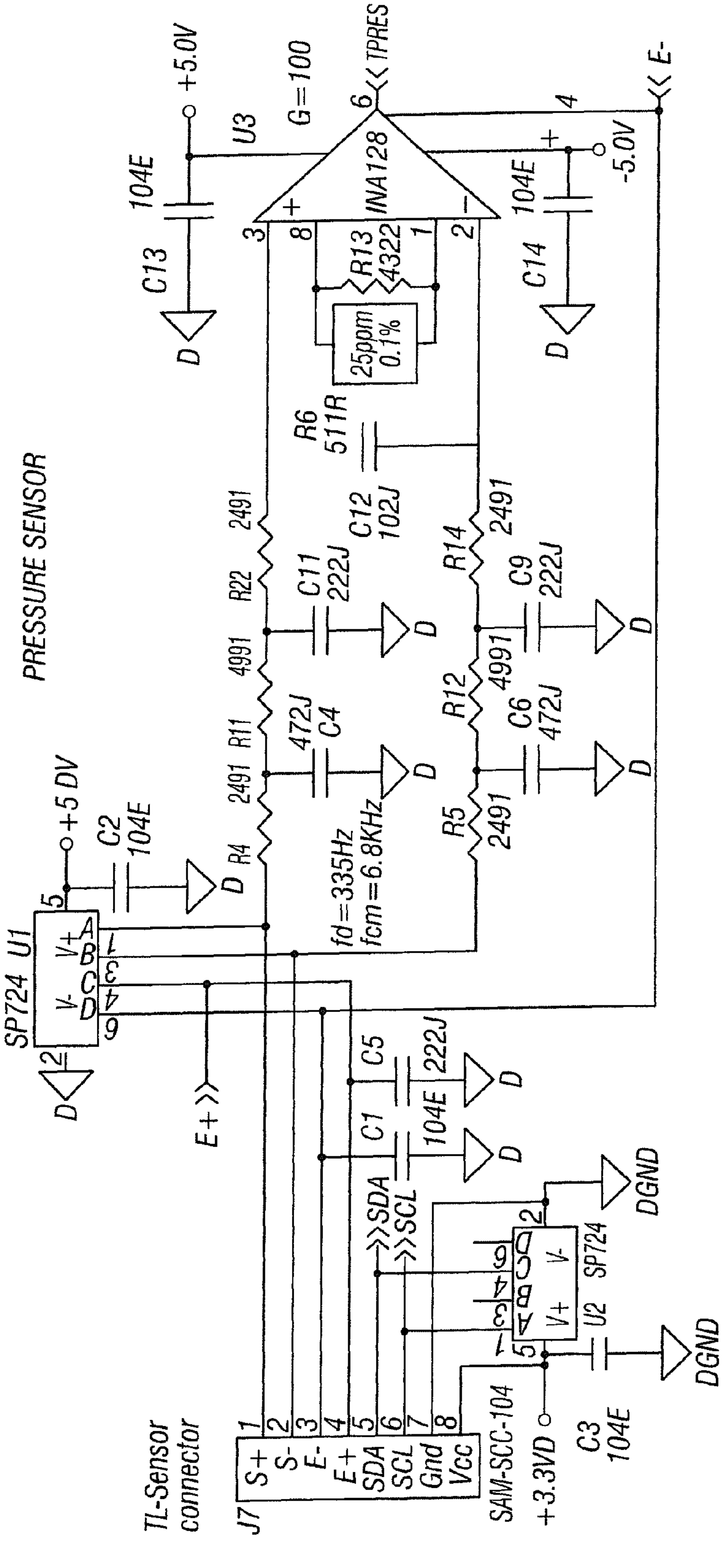
Figure 4C:
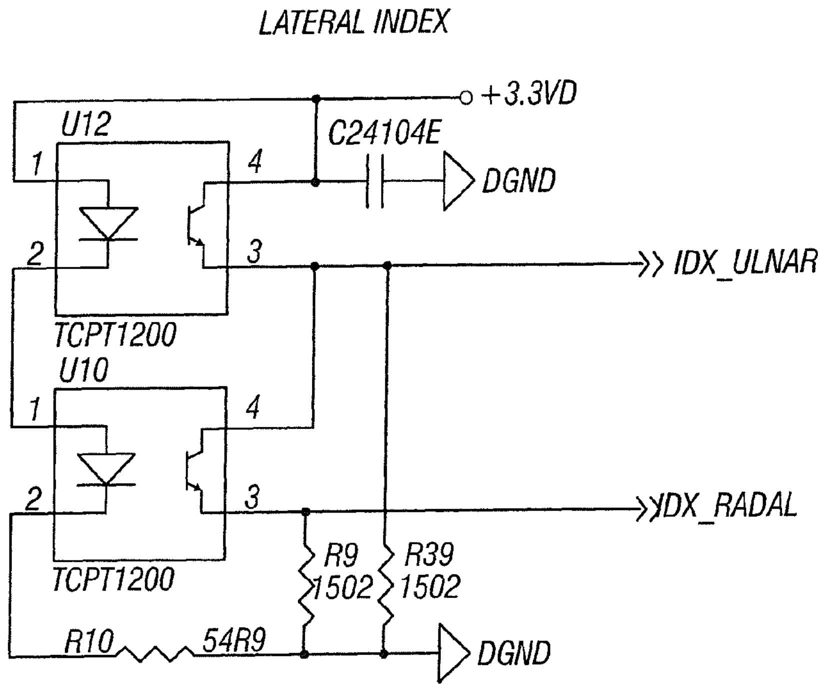
Figure 4D:
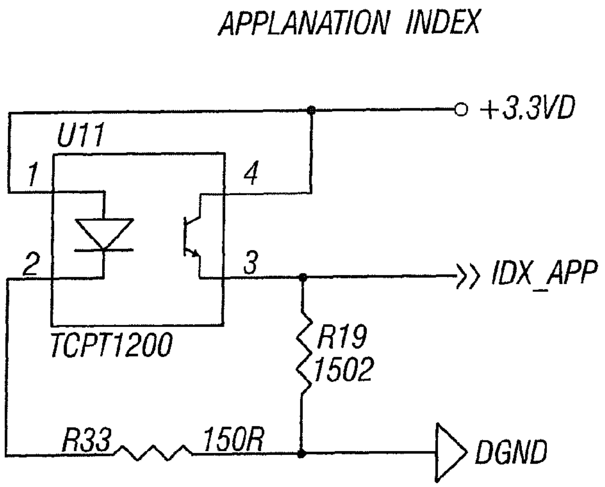

As shown best in FIGS. 3*f*-3*g*, the support frame elements 323, 324 includes internal recesses 344*a*, 344*b* in which the two motors 332, 334 are respectively situated, the applanation motor 332 being transversely situated in a traveling support structure disposed within the first recess 344*a*, and the positioning motor 334 being similarly situated in the second recess 344*b*. The output shaft 335 of the applanation motor 332 is coupled via toothed belt drive arrangement 338 to the applanation drive shaft 340 disposed centrally within the traveling support frame 324. It will be appreciated, however, that the aforementioned belt drive 338 may be readily replaced with a gear arrangement, or any other approach known to those of ordinary skill in the mechanical arts.

The motors 332, 334 also include one or more position encoders 339 which provide an electrical signal to the host system processor and associated algorithm to very precisely control the position of the applanation element (sagittally and/or laterally, as applicable) during operation. Accordingly, the variable used in the present embodiment to represent applanation element position is the number of motor increments or steps (positive or negative relative to a "zero" point); this approach advantageously removes the need to measure the absolute position with respect to the subject's tissue or anatomy. Rather, the relative number of steps is measured via the position encoder(s). This also underscores another advantage of the present apparatus; i.e., that the apparatus is "displacement" driven and therefore is controlled as a function of sensor assembly displacement, and not force. This advantageously obviates the complexities (and potential sources of error) associated with measuring force applied via a tonometric sensor or other applanation element.

It will be recognized that while DC drive motors (e.g., Faul-Haber "MicroMo" units) are used in the instant embodiment, other types of motors (e.g., stepper motors, etc) may be used as the motive force for the assembly.

It will further be recognized that the exemplary embodiment of the actuator mechanism 106 described herein allows for the separation of the movement of the sensor assembly 101 in the various directions; i.e., applanation, lateral, and optionally distal-proximal (not shown). This approach is important from the standpoint that it both allows concurrent yet independent movement in the various directions, as well as allowing for a highly compact and space/weight efficient actuator 106. Furthermore, in that a number of components within the actuator (including the motor 332) do not translate or dislocate within the actuator 106 during applanation, the moving mass is minimized, thereby reducing electrical power consumption as well as any effect on pressure measurements resulting from the translation of a mass within the actuator 106 during such measurements.

As best shown in FIG. 3*c*, the traveling frame structure 324 is free to move transversely (i.e., laterally across the width of the subject's arm when the bracelet is installed) under motive force provided by the lateral positioning motor 334, coupled through a threaded drive shaft arrangement 337 in which a traveling block 325 engages the traveling support structure 324 and causes it to slide laterally within the other (non-traveling) frame 323. The traveling structure 332 is further guided by the presence of guide shaft 380 which effectively runs the length of the transverse dimension of the frame 323, capturing the traveling structure 324 and its components within the non-traveling frame 323.

Also part of the traveling structure 324 are the first and second lever arms 316, 318 (FIGS. 3*d* and 3*e*) which are used to control the attitude and position of the sensor assembly adapter 377, the latter which mates with the dome 104 of the sensor assembly 101. These arms 316, 318 and their associated components collectively provide a great degree of control over the sensor assembly 101, allowing for independent variation of its vertical position or level of applanation while maintaining a constant attitude. Hence, this arrangement overcomes the prior art deficiency of a changing sensor attitude or orientation relative to the blood vessel of interest as the level of compression (applanation) is varied, thereby removing artifact associated with such changes and accordingly increasing the accuracy and repeatability of measurements.

Specifically, the four primary components of the arm assembly 316, 317, 318 and 319 are coupled to one another as best shown in FIG. 3*d* such that the application of forces on one component cause resulting forces to be exerted by the other components so as to keep the sensor attitude substantially constant (here, normal to a plane disposed roughly parallel with the plane of the interior element when installed on the subject at any elevation (applanation level). As shown in FIGS. 3*d* and 3*e*, the sensor assembly adapter 377 includes two independent pivot axes 350, 351 which are mated to respective ones of the first and second lever arms 316, 318 via hinge pins 352 which allow the arms to move relative to the adapter 377. The first arm 316 is also hingedly mated to the lever arm support portion 359 of the traveling frame 324 via another pin 353.

Hence, in the exemplary configuration, the first arm 316 acts to maintain a constant attitude or angle of incidence for the adapter 377 under varying vertical positions, the latter being controlled predominantly by the second arm 318. Specifically, the coupling of the second arm 318 at its distal end to the second pivot axis 351 of the adapter 377 allows the positioning motor 332 to exert a downward force on the adapter 377 via a traveling nut 355 and threaded shaft 356 and linkages 317, 319; as the adapter 377 extends downward in applanation, the fixed length of the first arm 316 exerts a force on the first pivot axis 350 of the adapter 377, causing it to rotate backwards around the second axis 351, in essence keeping the adapter level. This arrangement also advantageously allows for direct correlation between the total displacement of the sensor assembly 101 and its actual height.

In the illustrated embodiment, the lever arms 316, 317, 318, 319 are all formed from lightweight aluminum alloy (e.g., such as Aluminum 5052 H-32 alloy, or 6061T6, or 7075T6), although other materials such as polymers can be used. The weight of each component is therefore on the order of only a few grams. The adapter 377 is made from a molded polymer such as ABS for light weight and low manufacturing cost. The adapter 377 is also optionally attached to the elastomer bellows 187 which seals the mechanism. The adapter 377 may be e.g., solvent-bonded to another component that traps the bellows around the outside edge of the adapter 377.

It will also be appreciated that the use of such lever arms 316, 318 also lends itself to the optional addition of a strain beam sensor of the type well known in the art, such sensor being used for, e.g., determining the amount of force applied to the sensor assembly and hence the arm(s). As previously referenced, this strain gauge may also optionally be used for measuring or assessing the preload or static compression applied by the apparatus 110 when initially fitted to the subject for monitoring. In the illustrated embodiment, the strain gauge is applied to one of the lever arms 316, 318 and measures the deflection (strain) resulting from the application of force by the applanation motor 332 and the reaction force generated by the compressed tissue (and portions of the sensor assembly). This generates a proportional electrical voltage which is converted to a force value via the control module electrically coupled the apparatus 110. The force value determined from the strain gauge can be used for other functions, including for example calibration and even correction of measured tonometric pressure values for bias.

Furthermore, the strain gauge can also be used to determine when and how the device de-couples from the wrist, and therefore gives the ability to differentiate between an event in which the mechanism moves the sensor off of the subject's skin, and one where the subject's pressure drops due to physiologic reasons. This is of great benefit to improving the motion tolerance of the system (i.e., making it more clinically robust), since motion or other artifacts can be effectively separated from physiologic events in real time.

Similarly, a load cell of the type known in the electromechanical arts can be used consistent with the invention. Such load cell allows for, inter alia, the detection of sensor-induced load, which can then be accounted for to make the resulting measurement data more representative of the true physiologic signal, and hence more accurate. It may also be used to aid in the proper initial adjustment of the bracelet apparatus 110; i.e., how hard to clamp the interior and anterior elements 114, 116 onto the subject's wrist so as to provide a firm and non-compliant installation without unduly biasing the tissue which may affect the accuracy of any subsequent pressure measurements.

While the illustrated embodiments utilize a fixed length for both the first and second levers 316, 318, it will be recognized that these component may be configured so as to have a variable length (or other dimension) or otherwise include additional pivot points, such that the user/caregiver or even the apparatus itself can adjust the sensor attitude as a function of one or more other variables. For example, in one variant, the default attitude (maintained substantially constant over the entire range of applanation motion) is manually adjustable by the user, such as via adjustment of the length of one or more links within the lever arms 316, 318, or through use of a telescoping arm arrangement of the type known in the mechanical arts.

In another variant, one or more of the arms contains a tertiary pivot point, which causes the attitude profile as a function of applanation position to be complex (e.g., substantially constant during a first phase, with a variable rate of change of attitude during a second phase), so as to accommodate the curvature of the writs tissue in the vicinity of the radial artery.

In yet another variant, the system controller (whether external to the apparatus 110, or internal such as in the embodiment of FIG. 5 discussed below) is adapted to cycle the sensor assembly 101 via several different applanation sweeps with different sensor attitudes, the latter being adjusted by a small electric motor or similar mechanism (not shown) operatively coupled to the lever arm(s) 316, 318 and adapted to vary their geometry. Pressure data obtained from each sweep at each different attitude is then input to an algorithm running on the controller, which evaluates the data for one or more acceptance criteria to select the most optimal attitude for the particular subject and conditions. Such criteria can include, e.g., Signal-to-Noise Ratio (SNR), amplitude of one or more waveforms, the presence of a particular noise artifact, ratios of waveform features (e.g., pulse pressures), etc.

In still another variant, one or more of the lever arms 316, 318 can be made to have a curved or other shape in one or more dimensions, so that the arms are more particularly adapted to specific physiologic features. For example, in certain classes of patients having the accessible portion of their radial artery disposed further towards the hand, and/or wrapped further over the top of the wrist, lever arms 316, 318 having a curved vertical profile may be better suited such that the remainder of the apparatus 110 can be comfortably and normally situated on the subject's wrist. The sensor assembly 101 is therefore the only component which is in effect moved in position and attitude to accommodate the peculiarities of this class of patient.

Similarly, in still another embodiment, the lengths of one or both of the two arms 316, 318 can be made such variations in the "roll" (i.e., lateral-medial) orientation are created during applanation. Specifically, in the exemplary embodiment described above with respect to FIGS. 3*d* and 3*e*, the two arms 316, 318 are of equal length, and so the linkage design creates a substantially linear motion. However, if one of the arms 316, 318 is made different in length than the other, then the attitude of the adapter 377 varies as a function of applanation; e.g., there is a curvature to the path that the adapter 377 would take as it moves.

It will further be recognized that while the adapter 377 of the illustrated embodiment comprises a somewhat pyramid-shaped element, other shapes and sizes may be utilized with success. For example, the adapter 377 (and its corresponding sensor assembly adapter component 104) could comprise complementary conic or frustoconical sections. As yet another alternative, a substantially spherical shape could be utilized. Other alternatives include use of multiple "domes" and/or alignment features, inversion of the first and second elements (i.e., the first element being substantially female and the second element being male), or even devices utilizing electronic sensors to aid in alignment of the two elements 104, 377.

Additionally, it is noted that while the illustrated embodiment of the interior element 114 is constructed for use with the sensor assembly 101 (and corresponding alignment frame structure as described in detail in, e.g., U.S. application Ser. No. 10/920,999 filed Aug. 17, 2004 as previously incorporated herein), the bracelet apparatus 110 may be configured in a variety of different ways in terms of its interaction with the sensor assembly 101 and alignment frame. In one variant, the sensor assembly 101 is simply mated to the adapter 377 before use (the adapter 377 being fully retracted into the interior element 114 by the lever arms 316, 318). Hence, the user merely snaps the sensor 101 into place, places the bracelet 110 onto the subject's wrist, and then allows the algorithms within the controller to scan for the optimal location of the sensor before calibration and measurement is conducted.

In one variant (see discussion of FIG. 6 below), the combined sensor assembly 101 and alignment frame is placed over the users anatomy using, inter alia, the alignment reticle. The caregiver then places the bracelet apparatus over top of the sensor/frame, coupling the adapter 377 to the sensor assembly dome 104. The interior element 114 may also be adapted, if desired, to mechanically couple to the alignment frame using, e.g., the latch features 304 shown in FIG. 3. The exemplary alignment frame comprises a set of inward projecting tabs which engage corresponding latch features 304 within the lateral portions of the interior element 114, such as disclosed in U.S. application Ser. No. 10/920,999 previously incorporated herein. In this fashion, the bracelet 110 is removably locked onto the alignment frame, the latter which is adhered to the subject's skin.

Alternatively, however, the bracelet 110 of the present invention may be operated without any mechanical locking or coupling between itself and the alignment frame (with the exception of the coupling to the sensor assembly 101 via the adapter 377), thereby making the bracelet 110 substantially free-floating with respect to the alignment frame.

Note, however, that a minimum sufficient rigidity of the bracelet apparatus 110 is required to accommodate the reaction forces generated by the actuator assembly 106. Specifically, the actuator 106 is rigidly mounted to interior element 114 as discussed above, and the interior element is rigidly coupled (when locked) to the pivot mechanism 120, the latter also being rigidly yet rotatably coupled to the anterior element 116. The anterior element may be coupled to the brace element 195 as previously described, or alternatively may simply couple directly to the subject's tissue (e.g., back of the wrist/forearm). Hence, a fully articulated yet highly non-compliant system is formed that, when properly installed on the subject, provides the required degree of rigidity and reaction force. This high degree of rigidity allows for increased accuracy in the tonometric pressure measurement, since variations in the measured pressure resulting from the compliance of various portions of the apparatus are virtually eliminated. The interior and anterior brace elements 114, 116 may also optionally include pads (e.g., foam, silicone rubber, or comparable) disposed on the interior surfaces thereof to permit the use of the apparatus 110 on the subject for extended periods without discomfort; however, these advantageously add very little in the way of compliance. The pads of the exemplary apparatus are designed with a comparatively large surface or contact area to the subject's tissue, such that the reaction forces transmitted via the apparatus 110 to the pads are distributed across a large area of tissue, thereby further mitigating the effects of compliance.

As best shown in FIG. 1*b*, the adapter 377 of the actuator 106 penetrates the interior portion 188 of the interior element 114 via a flexible bellows or boot assembly 187 that fits around the neck of the adapter 377 and allows the actuator and adapter 377 to move both in the sagittal and lateral directions as the actuator and/or traveling frame 324 moves within the interior element 114. This bellows 187 advantageously provides an environmental sealing function and also for the aforementioned movement of the actuator 106, all via a low cost and lightweight replaceable component.

Also, as best shown in FIG. 1*b*, the interior surface 188 of the interior element 114 further optionally includes additional coupling features 189 disposed proximate to the adapter 377. These features 189 couple to corresponding features on the support frame 132 (FIG. 1*e*), and collectively add rigidity and further support to the apparatus 110 during use.

As shown in FIGS. 1*b* and 3*a*, the lateral latch mechanisms 304 of the illustrated embodiment comprise circumferentially elongated grooves or recesses which are adapted to mate with the latch mechanisms (e.g., tabs) 178 formed on the vertical risers 177 of the support frame 132 (see FIG. 1*e*). The exemplary latch mechanisms 178 of FIG. 1*e* have a desirable feature relating to the relative movement of the actuator and the frame 132. Specifically, as best shown by the arrows of FIG. 3*a*, the interior element 114 and frame 132 can move relative to one another in a rotational manner (i.e., the interior element 114 can rotate within the frame 132) around a central vertical axis of the latter, up to as much as thirty (30) degrees in either direction. This advantageously allows for some degree of misalignment between the support frame element 132 and the interior element 114 when installed on the subject. As is well known, the geometry of the human forearm region is not cylindrical, but rather substantially (frusto) conic. Most individuals exhibit significant taper of the forearm dimensions as one proceeds in the distal-proximal direction. Hence, the substantially symmetric frame element 132 may be cocked or rotated somewhat when placed on a given individual due to this taper. If the interior element (and actuator 106) were to be mated to the frame 132 in a purely rigid manner with no rotation as previously described, then the actuator would necessarily be cocked or rotated relative to the radial artery, and hence the sensor and apparatus 110 also. It has been determined that the fit of bracelet 110 to the side of the wrist can be of significance. Specifically, if the apparatus 110 is not allowed to "yaw" with respect to the sensor/support fram to some degree, then it will not fit the subject's arm well, which can causes a less than desired degree of stability of the system during use. Furthermore, rotation of the apparatus around the wrist can produce somewhat of a distal-proximal component, which may be undesirable for a variety of reasons including e.g., the accuracy of any lateral position search algorithm used with the apparatus, although this effect has been noted to be small.

Rather, the rotational freedom imparted by the latch mechanisms 178 (and a corresponding elongated latch surface 304 present on the interior element 114 which allows the latch tabs the ability to slide along the length of this latch surface during relative rotation of the interior element 114 and frame 132) allows the element 114 to remain in a desired orientation while the frame element 132 is in its cocked or rotated position on the subject's forearm. Other mechanisms or approaches to providing such rotational freedom may also be used consistent with the invention, as can be appreciated by those of ordinary skill.

Coloration

In another aspect of the invention, selective use of color coding on various components is optionally utilized in order to make the setup and measurement processes more intuitive and so as to convey information to the user including, e.g., the sequence in which to take certain steps, and/or where certain components fit together (i.e., assembly instructions). Specifically, in one embodiment, portions of the bracelet apparatus 110 and the aforementioned sensor frame element 132 are given a particular color. This color, a vibrant "fluorescent" or lime green in the illustrated embodiment (although others may be used), is used either or both to (i) provide some level of guidance regarding assembly of the actuator 106 onto the sensor assembly 101 and support frame (i.e., "green goes with green"), and the interlocking of the frame tabs 178 onto the latch mechanisms 304 of the bracelet 110, and (ii) to correspond to other indicators present on the apparatus 110 (such as the colored LEDs 182) in order to guide the user through a sequence of events.

In terms of assembly, portions of the exemplary actuator 106 that mate with the sensor assembly 101 (Le., the adapter 377) and/or supporting frame element 132 are also color-coded (e.g., green) so as to illustrate to the user which portions of the various components mate up with one another. Similarly, the free end of the sensor electrical connector (pigtail) 107 of FIG. 1 c can be color-coded along with its corresponding receptacle 131 on the interior element 114 so as to indicate where the user should plug the pigtail in, such as by using a yellow color.

The color(s) may also be selected so as to coincide with one or more of the various indicators (e.g., LEDs 182) used with the apparatus 110. In a simple example of this feature, the user is guided through a series of steps corresponding to a sequence of indicator lights; i.e., when green LED lit, actuate green-colored component, when yellow LED lit, actuate yellow-colored component, etc. Hence, the user is stepped through the setup process by simply actuating the relevant color-coded component when an indicator associated with that component is illuminated or otherwise activated. Actions that may need to be taken include for example attachment of the actuator to the sensor assembly 101 and the support frame 132, insertion of the sensor electrical interface into the interior element port 131, removal of the paddle 133, etc.

It will also be recognized that the indicators may be disposed spatially on the apparatus 110 or the parent monitoring device (not shown) so as to further provide association with the location of the components which are to be actuated. As an illustration, consider the aforementioned example where the green LED is lit, thereby instigating the user to actuate the green-colored component. If the green LED is also placed immediately proximate to the green component, then the user is even less prone to make an error, since the indicator guides their eye to the location where the action must be taken. The user merely follows the illuminating lights in sequence to perform the required actions in correct order.

Accelerometer-based Variant

In another embodiment of the bracelet apparatus 110 of the present invention, one or more accelerometers are utilized with the actuator so as to provide pressure-independent motion detection for the device. As discussed in Applicant's co-owned and co-pending U.S. patent application Ser. No. 10/211,115 entitled "Method and Apparatus for Control of Non-Invasive Parameter Measurements" filed Aug. 1, 2002, which is incorporated herein by reference in its entirety, one method for anomalous or transient signal detection involves analysis of various parameters relating to the pressure waveform, such that no external or additional sensor for motion detection is required. However, it may be desirable under certain circumstances to utilize such external or additional sensor to provide for motion detection which is completely independent of the pressure sensor and signal. Accordingly, one embodiment includes an accelerometer (not shown) within the actuator 106 which senses motion of the actuator (and therefore the remaining components of the apparatus 110, since the two are rigidly coupled), and generates an electrical signal relating to the sensed motion. This signal is output from the actuator to the system controller/processor, and used for example to provide a windowing or gating function for the measured pressure waveform according to one or more deterministic or pre-determined threshold values. For example, when the accelerometer output signal corresponds to motion (acceleration) exceeding a given value, the controller gates the pressure waveform signal for a period of time ("deadband"), and then re-determines whether the measured acceleration still exceeds the threshold, or another reset threshold which may be higher or lower, so as to permit re-stabilization of the pressure signal. This approach avoids affects on the final calculated or displayed pressure value due to motion artifact.

Furthermore, the accelerometer(s) of the present invention can be utilized to gate or window the signal during movement of the applanation, lateral positioning, and/or distal-proximal and distal positioning motors associated with the actuator. As will be appreciated, such movement of the motors necessarily create acceleration of the sensor assembly 101 which can affect the pressure measured by the pressure transducer used in the sensor assembly 101.

Hence, in one exemplary approach, motor movement control signals and accelerometer output act as the basis for gating the system pressure output signal, via a logical AND arrangement. Specifically, when the motor control signal and the accelerometer output (in one or more axes) are logic "high" values, the output pressure signal is blocked, with the existing displayed value preserved until the next sampling interval where valid data is present. Hence, the user advantageously sees no change in the displayed value during such gating periods. Similarly, the motors may be stopped with the trigger logic "high" values. The motors will remain stopped until the accelerometer output falls back below the threshold, and subsequently resume or restart its prescribed operation.

In another exemplary embodiment, the accelerometer operates in conjunction with the aforementioned pressure based motion detectors. The pressure based motion detectors evaluate a plurality of beats to determine whether motion has occurred and a need exists to correct for that motion. Within that detection of motion a plurality pressure signatures consistent with motion are compared against motion thresholds for starting the motion correction process. These thresholds can be adjusted (i.e. lowered to trigger more easily) when the accelerometer senses motion of the actuator.

In yet another approach, the foregoing motor control and accelerometer signals (or the accelerometer signals alone) are used for the basis for calculating and assigning a "quality" index to the pressure data, thereby indicating for example its relative weighting in any ongoing system calculations. As a simple illustration, consider where the system algorithm performs averaging of a plurality of data taken over a period of time t. Using an unweighted or non-indexed scheme, data obtained during periods of high actuator/sensor acceleration would be considered equally with those during periods or little or no acceleration. However, using the techniques of the present invention, such data taken during the high-acceleration periods may be optionally indexed such that they have less weight on the resulting calculation of the data average. Similarly, indexing as described herein can be used for more sophisticated corrections to calculations, as will be readily appreciated by those of ordinary skill in the mathematical arts. Myriad other logic and correction schemes may be used in gating or adjusting the use of sensed pressure data based at least in part on accelerometer inputs.

As will also be recognized by those of ordinary skill, a single multi-axis accelerometer device may be used consistent with the present invention, or alternatively, one or more separate devices adapted for measurement of acceleration in one axis only. For example, the ADXL202/ADXL210 "iMEMS" single-chip dual-axis IC accelerometer device manufactured by Analog Devices Inc. may be used with the actuator 106 described herein, although other devices may be substituted or used in combination.

Autonomous and Semi-Autonomous Embodiments

In another embodiment of the apparatus 510 (FIG. 5), the control module and display functionality is disposed entirely within the apparatus 510 itself, largely within the empty volumes of the interior and anterior elements 514, 516, thereby making the device in effect completely autonomous of any external controller or display unit. Hence, rather than having to "play out" via a parent controller unit and/or an external patient monitor as in the embodiment of FIG. 1, the embodiment of FIG. 5 operates as a stand-alone device. This embodiment might be useful, for example, for in-home use by a subject, in applications where a great degree of mobility is required, or in space- or power-restricted applications (such as in an ambulance, aircraft, spacecraft, or submarine). Also, such complete mobility may be desired where a surgical or other patient must be moved to several different locations during the course of a procedure.

Figure 5A:
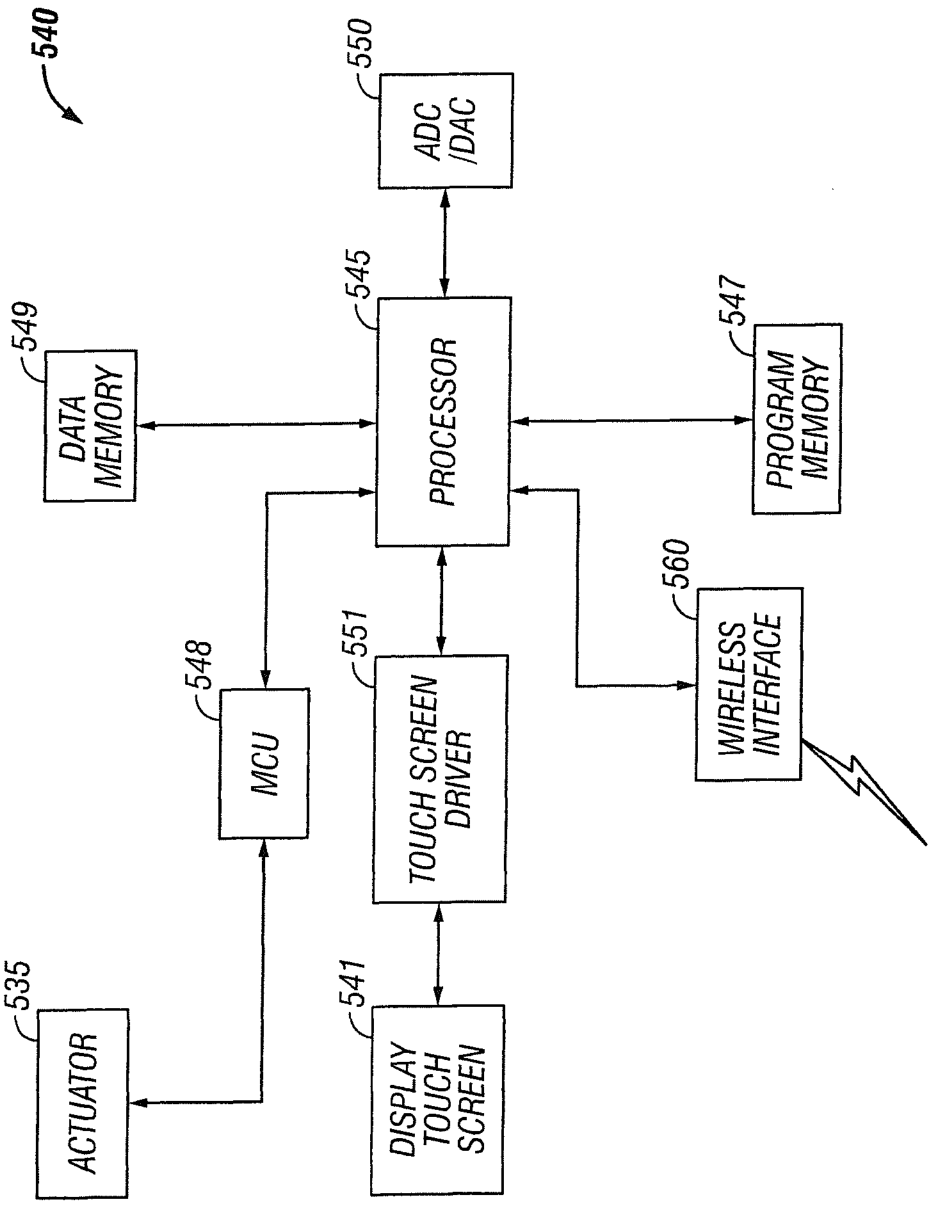

As shown in FIG. 5, the apparatus 510 includes interior and anterior elements 514, 516 and a pivot element 520, yet the interior element 514 further includes a small display and control unit 540 which includes a display device 541 (e.g., LCD or TFT), and a plurality of fixed and soft control functions 542. The control unit 540 further includes a digital processor 545 (see FIG. 5*a*) such as an optimized high performance embedded RISC device or DSP, as well as a program memory/storage device 547, MCU 548, data memory 549, and ADC/DAC unit 550. A touch screen driver 551 is also optionally provided to implement the "soft" or programmable key functionality, whereby the user can enter commands or information via the display screen 541 whether by finger, stylus, or via another user interface (UI). Somewhat akin to a PDA or handheld computer of the type now ubiquitous in the art, the control unit 540 is an embedded device that includes all of the requisite control functions and functionality required to operate the actuator 535, collect data, and process the data for display or transmission to another entity.

Exemplary embedded RISC processors useful with the embodiment of FIG. 5 are the A600 and A700 devices manufactured by ARC International of San Jose, Calif., which are readily optimized for small die area and low gate count (and hence very low power consumption) yet with high performance, e.g., up to 400 MHz. These features (small size and low power consumption) are especially desirable for the embodiment of FIG. 5, since it utilizes no external power source during operation. It will be appreciated that other types of processors may be used consistent with the invention, however, As previously described, a wireless interface (e.g., Bluetooth, UWB or IEEE 802.11) device of the type well known in the art may be used with the control module 540 to transmit and/or receive data. In the illustrated embodiment, an 802.11 insert card 560 is used to stream the data collected via the antenna 561 of the apparatus 510 to a remote unit (not shown) for display, storage or analysis, although local storage, display and/or analysis can also be utilized if desired. For example, using Bluetooth technology, a plurality of devices 510 can remain in data communication with a central monitoring station (such as in a hospital or other health care facility), the latter which can be used to wirelessly monitor several subjects simultaneously. This also permits ready transit of the subject (such as on a gurney) from one location to another without having to disconnect any electrical connections, or alternatively move the monitoring device(s) with the subject during transit.

The control unit 540 can also be programmed or configured to provide alarm functions, monitoring, and the like, thereby freeing the caregiver or user from constantly watching the display unit 541. Such programming and configurations are well known to those of ordinary skill in the electronics arts.

The device 510 of FIG. 5 may also be battery powered (rechargeable or otherwise) if desired, thereby further increasing its mobility and autonomy. In one variant, the anterior element 516 is made easily separable from the rest of the apparatus 510 (as previously described), yet so as also to include an integral (quick disconnect" electrical power coupling (not shown). A rechargeable storage battery is disposed within the anterior element 516, and hence the user can simply unplug (detach) one anterior element whose battery has been depleted, and plug in another with a fresh battery. Alternatively, the battery module 575 itself can be removed from the anterior element and replaced (see FIG. 5), thereby obviating having to re-adjust the placement and preload of the apparatus 510 when changing power supplies.

In yet another variant, the apparatus 510 is fitted with a USB or comparable interface, thereby allowing use of a "USB key" storage device such that data gathered by the apparatus can be off-loaded to the key for later analysis. Hence, the user/caregiver can merely place the apparatus for measurement (as previously described), insert the USB key into the port, and take measurements, the data from which is stored in the USB key. The USB key can then be taken to their physician's office, downloaded onto their PC or laptop for home analysis or e-mailing, "snail" mailed, or otherwise transferred to another location for further analysis. Those of ordinary skill will also recognize that a removable flash memory device such as those manufactured by Sandisk Corporation may be used in place of or in conjunction with the USB key, the flash card or device serving much the same function. Other interfaces such as IEEE-1394 FireWire can be used as well so as to port data externally (or even receive data from an external source, such as data relating to a patient's prior monitoring history).

As is well known in the embedded arts, the controller 540 can also be configured with a flash memory, thereby allowing rapid and portable reprogramming of the device in the field.

In yet another embodiment, the bracelet apparatus can be made semi-autonomous, wherein electrical power is supplied via an external physical link (power cord), yet data and/or control signals are transferred to an external monitoring and display unit (not shown). As yet another alternative, the bracelet may be self-powered and include a wireless data and signal interface as previously described, yet with the signal processing and display functions being accomplished by an external processing and display unit. In this variant, the "raw" data is streamed off-device via a wireless interface, thereby reducing the required processing capability and overhead of the bracelet 110 itself and allowing it to be smaller and less complicated.

While extant technology places limits on the size of the apparatus 510 presently achievable, it will be recognized that the device can also be configured (even using presently available technologies) so as to be sufficiently small, self-contained and lightweight so as to be worn for extended periods of time by a fully ambulatory individual. When coupled with other improvements described or incorporated herein, the device 510 can be made completely self-sufficient and robust so as to provide accurate yet non-intrusive monitoring under such circumstances. For example, through use of a wireless data transceiver, integral LCD display and control/analysis module, battery and/or solar power module, and transient detection and recovery algorithms as described elsewhere herein, the device 510 in effect comprises an overgrown bracelet having no wires or other external connections. The subject can wear this device while asleep, watching television, or even walking. For example, those suffering from CHF or similar ailments may wear the device 510 for ambulatory monitoring, such as during light exercise, in order to provide continuous monitoring of their blood pressure.

Positioning and Use Methodology

Figure 6:
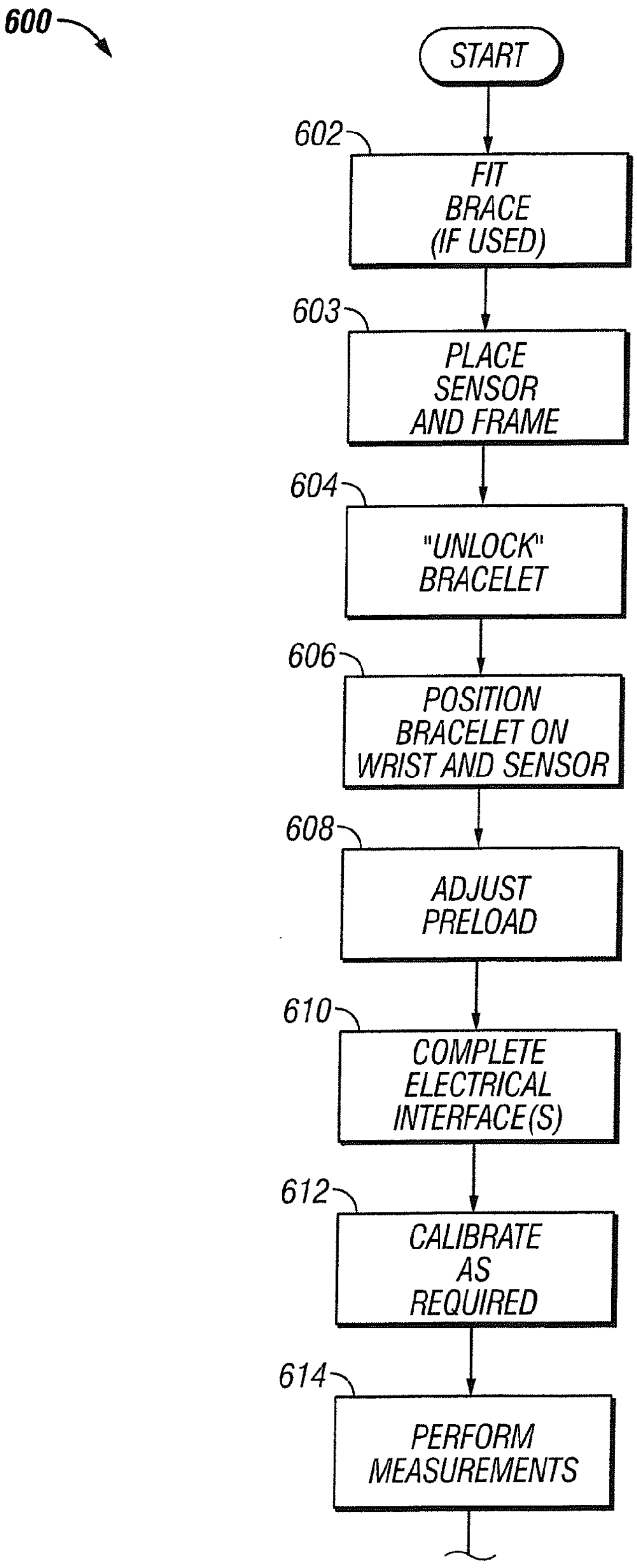
FIGS. 6 and 6*a* are logical flow diagrams illustrating one exemplary embodiment of the method of positioning and utilizing a sensor according to the invention.
Figure 6A:
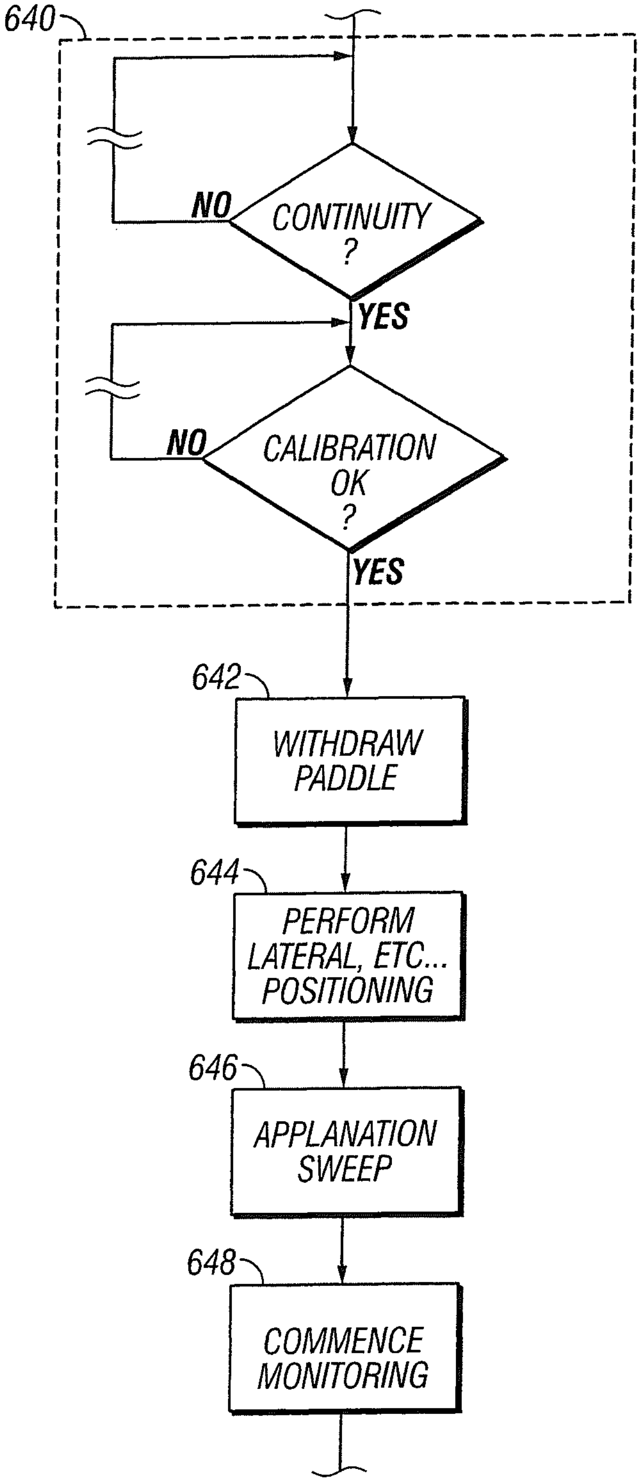

Referring now to FIGS. 6 and 6*a*, the general methodology of positioning the non-invasive sensor and apparatus 110 with respect to the anatomy of the subject is described in detail. It will be recognized that while the following discussion is cast in terms of the placement of a tonometric pressure sensor used for measuring arterial blood pressure, the methodology is equally applicable to both other types of sensors and other parts of the subject's anatomy, human or otherwise.

Furthermore, while cast in terms of the embodiment of FIGS. 1-4*d*, the methodology is equally applicable to other hardware configurations with proper adaptation, such adaptation being readily performed by those of ordinary skill provided the present disclosure.

As shown in FIG. 6, the illustrated embodiment of the method 600 generally comprises first placing the brace apparatus 195 previously described herein with respect to FIG. 1*a* (if the brace 195 is to be used). The brace 195 is fitted to the subject's forearm per step 602. This provides a stable platform against which the bracelet 110 can act. Alternatively, the bracelet can be used alone without the brace, with the anterior portion of the bracelet providing the necessary stabilization and reaction force as previously described.

Next, the user disposes the sensor relative to the blood vessel of the subject which is to be monitored (step 603). In the exemplary embodiment, the sensor assembly 101 comes "assembled" and pre-packaged, such that the user merely opens the package, removes the backing sheet and places a reticle (and associated frame element) over the target area of the blood vessel, thereby aligning the sensor over the target. This process is described in detail in co-pending and co-owned U.S. application Ser. No. 10/269,801 filed Oct. 11, 2002 and Ser. No. 10/920,999 filed Aug. 17, 2004 previously incorporated herein.

Next, per step 604, the apparatus 110 is placed in the "unlocked" state if not already there (such as by actuating the buttons 125 or other mechanism to release the pivot element 120 and its clutch mechanisms 123 in the embodiment of FIG. 1. This allows the interior and anterior elements 114, 116 to move relative to the pivot element 120, and the gap 117 to open wide enough to pass the apparatus 110 over the subject's limb. It also allows the distal portion of the anterior element 116 to pivot around its axis. In the illustrated embodiment, the apparatus 110 is designed to be placed from the medial side of the wrist, although other configurations may be used.

During placement of the apparatus 110 over the wrist (step 606), the user also aligns the adapter 104 of the sensor assembly 101 with the corresponding adapter element 377 of the actuator 106. The two components 104, 377 are designed to have a frictional or interference fit, such that when "snapped" together, the sensor 101 will remain suspended within the adapter element 377. Additionally, as previously discussed, the alignment frame 132 and bracelet 110 may optionally be configured so as to removably couple to each other, thereby further aligning the sensor assembly dome 104 and actuator adapter 377.

In one embodiment of the methodology, the user unlocks the apparatus 110 by pressing the buttons 125, and then first places the adapted 377 generally over dome or pyramid the sensor assembly 101, and concurrently "snapping in" the latching portions 304 of the sides of the interior element 114 to the sensor side arms 177 of the support frame 132, and then wrapping the rest of the apparatus 110 around the subject's wrist.

During placement, the contact pad 191 of the anterior element 116 is also placed atop the corresponding pad 193 (if present) of the brace element 195, thereby allowing the two pads to engage one another. For example, such engagement may be via complementary Velcro pads (see FIGS. 1 and 1*a*), or any other number of pivot mechanisms readily appreciated by those of ordinary skill. This movably yet firmly couples the anterior element 116 to the brace 195, thereby substantially removing all compliance of the subject's tissue, and also providing a pivot or fulcrum for the anterior element 116 during operation.

After the sensor assembly 101, interior element 114 with actuator, and anterior element 116 are aligned, and the apparatus 110 is properly oriented on the subject's limb, the user adjusts the preload or static compression of the apparatus 110 (step 608). In the exemplary embodiment, this adjustment is accomplished by the user grasping the apparatus 110 in one hand, with thumb on the outer surface of the interior element 114, and forefinger(s) on the outer surface of the anterior element 116 (over the preload mechanism actuator lever 221). As the user compresses the apparatus 110 around the subject's wrist, the reaction force created by the tissue compression causes the force applied to the actuator lever 221 to increase, and eventually transition the preload mechanism to actuate the trigger mechanism 137 when the desired preload level has been achieved. This trigger mechanism actuation locks both the axes 121*a*, 121*b* of the pivot mechanism 120 in place, as well as locking the distal portion of the anterior element 116 in place around its axis of rotation. Hence, the user need do nothing else to adjust the preload level, since when the proper preload is achieved, the device is “frozen” in place automatically.

As previously discussed, other mechanisms and techniques for determining proper preload may also be utilized, the foregoing approach being merely exemplary.

During the compression of step 608, the force applied to the sensor/adapter coupling is also sufficient to ensure that the two components (i.e., sensor dome and adapter 377) are “snapped” or affirmatively coupled together if not already done so.

Next, per step 610, the electrical interface between the sensor assembly 101 and the apparatus 110 is completed, in the illustrated embodiment by plugging the free end of the sensor pigtail 197 (see FIG. 1*c*) into the interface port 131. This allows for data communication between the sensor assembly 101 (and its components, including EEPROM) and the parent monitoring device for operation, calibration, etc. The system is now ready for use, whereby the user can calibrate the apparatus 110 as necessary (step 612) and obtain continuous hemodynamic measurements (step 614). As previously described, another variant of the sensor and adapter apparatus allows for a direct electrical or signal interface to be established at the time the sensor assembly 101 is received into the adapter 377, thereby obviating the pigtail 107 and the step of inserting it.

While the foregoing method has been found by the Assignee hereof to have substantial benefits including ease of use and low cost, it will be recognized that any number of different combinations of these or similar steps may be used (as well as different apparatus). For example, it is feasible that the manufacturer may wish to provide the components as a kit, which the user assembles. Alternatively, different configurations of sensor may be used, such as where the sensor is adapted for installation onto the apparatus 110 before placement of the latter around the subject’s limb.

Clearly, myriad other different combinations and configurations of the basic methodology of disposing a sensor with respect to a desired point on the subject’s anatomy will be recognized by those of ordinary skill given the present disclosure. The present discussion should therefore in no way be considered limiting of this broader method.

In operation (FIG. 6*a*) and after placement and adjustment of the apparatus 110 per the method 600 of FIG. 6, the user first awaits an electrical (e.g., LED) indication of continuity between the sensor and the parent device and proper calibration/authentication (step 640), and then withdraws the sensor paddle 133 from the sensor assembly (step 642), thereby freeing the sensor assembly 101 under guidance of the actuator 106, and optionally deploying a conditioning agent (e.g., powder) if so configured. The control algorithms within the parent controller then place the sensor element properly over the blood vessel of interest using lateral and longitudinal positioning routines such as those described in the aforementioned patent applications (step 644), and perform an applanation sweep or otherwise adjust the level of compression applied by the sensor element (step 646) in preparation for continuous hemodynamic monitoring (step 648).

As will be recognized, any number of different calibration, authentication, and/or functional checks (step 640) may be utilized consistent with the present invention. For example, the sensor assembly may be tested to verify inter alfa (i) proper physical/electrical configuration (i.e., that it is in fact the right model device for use with the apparatus 110), (ii) proper calibration and sensor operation, (iii) age since manufacture, and (iv) that it has not been used before on another patient, and so forth. Exemplary component configurations and test protocols useful with the present invention are described in, inter alia, co-owned U.S. Pat. No. 6,676,600 previously incorporated herein, although other techniques and configurations may also be used.

It will also be recognized that the adjustment of the apparatus 110 on the subject’s anatomy may be guided by other data or indications, including for example the amplitude of the maximum pulsatile pressure of the subject (as measured by the tonometric pressure sensor element 105 or other means). Specifically, the preload or static compression level may be readjusted or “fine tuned” interactively using data from the sensor or other input after initial calibration and system checks have been performed. There may be instances, for example, where the compliance or character of the subject’s tissue changes (such as upon administration of anesthesia), wherein some readjustment of the preload is desired. These changes are also accounted for where the control algorithms described in co-owned and co-pending U.S. application Ser. No. 10/211,115 entitled “Method and Apparatus for Control of Non-Invasive Parameter Measurements” filed Aug. 1, 2002 and incorporated herein by reference in its entirety, are used. For example, the various processes of the aforementioned control algorithms are useful in detecting changes in the monitoring environment including, e.g., gradual or non-transient changes in coupling such as those described above.

Figure 7:
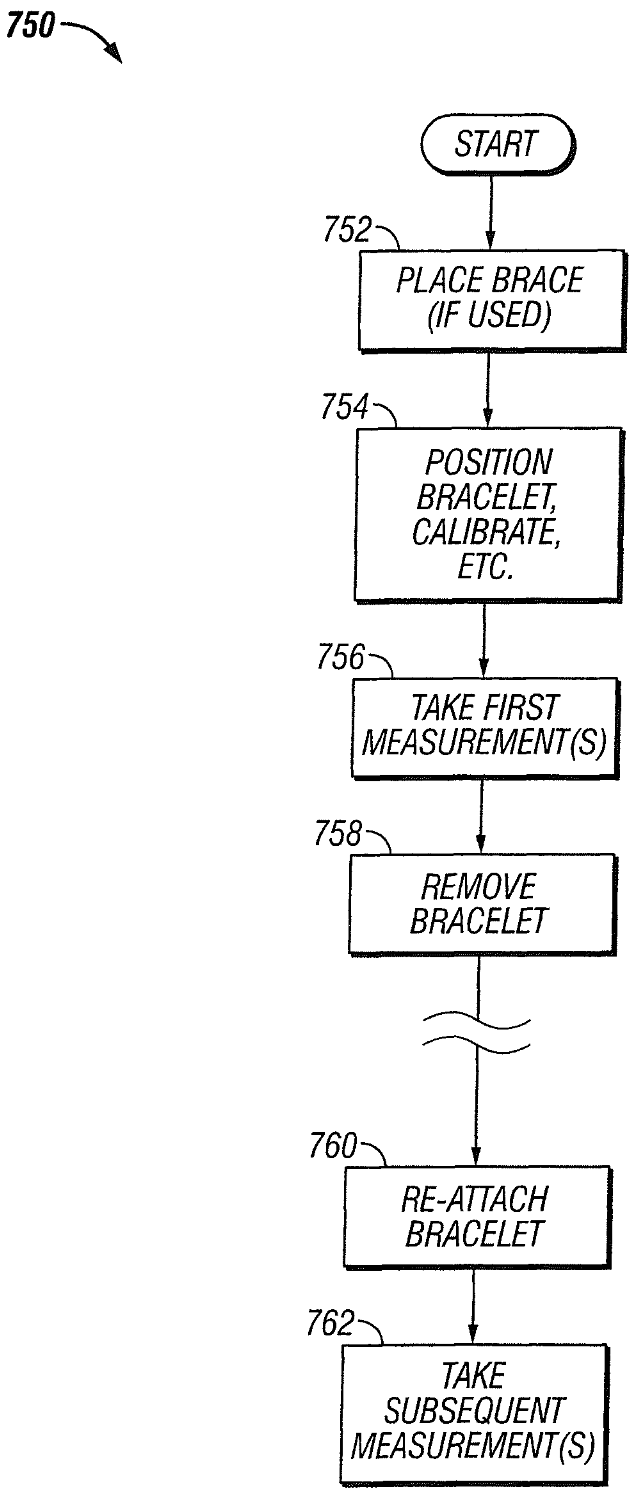
FIG. 7 is a logical flow diagram illustrating one exemplary embodiment of the method of performing multiple hemodynamic measurements according to the invention.

Referring now to FIG. 7, one exemplary embodiment of the improved method of recurrently measuring the blood pressure of a living subject is described. As before, the present context of the discussion is merely exemplary of the broader techniques of the invention.

As shown in FIG. 7, the method 750 comprises first placing a brace element 195 or other comparable structure on the subject if required (i.e., where the bracelet embodiment of FIG. 1 is used). In the case of the radial artery, the brace 195 is placed on the back (anterior) portion of the subject’s wrist and forearm, and secured thereto.

Next, an alignment apparatus adapted to align one or more sensors with respect to the anatomy of the subject is disposed on the subject’s limb (step 752). The apparatus may be the alignment apparatus associated with the sensor assembly previously described herein, including any alternatives of forms thereof, or yet other devices which perform a comparable function. The sensor(s) is/are accordingly positioned with respect to the anatomy using the alignment apparatus (e.g., in the context of the exemplary embodiment of FIG. 1*e*, the sensor is aligned with respect to the support frame element 132).

The bracelet apparatus 110 is then positioned on the patient, and adjusted, calibrated, etc. per step 754 (see FIG. 6).

The blood pressure (or other hemodynamic parameter) is then measured using the sensor(s) at a first time per step 756. For example, this first measurement may occur during surgery in an operating room.

The bracelet is then removed (if desired) per step 758. The sensor and frame element 132 are left in place.

The bracelet is subsequently repositioned on the patient (step 760), such as after the patient has been moved to another location.

Lastly, the blood pressure or other parameter(s) of the subject are again measured using the sensor(s) at a second time subsequent to the first (step 762). Specifically, the sensor position is maintained with respect to the anatomy between measurements using the alignment apparatus 132; i.e., the sensor assembly 101 is maintained generally atop the desired pulse point of the subject even after the actuator 106 is decoupled from the sensor 101. Herein lies a significant advantage of the present invention, in that the apparatus 110, including bracelet elements 114, 116 and pivot element 120 can be removed from the subject, leaving the alignment apparatus 132 and sensor assembly 101 in place. It may be desirable to remove the bracelet apparatus 110 for example where transport of the subject is desired and the present location has dedicated equipment which must remain, or the monitored subject must have the bracelet 110 removed to permit another procedure (such as post-surgical cleaning, rotation of the subject's body, etc.). The sensor assembly 101 position is maintained effectively constant with respect to the subject pulse point when the bracelet apparatus 110 (including actuator 106) is removed, such as during the foregoing evolutions.

Hence, when it is again desired to monitor the subject using the sensor, the bracelet 110 (or another similar device at the destination) is fitted to the subject, and the preload adjusted such that the actuator 106 is coupled to the alignment frame 132 and the desired preload compression is achieved. Accordingly, no use of a second alignment apparatus or other techniques for positioning the sensor "from scratch" is needed, thereby saving time and cost. This feature further allows for more clinically significant or comparable results since the same sensor is used with effectively identical placement on the same subject; hence, and differences noted between the first and second measurements discussed above are likely not an artifact of the bracelet apparatus 110.

It will be further recognized that while two measurements are described above, the methodology of FIG. 7 allows for multiple such sequential decoupling-movement-recoupling events without having any significant effect on the accuracy of any measurements. For example, the exemplary serpentine sensor-restraining apparatus shown in FIG. 1*e* is specifically designed to have a high tensile strength so as to withstand both paddle removal and separation of the sensor from the actuator under a multiple-use scenario such as that described above with respect to FIG. 7.

Method of Providing Treatment

A method of providing treatment to a subject using the aforementioned methods is disclosed. The first step of the method comprises selecting the blood vessel and location to be monitored. For most human subjects, this will comprise the radial artery (as monitored on the inner portion of the wrist), although other locations may be used in cases where the radial artery is compromised or otherwise not available.

Next, if the brace element 195 previously described herein is to be used, the brace 195 is fitted to the subject's forearm. This provides a stable platform against which the bracelet 110 can act. Alternatively, the bracelet can be used alone without the brace, with the anterior portion of the bracelet providing the necessary stabilization and reaction force as previously described.

Next, the alignment apparatus (support frame) 132 is placed in the proper location with respect to the subject's blood vessel, and adhered to the skin according to for example the method of FIG. 6. Such placement may be accomplished manually, i.e., by the caregiver or subject by identifying the desired pulse point (such as by feel with their finger) and visually aligning the transducer and device over the interior portion of the wrist, by the pressure/electronic/acoustic methods of positioning previously referenced, or by other means. At the conclusion of this step, the sensor assembly 101 is aligned above the blood vessel within the alignment frame element 132 with the paddle installed.

Next, the bracelet 110 is fitted to the patient. The adapter 377 of the actuator 106 is coupled to the sensor dome 104 (and the frame 132 latched to the bracelet or interior element 114 if so equipped). The anterior element is also positioned on the brace element 195 so as to couple the two components, thereby completing the mechanical linkages between the various components. Similarly, the actuator end of the electrical interface 107 is coupled to the bracelet 110 via the port 131 disposed on the body of the latter, and electrical continuity between the sensor assembly 101 and actuator 106 established. The free end of the bracelet interface cable is then connected to the parent monitoring system as required, or alternatively a wireless interface established.

Next, the operation and continuity of the various devices are tested by the actuator and associated circuitry (and sensors) as previously described, and a visual indication of the results of these tests provided to the user via, e.g., the indicator LEDs or LCDs, audible tones, or other similar means. Once the system electrical functions have been satisfactorily tested (including, e.g., the suitability of the sensor assembly for use on the current subject, shelf-life, etc.) and either the paddle 133 detected or the calibration data read in the EEPROM, the indicators 182 show a green color indicating that the paddle may be removed, and the measurements commenced.

The user then grasps the paddle and pulls outward away from the bracelet 110 and frame 132, thereby decoupling the sensor 101 from the paddle, and decoupling the paddle from the frame element 132. The control of the sensor assembly 101 is now passed to the actuator 106, and the measurement process including any lateral positional adjustments may be performed. The optimal applanation level is also then determined as part of the measurement process. Co-pending U.S. patent application Ser. No. 10/072,508 previously incorporated herein illustrates one exemplary method of finding this optimum applanation level, although others may be used.

Once the optimal level of applanation and lateral position are set, the pressure waveform is measured, and the relevant data processed and stored as required. Such processing may include, for example, calculation of the pulse pressure (systolic minus diastolic), calculation of mean pressures or mean values over finite time intervals, and optional scaling or correction of the measured pressure waveform(s). One or more resulting outputs (e.g., systolic and diastolic pressures, pulse pressure, mean pressure, etc.) are then generated. Software processes within the parent monitoring system are then implemented as required to maintain the subject blood vessel and overlying tissue in a continuing state of optimal or near-optimal compression (as well as maintaining optimal lateral/proximal position if desired) so as to provide continuous monitoring and evaluation of the subject's blood pressure. This is to be distinguished from the prior art techniques and apparatus, wherein only periodic representations and measurement of intra-arterial pressure are provided.

Additionally, the potentially varying elevation of the bracelet apparatus 110 previously described herein (including the sensor assembly) during blood pressure measurement with respect to one or more organs of interest may be considered and compensated for. Additionally, heuristically or even deterministically-based corrections of the pressure measurements for hydrodynamic effects may be applied. Apparatus and methods for providing such compensation and corrections are described in co-pending and co-owned U.S. patent application Ser. Nos. 10/269,801 filed Oct. 11, 2002 and Ser. No. 10/920,999 filed Aug. 17, 2004, both previously incorporated herein by reference in their entirety, although other methods may be used as well consistent with the present invention.

Similarly, the exemplary apparatus described herein may be optionally adapted to determine whether it is installed on the left arm or right arm of the subject, and adjust its operation accordingly. This functionality and configuration is described in detail in the aforementioned U.S. patent application Ser. No. 10/920,999 previously incorporated herein. The primary benefit afforded by this determination and adjustment is consistency of measurement and removal of variables from the measurement process. Specifically, by having the control algorithm maintain a uniform direction of scan/traversal with respect to the bracelet apparatus 110, any artifacts created or existing between the various components of the apparatus and the subject's physiology are maintained constant throughout all measurements. Hence, the situation where such artifacts affect one measurement and not another is eliminated, since the artifacts will generally affect (or not affect) all measurements taken with the apparatus 110 equally.

Lastly, the "corrected" continuous measurement of the hemodynamic parameter (e.g., systolic and/or diastolic blood pressure) is used as the basis for providing treatment to the subject. For example, the corrected systolic and diastolic blood pressure values are continuously generated and displayed or otherwise provided to the health care provider in real time, such as during surgery. Alternatively, such measurements may be collected over an extended period of time and analyzed for long term trends in the condition or response of the circulatory system of the subject. Pharmacological agents or other courses of treatment may be prescribed based on the resulting blood pressure measurements, as is well known in the medical arts. Similarly, in that the present invention provides for continuous blood pressure measurement, the effects of such pharmacological agents on the subject's physiology can be monitored in real time.

It will be appreciated that the foregoing methodology may also be readily adapted to multiple hemodynamic measurements as discussed with respect to FIG. 7.

It is noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

What is claimed is:

1. Non-invasive hemodynamic monitoring apparatus comprising:

a bracelet-like structure configured to receive a patient's wrist said bracelet-like structure comprising:

a first portion configured to interface with an inner portion of said patient's wrist, said first portion comprising a first actuator assembly at least partially enclosed within a housing said first actuator assembly configured to couple to at least one sensor and position said at least one sensor according to at least one of a sagittal displacement and a lateral displacement;

a second portion configured to interface with an exterior portion of said patient's wrist; and a third portion pivotally coupled to said first and second portions, said third portion further comprising a second actuator assembly configured to allow selective control of a motion of said first and second portions according to a static compression of said bracelet-like structure on said patient's wrist; and signal processing apparatus in communication with said at least one sensor, said signal processing apparatus configured to generate scaled hemodynamic signals based on data obtained from said patient via said at least one sensor.

2. The apparatus of claim 1, wherein said scaled hemodynamic signals comprise scaled blood pressure signals.

3. The apparatus of claim 1, wherein said at least one sensor comprises a silicone interface medium configured to interface with skin disposed at said patient's wrist.

4. The apparatus of claim 1, further comprising a sensor support frame flexibly coupled to said at least one sensor, said sensor support frame further configured to couple to said bracelet-like structure.

5. A method of measuring one or more physiologic parameters of a living subject, comprising:

temporarily affixing a sensing assembly to said living subject at a position above a blood vessel thereof, said sensor assembly comprising at least a sensor element and an alignment apparatus, said alignment apparatus configured to assist in alignment of said sensor element above said blood vessel in at least one lateral dimension;

positioning a bracelet-like actuator assembly over said sensing assembly such that a first portion thereof is configured to interface with an inner portion of a wrist of said living subject, and a second portion thereof is configured to interface with an exterior portion of said wrist of said living subject;

obtaining data relating to one or more physiologic parameters of said living subject; and scaling said data based at least in part on measurement of one or more physiologic characteristics of said living subject;

wherein a third portion of said bracelet-like actuator is pivotally coupled to said first and second portions and further comprises an actuator assembly configured to allow selective control of a motion of said first and second portions according to a static compression of said bracelet-like structure on said wrist of said living subject.

6. The method of claim 5, wherein said first portion of said bracelet-like actuator further comprises a second actuator assembly at least partially enclosed within a housing, said second actuator assembly configured to couple to said sensor element and position said sensor element according to at least one of a sagittal displacement and a lateral displacement.

7. The method of claim 5, wherein said act of positioning said bracelet-like actuator assembly comprises locking one or more features of said bracelet-like actuator assembly when a predetermined level of compressive force is applied thereto.

8. The method of claim 5, further comprising utilizing said bracelet-like actuator assembly to position said sensor element over said blood vessel, and to applanate said sensor element to achieve said predetermined level of compressive force.

9. The method of claim 5, further comprising utilizing said bracelet-like actuator assembly to position said sensor element over said blood vessel, and to applanate said sensor element to achieve a desired level of signal coupling to said blood vessel.

10. The method of claim 5, wherein said one or more physiologic characteristics of said living subject comprise a body mass index (BMI).

11. Non-invasive hemodynamic assessment apparatus comprising:

a bracelet assembly configured to adjustably clamp onto a limb of a patient proximate a blood vessel of interest, said bracelet assembly comprising:

a first actuator disposed on a first portion of said bracelet assembly, said first portion configured to interface with an inner portion of said patient's wrist; and a second actuator disposed on a second portion of said bracelet assembly, said second portion being pivotally coupled to said first portion of said bracelet assembly and a third portion of said bracelet assembly, said third portion of said bracelet assembly configured to interface with an exterior portion of said patient's wrist; and signal processing apparatus in signal communication with at least one sensor and configured to process signals generated by said at least one sensor and generate scaled hemodynamic signals based thereon;

wherein said first actuator apparatus is configured to position the at least one sensor over said blood vessel of interest; and wherein said second actuator apparatus is configured to allow selective control of a motion of said first and third portions of said bracelet assembly according to a static compression of said bracelet-like structure on said patient's wrist.

12. The non-invasive hemodynamic assessment apparatus of claim 11, wherein said at least one sensor is configured to, in conjunction with said signal processing apparatus, perform a tonometric measurement of a blood pressure of said blood vessel, and where said first actuator apparatus is configured to position said at least one sensor according to a sagittal displacement configured to optimize said tonometric measurement.

13. The non-invasive hemodynamic assessment apparatus of claim 12, wherein said tonometric measurement is continuously performed.

14. The non-invasive hemodynamic assessment apparatus of claim 11, wherein said static compression is based on one or more preloaded compression levels.

15. The non-invasive hemodynamic assessment apparatus of claim 14, wherein said one or more preloaded compression levels trigger a locking mechanism.

16. The non-invasive hemodynamic assessment apparatus of claim 11, wherein said at least one sensor comprises a disposable silicone interface medium configured to interface with a skin of said patient.

* * * * *